(12) United States Patent
Bongiorni et al.

(10) Patent No.: US 11,306,319 B2
(45) Date of Patent: Apr. 19, 2022

(54) ENHANCED PROTEIN EXPRESSION AND METHODS THEREOF

(71) Applicant: DANISCO US INC, Palo Alto, CA (US)

(72) Inventors: Cristina Bongiorni, Palo Alto, CA (US); Marguerite A. Cervin, Palo Alto, CA (US); George England, Palo Alto, CA (US); Chao Zhu, Palo Alto, CA (US); Frank Wouter Koopman, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 686 days.

(21) Appl. No.: 15/771,618

(22) PCT Filed: Oct. 27, 2016

(86) PCT No.: PCT/US2016/059078
§ 371 (c)(1),
(2) Date: Apr. 27, 2018

(87) PCT Pub. No.: WO2017/075195
PCT Pub. Date: May 4, 2017

(65) Prior Publication Data
US 2018/0327757 A1    Nov. 15, 2018

Related U.S. Application Data

(60) Provisional application No. 62/248,757, filed on Oct. 30, 2015.

(51) Int. Cl.
| | | |
|---|---|---|
| *C12N 15/00* | (2006.01) | |
| *C12N 15/75* | (2006.01) | |
| *C12N 9/12* | (2006.01) | |
| *C12P 21/02* | (2006.01) | |
| *C12P 21/00* | (2006.01) | |
| *C12N 1/20* | (2006.01) | |
| *C12R 1/01* | (2006.01) | |

(52) U.S. Cl.
CPC .............. *C12N 15/75* (2013.01); *C12N 1/205* (2021.05); *C12N 9/1247* (2013.01); *C12P 21/00* (2013.01); *C12P 21/02* (2013.01); *C12N 2320/50* (2013.01); *C12N 2330/51* (2013.01); *C12N 2800/101* (2013.01); *C12R 2001/01* (2021.05)

(58) Field of Classification Search
CPC ...... C12N 15/75; C12N 1/205; C12N 9/1247; C12N 2320/50; C12N 2330/51; C12N 2800/101; C12R 2001/01; C12P 21/00; C12P 21/02

See application file for complete search history.

(56) References Cited

FOREIGN PATENT DOCUMENTS

| WO | 003055996 A1 | 7/2003 | |
| WO | WO-03055996 A1 * | 7/2003 | ........... C12N 9/1247 |
| WO | 2014208981 A1 | 12/2014 | |

OTHER PUBLICATIONS

Yang et al entitled "Streptolydigin resistance can be conferred by alterations to either the beta or beta' subunits of Bacillus subtilis RNA polymerase" (JBC, vol. 270, No. 41, Jul. 13, 1995, pp. 23930-23933) (Year: 1995).*
Matsuo et al (AAC vol. 59, No. 7, published online May 4, 2015. (Year: 2015).*
Yang et al (Plasmid 2014: vol. 75, pp. 37-41, published online Jun. 30, 2014.) (Year: 2014).*
Score Result for Yang et al 1995 (Year: 1995).*
Yang, et al., Streptolydigin resistance can be conferred by alterations to either the beta or beta' subunits of *Bacillus subtilis* RNA polymerase, Journal of Biological Chemistry, American Society for Biochemistry and Molecular Biology, vol. 270, No. 41, Oct. 13, 1995, p. 23930-23933.
Brinkman, et al. Characterization of the Effects of an rpoC Mutation that Confers Resistance to the Fst Peptide Toxin-Antitoxin System Toxin, Journal of Bacteriology, vol. 195, No. 1, Oct. 26, 2012, pp. 156-166.
Lee et al., A Mutation of the RNA Polymerase B Subunit (rpoC) Confers Cephalosporin Resistance in Bacillus Subtilis, Antimicrobial Agents and Chemotherapy, vol. 57, No. 1, Oct. 15, 2012, pp. 56-65.

(Continued)

*Primary Examiner* — Catherine S Hibbert

(57) ABSTRACT

The present disclosure is generally related to modified Gram positive bacterial cells producing increased amounts of one or more protein(s) of interest and modified Gram positive bacterial cells having increased genetic competency. Thus, certain embodiments of the disclosure are directed to modified Gram positive bacterial cells expressing an increased amount of a protein of interest, relative to an unmodified (parental) Gram positive bacterial cell expressing the same protein of interest, wherein the modified bacterial cell comprises at least one mutation in a rpoC gene encoding a variant RNA-polymerase (RNAP) β'-subunit polypeptide. In certain embodiments, the rpoC gene encoding the variant β'-subunit polypeptide is integrated into the chromosome of the modified cell. In other embodiments, the rpoC gene encoding the variant β'-subunit polypeptide is comprised on an extrachromosomal plasmid introduced into the modified cell. In other embodiments, the disclosure is directed to competent *Bacillus* host cells comprising at least one copy of a nucleic acid construct encoding a modified rpoC polypeptide comprising 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct.

10 Claims, 12 Drawing Sheets

Specification includes a Sequence Listing.

(56) References Cited

OTHER PUBLICATIONS

Chen et al., Adaptation of *Lactococcus lactis* to high growth temperature leads to a dramatic increase in acidification rate, Scientific Reports, vol. Sep. 21, 2015, p. 14199.

Cheng et al., Global metabolic network reorganization by adaptive mutations allows fast growth of *Escherichia coli* on glycerol, Nature Communications, vol. 3, Jan. 31, 2014, 9 pgs.

Conrad et al., RNA polymerase mutants found through adaptive evolution reprogram *Escherichia coli* for optimal growth in minimal media, Proceedings of the National Academy of Sciences, vol. 107, No. 47. Nov. 23, 2010 p. 20500-20505.

Fukuda et al., Comparative Studies of RNA Polymerase Subunits from Various Bacteria, Molecular and General Genetics, vol. 154, p. 135-144, Jul. 1977.

Maughan et al., Novel rpoB Mutations Conferring Rifampin Resistance on *Bacillus subtilis*: Global Effects on Growth, Competence, Sporulation and Germination, Journal of Bacteriology, vol. 186, No. 8, Apr. 2004, p. 2481-2486.

* cited by examiner

US 11,306,319 B2

ENHANCED PROTEIN EXPRESSION AND METHODS THEREOF

CROSS REFERENCE TO RELATED APPLICATIONS

This application claims benefit to U.S. Provisional Application No. 62/248,228 filed Oct. 30, 2015, which is hereby incorporated by reference in its entirety.

FIELD OF THE INVENTION

The instant disclosure is generally related to the fields of microbiology, molecular biology, enzymology, protein engineering and the like. In certain embodiments, the present disclosure relates to modified Gram positive bacterial cells producing increased amounts of one or more protein(s) of interest. In certain other embodiments, the disclosure is directed to modified Gram positive bacterial cells comprising increased genetic competency.

SUBMISSION OF SEQUENCE LISTING

The contents of the electronic submission of the text file Sequence Listing, which is named "NB40948WOPCT_SEQ.txt" was created on Oct. 12, 2016 and is 71 KB 71,817 bytes in size, is hereby incorporated by reference in its entirety.

BACKGROUND

Various techniques have been developed to improve the industrial production of polypeptides, including, for example, classical strain improvement methods, such as subjecting strains to multiple rounds of mutagenesis and selection for high producers, building or genetically engineering a production strain with high or higher than native copy number of the gene(s) of interest inserted into the genome, introducing into multiple copies of suitable expression vectors into a production strain, the improvement of vectors, promoters, fusion expression, co-expression of proteins of interest with molecular chaperones, and the like.

While many of the above referenced methods and techniques are effective at improving productivity of the host microbial strains, they nearly all have limitations, such as the labor intensity of rounds of strain construction exercises in order to make individual products, unstable plasmids especially at high copy numbers becoming lost during cultivation of the host cells, instability of the host cell caused by the integration of multiple copies of a gene into the chromosome thereof, and so on.

Thus, there remains a need in the art for improved host and/or production strains capable of increased protein production of a single protein of interest, increased protein production of one or more proteins of interest, increased protein production of one or more panels of proteins of interest, increased protein production of endogenous proteins and the like.

RNA-polymerase (hereinafter, "RNAP") is one of the most central transcriptional regulatory hubs, and the most studied bacterial RNAP is the *E. coli* RNAP, which is representative of RNAP enzymes isolated from a number of bacterial genera, including *Salmonella, Serratia, Proteus, Aerobacter* and *Bacillus* (see, Fukuda et al., 1977).

The RNAP "core enzyme" is comprised of α (alpha), 3 (beta), and β' (beta') subunits in a 2:1:1 ratio, respectively. The RNAP α (alpha), 3 (beta), and β' (beta') subunits are encoded by the rpoA, rpoB, and rpoC genes, respectively.

Mutations affecting RNAP can arise during the execution of well-known selection protocols (Conrad et al., 2010; Cui et al., 2010). Mutant versions of the α-subunit (RpoA) protein, can at times substantially alter the cellular phenotype (Klein-Marcuschamer et al., 2009). Likewise, certain mutations in β-subunit (RpoB) protein, which lead to rifampin resistance in *Bacillus subtilis*, correlate with altered expression and/or regulations involved in growth, competence, sporulation, and germination (Maughan et al., 2004).

For example, one result of such a β-subunit alteration might be an increase in gene activity, although in other cases such an alteration may lead to little or no effect (Kane et al., 1979). Varying levels of phosphatase activity have been reported for rifampicin resistant strains (e.g., see, Sharipova et al., 1994). It also has been reported that at least one mutation in the β-subunit (RpoB) protein results in an altered production of a product of interest (PCT International Publication No. WO2003/055996).

In addition, mutations of the β'-subunit (RpoC) protein have been proposed to allow regulatory adaptation for optimal growth in minimal medium (Conrad et al., 2010), and lead to resistance to cefuroxime (CEF) resistance (Lee et al., 2013).

As set forth below in the Detailed Description, the instant disclosure addresses an unmet need in the art for bacterial cells capable of expressing and producing increased amounts of one or more proteins of interest. More particularly, the instant disclosure addresses a need in the art for improved bacterial (host) cells capable of increased production of a single protein of interest, increased production one or more proteins of interest, increased production one or more panels of proteins of interest, increased production of endogenous proteins and the like. In yet other embodiments, the disclosure addresses an unmet need in the art for Gram positive bacterial cells (e.g., a *Bacillus* sp. host cell) having improved or increased genetic competency, thereby leading to a higher frequency of transformed cells thereof.

SUMMARY

The present disclosure is generally related to modified Gram positive bacterial cells producing increased amounts of one or more protein(s) of interest. Thus, in certain embodiments, the disclosure is directed to a modified Gram positive bacterial cell expressing an increased amount of a protein of interest (POI) relative to an unmodified Gram positive bacterial cell, wherein the modified bacterial cell comprises at least one mutation in a rpoC gene encoding a variant RNA-polymerase (RNAP) β'-subunit polypeptide. In certain embodiments, the rpoC gene encoding the variant β'-subunit polypeptide is integrated into the chromosome of the modified cell. In other embodiments, the rpoC gene encoding the variant β'-subunit polypeptide is comprised on an extrachromosomal plasmid of the modified cell. In another embodiment, the rpoC gene encoding the variant β'-subunit polypeptide comprising the at least one mutation is derived from a wild-type rpoC gene, or a variant thereof, comprising at least 80% sequence identity to SEQ ID NO: 5. In certain other embodiments, the rpoC gene encodes a variant β'-subunit polypeptide comprising at least 90% sequence identity to SEQ ID NO: 6. In yet another embodiment, the rpoC gene encoding the variant β'-subunit polypeptide comprising the at least one mutation is derived from a wild-type rpoC gene, or a variant thereof, comprising at least 80% sequence identity to SEQ ID NO: 7. In certain embodiments, the rpoC gene encodes a variant β'-subunit polypeptide comprising at least 90% sequence identity to SEQ ID NO: 8. In certain other embodiments, the variant β'-subunit polypeptide of SEQ ID NO: 6 comprises at least one mutation at amino acid residue position 751, 784, 797, 796 and/or 1018-1020 of SEQ ID NO: 6, or at the equivalent position in any bacterial RNAP β'-subunit family member.

In yet other embodiments, the variant β'-subunit polypeptide comprises at least one mutation selected from the group consisting of a methionine to isoleucine substitution at amino acid residue 751 (M751 I) of SEQ ID NO: 6, an arginine to histidine substitution at amino acid residue 784 (R784H) of SEQ ID NO: 6, a serine to phenylalanine substitution at amino acid residue 797 (S797F) of SEQ ID NO: 6, an aspartic acid to glycine substitution at amino acid residue 796 (D796G) of SEQ ID NO: 6 and/or a deletion of amino acid residues 1,018, 1,019 and 1,020 (ΔI1018-R1020) of SEQ ID NO: 6. In another embodiment, the variant β'-subunit polypeptide of SEQ ID NO: 8 comprises at least one mutation at amino acid residue position 751, 784, 797, 796 and/or 1018-1020 of SEQ ID NO: 8, or at the equivalent position in any bacterial RNAP β'-subunit family member.

In other embodiments, the variant β'-subunit polypeptide comprises at least one mutation selected from the group consisting of a methionine to isoleucine substitution at amino acid residue 751 (M751 I) of SEQ ID NO: 8, an arginine to histidine substitution at amino acid residue 784 (R784H) of SEQ ID NO: 8, a serine to phenylalanine substitution at amino acid residue 797 (S797F) of SEQ ID NO: 8, an aspartic acid to glycine substitution at amino acid residue 796 (D796G) of SEQ ID NO: 8 and/or a deletion of amino acid residues 1,018, 1,019 and 1,020 (ΔI1018-R1020) of SEQ ID NO: 8.

In other embodiments, the modified cell further comprises at least one mutation in a rpoB gene encoding a variant RNAP β-subunit polypeptide. In certain embodiments, the rpoB gene comprising at least one mutation is derived from a wild-type rpoB gene, or a variant thereof, comprising at least 80% sequence identity to SEQ ID NO: 1. In certain other embodiments, the rpoB gene encodes a variant RNAP β-subunit polypeptide comprising at least 90% sequence identity to SEQ ID NO: 2. In another embodiment, the variant RNAP β-subunit polypeptide of SEQ ID NO: 2 comprises at least one mutation selected from the group consisting of an amino acid substitution at amino position 469, 478, 482, 485, or 487 of SEQ ID NO: 2, or at the equivalent position in any eubacterial RNAP β-subunit family member. In yet other embodiments, the variant RNAP β-subunit polypeptide comprises at least one mutation selected from the group consisting of an alanine to aspartic acid substitution at amino acid residue 478 (A478D) of SEQ ID NO: 2, a histidine to arginine substitution at amino acid residue 482 (H482R) of SEQ ID NO: 2, a histidine to tyrosine substitution at amino acid residue 482 (H482Y) of SEQ ID NO: 2, a histidine to proline substitution at amino acid residue 482 (H482P) of SEQ ID NO: 2 and a glutamine to lysine substitution at amino acid residue 469 (Q469K) of SEQ ID NO: 2.

In certain embodiments, the increased amount of an expressed POI relative to the unmodified Gram positive control cell is at least 5%. In another embodiment, the increased amount of an expressed POI relative to the unmodified Gram positive control cell is at least 10%.

In yet other embodiments, the Gram positive bacterial (host) cell is a Bacillaceae family member. In certain embodiments, the Gram positive bacterial cell is a *Bacillus* genus member. In yet other embodiments, the *Bacillus* cell is selected from *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii* and *B. thuringiensis*. In another embodiment, the *Bacillus* cell is *Bacillus subtilis* or *Bacillus licheniformis*.

In other embodiments, the POI is encoded by a gene exogenous to the modified bacterial cell or a gene endogenous to the modified bacterial cell. In other embodiments, the POI is secreted or transported extracellularly. In certain other embodiments, the POI secreted or transported extracellularly is isolated and purified.

In certain other embodiments, the POI is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Certain other embodiments are directed to an isolated protein of interest (POI) produced by a modified cell of the disclosure.

In other embodiments, the disclosure is directed to a method for increasing expression of a protein of interest (POI) in a Gram positive bacterial cell comprising (a) obtaining a modified Gram positive bacterial cell expressing an increased amount of a POI, wherein the modified bacterial cell comprises at least one mutation in a rpoC gene encoding a variant RNA-polymerase (RNAP) β'-subunit polypeptide, and (b) culturing the modified cell under conditions such that the POI is expressed, wherein the modified bacterial cell expressing an increased amount of a POI is relative to the expression of the POI in an unmodified Gram positive bacterial cell. In certain embodiments, the rpoC gene encoding the variant β'-subunit polypeptide is integrated into the chromosome of the modified cell. In other embodiments, the rpoC gene encoding the variant β'-subunit polypeptide is comprised on an extrachromosomal plasmid of the modified cell.

In other embodiments of the method, the rpoC gene encoding the variant β'-subunit polypeptide comprising the at least one mutation is derived from a wild-type rpoC gene, or a variant thereof, comprising at least 80% sequence identity to SEQ ID NO: 5. In certain other embodiments, the rpoC gene encodes a variant RNAP β'-subunit polypeptide comprising at least 90% sequence identity to SEQ ID NO: 6. In yet other embodiments, the rpoC gene encoding the variant β'-subunit polypeptide comprising the at least one mutation is derived from a wild-type rpoC gene, or a variant thereof, comprising at least 80% sequence identity to SEQ ID NO: 7. In another embodiment, the rpoC gene encodes a variant β'-subunit polypeptide comprising at least 90% sequence identity to SEQ ID NO: 8. In certain other embodiments, the variant RNAP β'-subunit polypeptide of SEQ ID NO: 6 comprises at least one mutation at amino acid residue position 751, 784, 797, 796 and/or 1018-1020 of SEQ ID NO: 6, or at the equivalent position in any bacterial RNAP β'-subunit family member.

In certain other embodiments of the method, the variant RNAP β'-subunit polypeptide comprises at least one mutation selected from the group consisting of a methionine to isoleucine substitution at amino acid residue 751 (M751 I) of SEQ ID NO: 6, an arginine to histidine substitution at amino acid residue 784 (R784H) of SEQ ID NO: 6, a serine to phenylalanine substitution at amino acid residue 797 (S797F) of SEQ ID NO: 6, an aspartic acid to glycine substitution at amino acid residue 796 (D796G) of SEQ ID NO: 6 and a deletion of amino acid residues 1,018, 1,019 and 1,020 (ΔI1018-R1020) of SEQ ID NO: 6. In another embodiment, the variant RNAP β'-subunit polypeptide of SEQ ID NO: 8 comprises at least one mutation at amino acid residue position 751, 784, 797, 796 and/or 1018-1020 of SEQ ID NO: 8, or at the equivalent position in any bacterial RNAP β'-subunit family member. In certain other embodiments, the variant RNAP β'-subunit polypeptide comprises at least one mutation selected from the group consisting of a methionine to isoleucine substitution at amino acid residue 751 (M751 I) of SEQ ID NO: 8, an arginine to histidine substitution at amino acid residue 784 (R784H) of SEQ ID NO: 8, a serine to phenylalanine substitution at amino acid residue 797 (S797F) of SEQ ID NO: 8, an aspartic acid to glycine substitution at amino acid residue 796 (D796G) of SEQ ID NO: 8 and a deletion of amino acid residues 1,018, 1,019 and 1,020 (ΔI1018-R1020) of SEQ ID NO: 8.

In other embodiments, the method further comprises a rpoB gene encoding a variant RNAP β-subunit polypeptide. In certain embodiments, the rpoB gene comprising at least one mutation is derived from a wild-type rpoB gene, or a variant thereof, comprising at least 80% sequence identity to SEQ ID NO: 1. In certain other embodiments, the rpoB gene encodes a variant RNAP β-subunit polypeptide comprising at least 90% sequence identity to SEQ ID NO: 2. In another embodiment, the variant RNAP β-subunit polypeptide of SEQ ID NO: 2 comprising at least one mutation selected from the group consisting of an amino acid substitution at amino position 469, 478, 482, 485, or 487 of SEQ ID NO: 2, or at the equivalent position in any eubacterial RNAP β-subunit family member. In yet other embodiments, the variant RNAP β-subunit polypeptide comprises at least one mutation selected from the group consisting of an alanine to aspartic acid substitution at amino acid residue 478 (A478D) of SEQ ID NO: 2, a histidine to arginine substitution at amino acid residue 482 (H482R) of SEQ ID NO: 2, a histidine to tyrosine substitution at amino acid residue 482 (H482Y) of SEQ ID NO: 2, a histidine to proline substitution at amino acid residue 482 (H482P) of SEQ ID NO: 2 and a glutamine to lysine substitution at amino acid residue 469 (Q469K) of SEQ ID NO: 2.

In other embodiments of the method, the increased amount of an expressed POI relative to the unmodified Gram positive control cell is at least 5%. In another embodiment, the increased amount of an expressed POI relative to the unmodified Gram positive control cell is at least 10%. In certain other embodiments, the Gram positive bacterial cell is a Bacillaceae family member. In another embodiment, the Gram positive bacterial cell is a *Bacillus* genus member. In yet another embodiment, the *Bacillus* is selected from *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii* and *B. thuringiensis*. In certain other embodiments, the *Bacillus* is *Bacillus subtilis* or *Bacillus licheniformis*. In other embodiments, the POI is encoded by a gene exogenous to the modified bacterial cell or a gene endogenous to the modified bacterial cell. In certain embodiments, the POI is secreted or transported extracellularly. In other embodiments, the POI secreted or transported extracellularly is isolated. In another embodiment, the isolated POI is purified.

In another embodiment, the POI is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Certain other embodiments of the disclosure are directed to an isolated protein of interest (POI) produced by the methods of the disclosure.

In another embodiment, the disclosure is directed to a method for obtaining a modified Gram positive bacterial cell expressing an increased amount of a POI comprising (a) introducing at least one rpoC gene modification into a parental Gram positive bacterial cell, and (b) selecting one or more daughter cells expressing an increased amount of the POI.

In certain other embodiments, the disclosure is directed to an integration vector comprising a modified rpoC gene comprising at least one mutation in the rpoC gene encoding a variant RNA-polymerase (RNAP) β'-subunit polypeptide. In other embodiments, the disclosure is directed to such Gram positive bacterial cells comprising the integration plasmid.

In certain other embodiments, the disclosure is directed to a method for obtaining a transformed *Bacillus* host cell comprising (a) transforming an exogenous polynucleotide into a *Bacillus* host cell made competent by at least one copy of an introduced first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct, and (b) isolating a transformant of the *Bacillus* host cell comprising the exogenous polynucleotide. In certain embodiments, the competent *Bacillus* host cell further comprises at least one copy of an introduced second nucleic acid construct comprising a promoter region 5' and operably linked to a polynucleotide encoding a ComK polypeptide to render the host cell even further competent. In certain other embodiments, the ComK polypeptide comprises 90% sequence identity to the ComK polypeptide of SEQ ID NO: 35 or SEQ ID NO: 37. In another embodiment, the *Bacillus* host cell is *Bacillus licheniformis*. Certain other embodiments of the disclosure are directed to transformed *Bacillus* host cell obtained from such methods.

In another embodiment, the disclosure is directed to a method of obtaining a competent *Bacillus* host cell comprising: (a) introducing into a non-competent *Bacillus* host cell at least one copy of a first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell, and (b) isolating a competent *Bacillus* host cell comprising the introduced polynucleotide of step (a). in certain embodiments, the competent *Bacillus* host cell further comprises at least one copy of an introduced second nucleic acid construct comprising a promoter region 5' and operably linked to a polynucleotide encoding a ComK polypeptide. In yet other embodiments, the ComK polypeptide comprises 90% sequence identity to the ComK polypeptide of SEQ ID NO: 35 or SEQ ID NO: 37. In another embodiment, the *Bacillus* host cell is *Bacillus licheniformis*.

Certain other embodiments of the disclosure are directed to competent *Bacillus* host cells obtained from such methods.

In certain other embodiments, the disclosure is directed to a competent *Bacillus* host cell comprising at least one copy of a first nucleic acid construct comprising a promoter region 5' and operably linked to a polynucleotide encoding a modified rpoC polypeptide comprising 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct.

In another embodiment, the disclosure is directed to a method for obtaining a transformed *Bacillus* host cell comprising: (a) transforming an exogenous polynucleotide into a *Bacillus* host cell made competent by at least one copy of an introduced first nucleic acid construct comprising a promoter region 5' and operably linked to a polynucleotide encoding a rpoB polypeptide, wherein the modified rpoB polypeptide comprises 90% sequence identity to SEQ ID NO: 4 and comprises a valine residue at position 478 of SEQ ID NO: 4, wherein the polynucleotide encoding the rpoB polypeptide is foreign to the *Bacillus* host cell that was non-competent prior to the introduction of the first nucleic acid construct, and (b) isolating a transformant of the *Bacillus* host cell comprising the exogenous polynucleotide.

In yet another embodiment, the disclosure is directed to a method of obtaining a competent *Bacillus* host cell comprising (a) introducing into a non-competent *Bacillus* host cell at least one copy of a first nucleic acid construct comprising a promoter region 5' and operably linked to a polynucleotide encoding a rpoB polypeptide, wherein the rpoB polypeptide comprises 90% sequence identity to SEQ ID NO: 4 and comprises a valine residue at position 478 of SEQ ID NO: 4, wherein the polynucleotide encoding the rpoB polypeptide is foreign to the *Bacillus* host cell, and (b) isolating a competent *Bacillus* host cell comprising the introduced polynucleotide of step (a).

Certain other embodiments of the disclosure are directed to transformed *Bacillus* host cells obtained from such methods.

BRIEF DESCRIPTION OF THE BIOLOGICAL SEQUENCES

Figure 1:
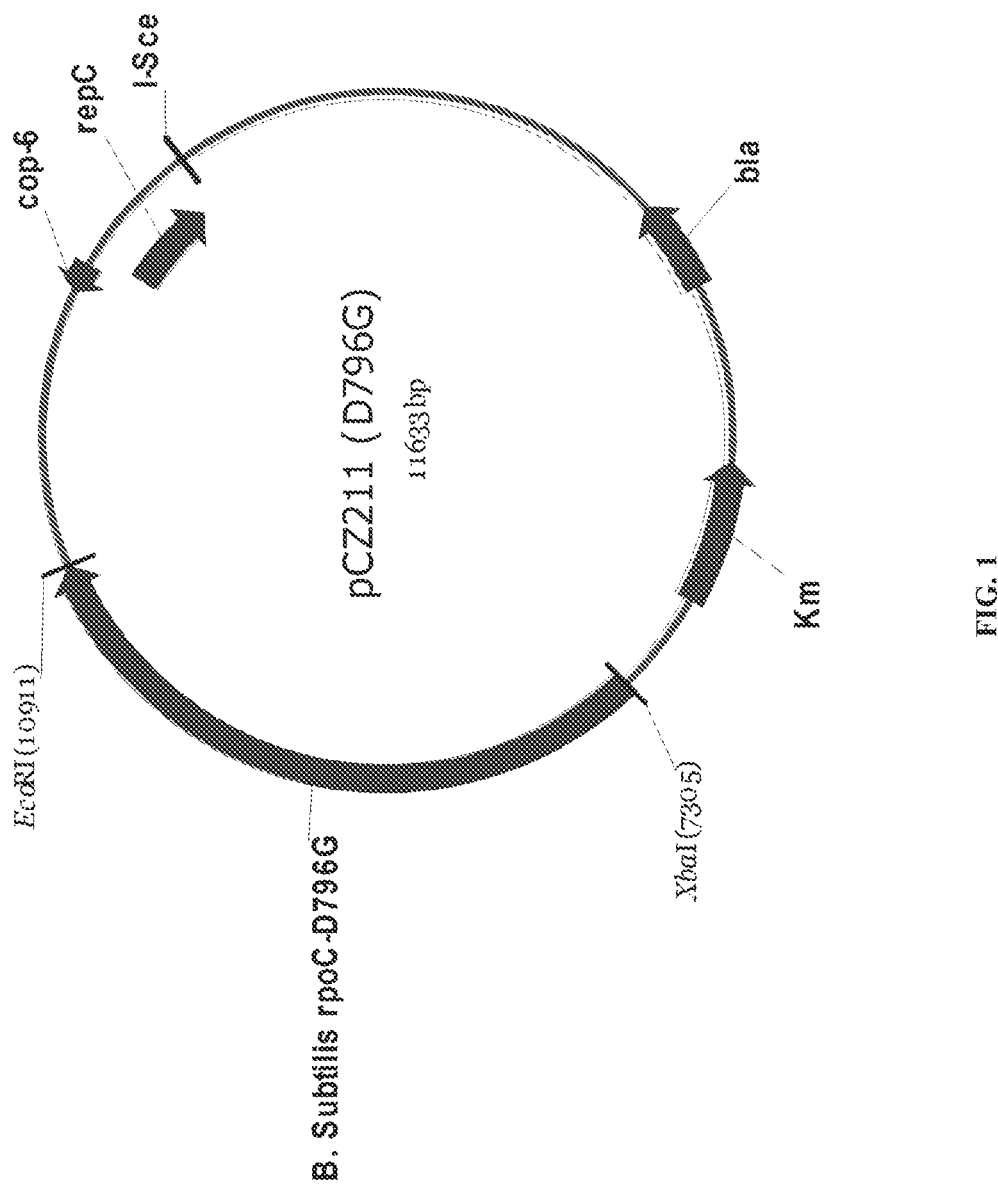
FIG. 1 shows a plasmid map of exemplary rpoC gene modifications (i.e., substitutions and deletion mutants) of the instant disclosure, which are set forth in Table 1. The specific amino acid substitutions or deletions set forth in Table 1, are relative to a parental *Bacillus subtilis* rpoC gene of SEQ ID NO: 5, which encodes a wild-type RpoC (β'-subunit) protein of SEQ ID NO: 6. For example, the map of the pCZ211 plasmid set forth in FIG. 1 encodes a modified RpoC (β'-subunit) protein comprising an amino acid substitution of the aspartic acid (D) at amino acid residue 796 of SEQ ID NO: 6 with a glycine (G) residue (labeled "rpoC-D796G" in FIG. 1). The plasmid further comprises an "EcoRI" restriction site, an "XbaI" restriction site, an I-Sce site, a kanamycin ("Km") resistance gene, a β-lactamase ("bla") gene, a cop-6 and a gene encoding "repC" protein.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5 (a-bis), and Section 208 and Annex C of the Administrative Instructions. The symbols and format used for nucleotide and amino acid sequence data comply with the rules set forth in 37 C.F.R. § 1.822.

SEQ ID NO: 1 is a nucleic acid sequence encoding a wild-type RpoB (β-subunit) protein from *Bacillus subtilis*.

SEQ ID NO: 2 is the amino acid sequence of a wild-type RpoB (β-subunit) protein from *Bacillus subtilis*.

SEQ ID NO: 3 is a nucleic acid sequence encoding a wild-type RpoB (3-subunit) protein from *Bacillus licheniformis*.

SEQ ID NO: 4 is the amino acid sequence of a wild-type RpoB (β-subunit) protein from *Bacillus licheniformis*.

SEQ ID NO: 5 is a nucleic acid sequence encoding a wild-type RpoC (β'-subunit) protein from *Bacillus subtilis*.

SEQ ID NO: 6 is the amino acid sequence of a wild-type RpoC (β'-subunit) protein from *Bacillus subtilis*.

SEQ ID NO: 7 is a nucleic acid sequence encoding a wild-type RpoC (β'-subunit) protein from *Bacillus licheniformis*.

SEQ ID NO: 8 is the amino acid sequence of a wild-type RpoB (β'-subunit) protein from *Bacillus licheniformis*.

SEQ ID NO: 9 is a "I-SceI-1" oligonucleotide sequence used in constructing the temperature sensitive plasmid pKSV7-I-Sce KM.

SEQ ID NO: 10 is a "I-SceI-2" oligonucleotide sequence used in constructing the temperature sensitive plasmid pKSV7-I-Sce KM.

SED ID NO: 11 is a forward "EcoRI-rpoC" primer nucleic acid sequence.

SED ID NO: 12 is a reverse "SalI-rpoC" primer nucleic acid sequence.

SEQ ID NO: 13 is a forward primer nucleic acid sequence used for colony PCR to confirm successful assembly of plasmids pCZ201-pCZ205.

SEQ ID NO: 14 is a reverse primer nucleic acid sequence used for colony PCR to confirm successful assembly of plasmids pCZ201-pCZ205.

SEQ ID NO: 15 is a forward "rpoC" primer nucleic acid sequence.

SEQ ID NO: 16 is a reverse "rpoC" primer nucleic acid sequence.

SEQ ID NO: 17 is a forward "rpoC" primer nucleic acid sequence used for sequencing confirmation.

SEQ ID NO: 18 is a forward "NotI-Amylase-3" primer nucleic acid sequence used to obtain the Amylase-3 integration cassette.

SEQ ID NO: 19 is a reverse "NotI-Amylase-3" primer nucleic acid sequence used to obtain the Amylase-3 integration cassette.

SEQ ID NO: 20 is an oligonucleotide used to amplify the 5' sequence of the rpoB gene.

SEQ ID NO: 21 is an oligonucleotide used to amplify the 5' sequence of the rpoB gene.

SEQ ID NO: 22 is an oligonucleotide used to amplify the 3' sequence of the rpoB gene.

SEQ ID NO: 23 is an oligonucleotide used to amplify the 3' sequence of the rpoB gene.

SEQ ID NO: 24 is an oligonucleotide used to amplify the 3' sequence of the rpoB gene.

SEQ ID NO: 25 is an oligonucleotide used to amplify the 5' sequence of the rpoB gene.

SEQ ID NO: 26 is an oligonucleotide used to amplify the 3' sequence of the rpoB gene.

SEQ ID NO: 27 is an oligonucleotide used to amplify the 5' sequence of the rpoB gene.

SEQ ID NO: 28 is a synthetic DNA construct comprising a spectinomycin resistance gene and a recognition site for an I-Sce restriction enzyme.

SEQ ID NO: 29 is an oligonucleotide used to amplify the 3' sequence of the rpoB gene.

SEQ ID NO: 30 is an oligonucleotide used to amplify the 3' sequence of the rpoB gene.

SEQ ID NO: 31 comprises amino acid residues 461-500 of the RpoC protein of SEQ ID NO: 6.

SEQ ID NO: 32 is a forward EcoRI-RpoB primer nucleic acid sequence.

SEQ ID NO: 33 is a reverse NotI-RpoB primer nucleic acid sequence.

SEQ ID NO: 34 is a nucleic acid sequence encoding a *Bacillus* ComK polypeptide.

SEQ ID NO: 35 is the amino acid sequence of the ComK polypeptide encoded by SEQ ID NO: 34.

SEQ ID NO: 36 is an alternative nucleic acid sequence encoding a *Bacillus* ComK polypeptide.

SEQ ID NO: 37 is the amino acid sequence of the ComK polypeptide encoded by SEQ ID NO: 36.

DETAILED DESCRIPTION

The present disclosure is generally related to modified Gram positive bacterial cells producing increased amounts of one or more protein(s) of interest. Thus, certain embodiments of the instant disclosure are directed to modified Gram positive bacterial cells expressing an increased amount of a protein of interest (hereinafter, a "POI"), relative to an unmodified (parental) Gram positive bacterial cell expressing the same POI, wherein the modified bacterial cell comprises at least one mutation in a rpoC gene encoding a variant RNA-polymerase (RNAP) β'-subunit polypeptide.

I. Definitions

In view of the modified bacterial cells, compositions thereof and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited in this specification are herein incorporated by reference.

It is further noted that the claims may be drafted to exclude any optional element. As such, this statement is intended to serve as antecedent basis for use of such exclusive terminology as "solely," "only", "excluding" and the like, in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Where a range of values are provided, it is understood that each intervening value, to the tenth of the unit of the lower limit (unless the context clearly dictates otherwise), between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about". The term "about" is used herein to provide literal support for the exact number that it precedes, as well as a number that is near to or approximately the number that the term precedes.

As defined herein, a "modified cell", an "altered cell", a "modified bacterial cell", an "altered bacterial cell", a "modified host cell", or an "altered host cell" may be used interchangeably and refer to recombinant Gram positive bacterial (host) cells that comprise at least one mutation in a rpoC gene encoding a variant RNA-polymerase (RNAP) β'-subunit polypeptide. For example, a "modified" Gram positive bacterial cell of the instant disclosure may be further defined as a "modified (host) cell" which is derived from a parental bacterial cell, wherein the modified (daughter) cell comprises at least one mutation in a rpoC gene encoding a variant RNAP β'-subunit polypeptide.

As defined herein, an "unmodified cell", an "unaltered cell", an "unmodified bacterial cell", an "unaltered bacterial cell", an "unmodified host cell", or an "unaltered host cell" may be used interchangeably and refer to "unmodified" (parental) Gram positive bacterial cells that do not comprise the at least one mutation in a rpoC gene encoding a variant RNAP β'-subunit polypeptide.

In certain embodiments, the "unmodified" Gram positive (parental) cell may be referred to as a "control cell", particularly when being compared with, or relative to, a "modified" Gram positive (daughter) cell. As used herein, when the expression and/or production of a POI in an "unmodified" (parental) cell (i.e., a control cell) is being compared to the expression and/or production of the same POI in a "modified" (daughter) cell, it will be understood that the "modified" and "unmodified" cells are grown/cultured/fermented under essentially the same conditions (e.g., the same conditions such as media, temperature, pH and the like).

Likewise, as defined herein, the terms "increased expression", "enhanced expression", "increased expression of a POI", "increased production", "increased production of a POI" and the like refer to a "modified" (daughter) cell comprising at least one mutation in a rpoC gene encoding a variant RNAP β'-subunit polypeptide, wherein the "increase" is always relative (vis-à-vis) to an "unmodified" (parental) cell expressing the same POI.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids". Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated region (UTR), and 3'-UTR, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a bacterial cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNAtechniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed.

As used herein, "transformation" refers to introducing an exogenous DNA into a Gram positive host cell so that the DNA is maintained as a chromosomal integrant or a self-replicating extra-chromosomal vector.

As defined herein, the term "competence" is a natural physiological state in which exogenous DNA can be internalized into a *Bacillus* sp. host cell, leading to a transformation event. The term "competence" is distinct from "artificial transformation" which involves electroporation, protoplasts, heat shock and CaCl$_2$ treatment.

As defined herein, the terms "non-competent", "poorly transformable" and "low transformability" are used interchangeably herein, wherein these terms mean that the number of transformants per microgram (µg) of DNA is less than twice the spontaneous mutation frequency when using the methods for competence-mediated transformation in *B. subtilis* or *B. licheniformis*.

As used herein, the term "ComK" polypeptide is defined as the product of the comK gene, a transcription factor that acts as the final auto-regulatory control switch prior to competence development. The ComK polypeptide (i.e., transcription factor) is involved with activation of the expression of late competence genes involved in DNA-binding, uptake and recombination.

As defined herein, a host cell "genome", a bacterial (host) cell "genome", or a Gram positive bacterial (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "transformation cassette" refers to a specific vector comprising a foreign gene, and having elements in addition to the foreign gene that facilitate transformation of a particular host cell.

An "expression cassette" refers to a specific vector comprising a foreign gene, and having elements in addition to the foreign gene that allow for "increased" expression of the foreign (heterologous) gene in a host cell.

Many prokaryotic and eukaryotic expression vectors are commercially available and well known in the art. Selection of appropriate expression vectors is within the knowledge of those having skill in the art.

As used herein, the term "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism.

An "expression vector" refers to a vector that has the ability to incorporate and express heterologous DNA in a foreign cell. Many prokaryotic and eukaryotic expression vectors are commercially available.

A "targeting vector" is a vector that includes polynucleotide sequences that are homologus to a region in the chromosome of a host cell into which it is transformed and that can drive homologous recombination at that region. Targetting vectors find use in introducing mutations into the chromosome of a cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a modified Gram positive bacterial cell (e.g., a "host" cell), wherein the POI is expressed at increased levels (i.e., relative to an unmodified (parental) Gram positive bacterial cell). Thus, as used herein, a POI may be an enzyme, a substrate-binding protein, a surface-active protein, a structural protein, a receptor protein, or the like.

Similarly, as defined herein, a "gene of interest" or "GOI" refers a nucleic acid sequence (e.g., a polynucleotide, a gene or an open reading frame) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids.

The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. Foreign (heterologous) genes comprise native genes (or ORFs) inserted into a non-native organism and/or chimeric genes inserted into a native or non-native organism.

As used herein, the term "expression" refers to the transcription and stable accumulation of sense (mRNA) or anti-sense RNA, derived from a nucleic acid molecule of the invention. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As defined herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

As used herein, a "parental" cell refers to any cell or strain of microorganism in which the genome of the "parental" cell is modified (e.g., one or more mutations introduced into the parental cell) to generate a modified "daughter" cell.

The term "derived" encompasses the terms "originated" "obtained," "obtainable," and "created," and generally indicates that one specified material or composition finds its origin in another specified material or composition, or has features that can be described with reference to the another specified material or composition.

As used herein, "increasing" protein production is meant an increased amount of protein produced. The protein may be produced inside the host cell, or secreted (or transported) into the culture medium. In certain embodiments, the protein of interest is produced into the culture medium.

Increased protein production may be detected for example, as higher maximal level of protein or enzymatic activity, such as protease activity, amylase activity, cellulase activity, hemicellulase activity and the like, or total extracellular protein produced as compared to the parent host. As defined herein, a bacterial RNAP "core enzyme" is comprised of a (alpha), 3 (beta), and β' (beta') subunits in a 2:1:1 ratio, respectively. The RNAP α (alpha), 3 (beta), and β' (beta') subunit polypeptides are encoded by the rpoA, rpoB, and rpoC genes, respectively. Thus, as used herein, the term "β-subunit" or "β-subunit polypeptide" means a RpoB polypeptide encoded by an rpoB gene; and the term "β'-subunit" or "β'-subunit polypeptide" means the RpoC polypeptide encoded by the rpoC gene. As used herein, the term "β'-subunit family member" refers to any prokaryotic RNAP composed of three subunits a, 3, and β' in the above mentioned 2:1:1 ratio, and wherein the amino acid sequence of the β'-subunit comprises a forty (40) amino acid contiguous sequence that can be aligned with the sequence of the RpoC (β'-subunit) protein from position 461 to 500 of SEQ ID NO: 6 or SEQ ID NO: 8 and result in at least 75% homology.

As used herein, the term "equivalent positions" means the amino acid residue positions after alignment with the RpoC (β'-subunit) polypeptide sequence from amino acid residues 461 to 500 of SEQ ID NO: 6 or SEQ ID NO: 8. The forty (40) contiguous amino acids residues (i.e., equivalent positions) described above for SEQ ID NO: 6 (i.e., residues 461 to 500 of SEQ ID NO: 6) and SEQ ID NO: 8 (i.e., residues 461-500 of SEQ ID NO: 8), are presented in the amino acid sequence of SEQ ID NO: 38.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wis., USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

II. RNA-Polymerase

As stated briefly above, transcription in all cellular organisms is driven by a multi-subunit, DNA-dependent RNA-polymerase (RNAP), with a conserved crab claw-like shape that embraces the template DNA (see, Cramer, 2002). The RNAP core enzyme is composed of α(alpha), β (beta), and β' (beta prime) subunits in a 2:1:1 ratio, individually encoded for by the rpoA, rpoB, and rpoC genes, respectively. The holoenzyme usually comprises sigma and omega subunits. The sigma subunit is responsible for promoter recognition and binding.

Gram positive bacteria have an additional δ (delta) subunit that has been reported to enhance transcriptional specificity by blocking RNAP binding at weak promoter sites (Juang & Helmann, 1994; Lopez de Saro et al., 1995). The holoenzyme RNAP forms an open complex by melting the DNA near the transcription start site, and then begins to synthesize RNA. The sigma factor is released and the core enzyme completes synthesis of the mRNA (Borukhov & Severinov, 2002; de Haseth & Helmann, 1995). The core RNAP is highly conserved in sequence and structure, spanning from species of bacteria to humans, particularly among the large-subunits (i.e., the bacterial p and β' subunits) homologs (Lane & Darst, 2010). Four structurally conserved modules, known as the β' jaw, p' clamp, 3 lobes, and β flap, play a crucial role in proper accommodation of the RNAP and DNA (Chakraborty et al., 2012).

III. Bacterial (Host) Cells and Methods of Use

In certain embodiments, the present disclosure is related to modified Gram positive bacterial cells producing increased amounts of one or more protein(s) of interest. Thus, certain embodiments of the instant disclosure are directed to modified Gram positive bacterial cells expressing an increased amount of a POI, relative to an unmodified (parental) Gram positive bacterial cell expressing the same POI, wherein the modified bacterial cell comprises at least one mutation in a rpoC gene encoding a variant RNA-polymerase (RNAP) β'-subunit polypeptide. In other embodiments, the disclosure is directed to Gram positive bacterial host cells made competent by introducing into the host cells an expression construct comprising a promoter region operably linked to a polynucleotide encoding a variant rpoC polypeptide.

Thus, in certain embodiments, the disclosure pertains to methods of modifying bacterial cells such that the modified (daughter) cells produce an increased level of a protein of interest. In other embodiments, the disclosure pertains to a protein of interest produced by fermenting a modified (variant) bacterial cell of the instant disclosure. Certain other embodiments of the disclosure are directed to one or more proteinaceous compositions comprising one or more protein of interest(s) thus made. In yet other embodiments, the present disclosure pertains to methods of producing one or more protein(s) of interest employing modified (mutant) bacterial cells set forth herein, as well as to methods of producing and using one or more proteinaceous compositions comprising one or more protein(s) of interest.

In certain embodiments, the present disclosure is directed to modified Gram positive bacterial cells producing increased levels of one or more protein(s) of interest, as compared (vis-à-vis) to unmodified (parental) cells, wherein the one or more modified cells comprise at least one mutation in the β'-subunit of an RNAP (subunit) encoded by the rpoC gene. In certain other embodiments, the present disclosure provides modified bacterial cells producing an increased level of one or more protein(s) of interest, as compared (vis-à-vis) to an unmodified (parental) cell, wherein the modified cell comprises (a) at least one mutation in the β'-subunit of an RNAP encoded by the rpoC gene and (b) at least one mutation in the β-subunit of an RNAP (subunit) encoded by the rpoB gene.

IV. Modified (Host) Cells Comprising a Mutation in the RpoC (β'-Subunit) of RNAP In some embodiments, the at least one mutation in the β'-subunit of RNAP can be any type of mutation, and can be a single mutation, or a set of multiple mutations, including, for example, replacements, insertions, deletions, transpositions, terminations (stop codons introduced), point mutations, and the like.

Mutations can be a single base pair substitution, which is the substitution of a single nucleotide base with a different nucleotide base at the same position, with the corresponding substitution of the complementary base on the other strand of the DNA. Single base pair substitutions are conceivable and indeed contemplated to be within the scope of the invention. The mutations can appear in protein coding regions, or in regions that encode ribosomal or transfer RNAs.

The mutations of the disclosure can be prepared employing any mutagenesis procedure known in the art, including, for example, site-directed mutagenesis, synthetic gene construction, semi-synthetic gene construction, random mutagenesis, shuffling, and the like.

Site-directed mutagenesis is a technique in which one or more (for example, several) mutations are introduced at one or more defined sites in a polynucleotide encoding the gene at issue. Site-directed mutagenesis can be accomplished in vitro by PCR, which employs primers containing the desired mutation. Site-directed mutagenesis can also be performed in vitro by cassette mutagenesis, involving first cleaving by a restriction enzyme at a designated site in the plasmid encoding the gene at issue, and thereafter ligating an oligonucleotide fragment containing the desired mutation at the cleavage site. In a typical embodiment, the same restriction enzyme is used to digest or cleave the plasmid at the designated site and prepare the oligonucleotide fragment containing the mutation, thus permitting sticky ends of the plasmid and the fragment to ligate to one another (See, e.g., Scherer and Davis, 1979 and Barton et al., 1990).

Site-directed mutagenesis can also be accomplished in vivo employing methods known in the art. See, e.g., U.S. Patent Application Publication No. 2004/0171154; Storici et al., 2001; Kren et al., 1998 and Calissano and Macino, 1996. Any site-directed mutagenesis procedure can be suitable for use with the present invention. To that end, there are a number of commercial kits available that can be used to prepare variants.

Random mutagenesis can be accomplished through many known means. One of such well-known methods is chemical mutagenesis by outgrowth in the presence of a mutagenizing reagent such as 2-aminopurine (2AP), N-methyl-N'-nitro-N-nitrosoguanidine (MNNG), or ethyl methane sulfonate (EMS), among others. Detailed discussion of methods for chemical mutagenesis as suitable herein and known in the art can be found in Miller (Cold Spring Harbor Laboratory Press, Plainview, N.Y. 1992).

Mutagenesis may also be accomplished by expressing a mutator gene, such as mutD5, off of a plasmid as described by Selifonova et al., 2001.

Cellular genomes can be manipulated through transposon mutagenesis, genome shuffling, overexpression of genes from a plasmid, or other cellular engineering techniques (Kleckner et al., 1991; Patnaik, 2008). Mutant cells can also be produced by simply outgrowing cells and allowing replication errors to naturally occur, as in the method of U.S. Pat. No. 6,361,966.

In order to obtain increasingly improved mutants, two (2) or more rounds of mutagenesis can suitably be performed, and during each round, the same or different methods of mutagenesis may be employed.

In some embodiments, the β'-subunit of the RNAP encoded by the rpoC gene is a naturally-occurring variant of a *Bacillus* β'-subunit, which has at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity to an amino acid sequence of SEQ ID NO: 6 or SEQ ID NO: 8.

In certain embodiments, the β'-subunit of the RNAP is obtained from a different bacterial cell, and has at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity to an amino acid sequence of SEQ ID NO: 6 or SEQ ID NO: 8.

V. Modified (Host) Cells Producing an Increased Level of A Protein of Interest

To confirm that a modified Gram positive bacterial cell produces an increased level of a POI, various methods of screening can be applied. For instance, an expression vector may encode a polypeptide fusion to the target protein and serves as a detectable label, or alternatively, the target protein itself may serve as the selectable or screenable marker. The labeled protein can also be detected using Western blotting, dot blotting (detailed descriptions of such methods are available at the website of the Cold Spring Harbor Protocols), ELISA, or, if the label is a GFP, whole cell fluorescence or FACS.

For example, a 6-histidine tag can be included to make a fusion to the target protein, and Western blots can be used to detect such a tag. Moreover, if the target protein expresses at sufficiently high levels, SDS-PAGE combined with Coomassie/silver staining, may be performed to adequately detect increases in mutant expression over wild type; and in such a case, no labeling of any molecules would be necessary.

In other embodiments, the expression of the POI in a modified (host) cell versus an unmodified (parental) cell is correlated with mRNA transcript levels. For example, certain embodiments are related to the molecular characterization of a gene or ORF encoding a POI, which usually includes a thorough analysis of the temporal and spatial distribution of RNA expression. A number of widely used procedures exist and are known in the art for detecting and determining the abundance of a particular mRNA in a total or poly(A) RNA sample. Non-limiting examples include such methods as Northern blot analysis, nuclease protection assays (NPA), in situ hybridization, and reverse transcription-polymerase chain reaction (RT-PCR).

Other methods can be employed to confirm the improved level of a protein of interest, including, for example, the detection of the increase of protein activity or amount per cell, protein activity or amount per milliliter of medium, allowing cultures or fermentations to continue efficiently for longer periods of time, or through a combination of these methods The detection of specific productivity is another suitable method for evaluating protein production. Specific productivity (Qp) can be determined using the following equation:

$$Qp = gP/gDCW \cdot hr$$

wherein, "gP" is grams of protein produced in the tank; "gDCW" is grams of dry cell weight (DCW) in the tank and "hr" is fermentation time in hours from the time of inoculation, which includes the time of production as well as growth time.

In certain embodiments, a modified bacterial cell of the disclosure produces at least about, at least about 5%, at least about 6%, at least about 7%, at least about 8%, at least about 9%, or at least about 10% or more of a POI, as compared to its unmodified (parental) cell.

VI. Modified (Host) Cells Made Competent by Introducing A Polynucleotide Encoding a Modified RpoC Polypeptide Certain embodiments of the disclosure are directed to non-competent Gram positive host cells. More particularly, certain embodiments of the disclosure are directed to non-competent Gram positive host cells (e.g., a *Bacillus* sp. host cell) made competent by the introduction of a nucleic acid construct comprising a promoter operably linked to a polynucleotide encoding a modified rpoC polypeptide. In certain embodiments, the non-competent host cell(s) made competent by the "introduced" nucleic acid construct is a *Bacillus* cell selected from *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii* and *B. thuringiensis*.

For example, in certain embodiments, the disclosure is directed to a method for obtaining a transformed *Bacillus* host cell comprising (a) transforming an exogenous polynucleotide into a *Bacillus* host cell made competent by at least one copy of an introduced first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct, and (b) isolating a transformant of the *Bacillus* host cell comprising the exogenous polynucleotide. In certain embodiments, the competent *Bacillus* host cell set forth above further comprises at least one copy of an introduced second nucleic acid construct comprising a promoter region 5' and operably linked to a polynucleotide encoding a ComK polypeptide to render the host cell even further competent. In particular embodiments, the ComK polypeptide comprises at least 75%, 80%, 90%, 95% sequence identity to the ComK polypeptide of SEQ ID NO: 35 or SEQ ID NO: 37. In one particular embodiment, the host cell is *Bacillus licheniformis*. In other embodiments, the disclosure provides a transformed *Bacillus* host cell obtained from such methods.

In other embodiments, the disclosure is directed to a method of obtaining a competent *Bacillus* host cell comprising (a) introducing into a non-competent *Bacillus* host cell at least one copy of a first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell, and (b) isolating a competent *Bacillus* host cell comprising the introduced polynucleotide of step (a). In certain other embodiments, the competent *Bacillus* host cell further comprises at least one copy of an introduced second nucleic acid construct comprising a promoter region 5' and operably linked to a polynucleotide encoding a ComK polypeptide. In certain embodiments, the ComK polypeptide comprises between about 75% to 100% sequence identity to the ComK polypeptide of SEQ ID NO: 35 or SEQ ID NO: 37. In another embodiment, the host cell is *Bacillus licheniformis*. In another embodiment, the disclosure is directed to competent *Bacillus* host cell(s) obtained from such methods.

In certain other embodiments, the disclosure provides competent *Bacillus* host cells comprising at least one copy of a first nucleic acid construct comprising a promoter region 5' and operably linked to a polynucleotide encoding a modified rpoC polypeptide comprising 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct.

VII. Bacterial Cells

In certain embodiments, a modified bacterial cell of the disclosure is a Bacillaceae family member. In other embodiments, a modified bacterial cell of the disclosure is a member of the *Bacillus* genus. In certain embodiments, a modified bacterial cell of the disclosure is a *Bacillus* cell selected from *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii* and *B. thuringiensis*. In other embodiments, the *Bacillus* cell is *Bacillus subtilis* or *Bacillus licheniformis*.

It is recognized in the art that the genus *Bacillus* continues to undergo taxonomical reorganization. Thus, it is intended that the genus include species that have been reclassified, including, but not limited to, such organisms as *B. stearothermophilus*, which is now named "*Geobacillus stearothermophilus*", or *B. polymyxa*, which is now "*Paenibacillus polymyxa*".

VIII. Culturing Modified Cells for Production of a Protein of Interest

In other embodiments, the present disclosure provides methods for increasing the protein productivity of a modified bacterial cell, as compared (i.e., relative) to an unmodified (parental) cell. More particularly, in certain embodiments, methods for increasing the protein productivity of a modified bacterial cell comprises culturing the modified bacterial cells under suitable fermentation conditions, wherein the modified cell comprises at least one mutation in the β'-subunit of the RNAP as encoded by the rpoC gene.

Thus, host cells and transformed cells can be cultured in conventional nutrient media. The culture media for transformed host cells may be modified as appropriate for activating promoters and selecting transformants. The specific culture conditions, such as temperature, pH and the like, may be those that are used for the host cell selected for expression, and will be apparent to those skilled in the art. In addition, culture conditions may be found in the scientific literature such as Sambrook (1982; 2001), Harwood et al. (1990) and from the American Type Culture Collection (ATCC).

IX. Transformation

A polynucleotide construct comprising a nucleic acid encoding a POI can be constructed such that it is expressed by a host cell. Because of the known degeneracies in the genetic code, different polynucleotides encoding an identical amino acid sequence can be designed and made with routine skills in the art. For example, codon optimizations can be applied to optimize production in a particular host cell.

Nucleic acids encoding proteins of interest can be incorporated into a vector, wherein the vector can be transferred into a host cell using well-known transformation techniques, such as those disclosed herein. Likewise, in certain embodiments, a nucleic acid construct comprising a promoter region operably linked to a polynucleotide encoding a modified rpoC polypeptide can be incorporated into a vector, wherein the vector can be transferred into a host cell using well-known transformation techniques. In other embodiments, a nucleic acid construct comprising a promoter region operably linked to a polynucleotide encoding a ComK polypeptide can be incorporated into a vector, wherein the vector can be transferred into a host cell using well-known transformation technique.

The vector may be any vector that can be transformed into and replicated within a host cell (e.g., a *Bacillus* sp. host cell). For example, a vector comprising a nucleic acid encoding a POI can be transformed and replicated in a bacterial host cell as a means of propagating and amplifying the vector. The vector also may be transformed into an expression host, so that the protein encoding nucleic acids (i.e., ORFs) can be expressed as a functional protein. Bacterial cells that serve as expression hosts (i.e, a modified bacterial "host" cell) include members of the Bacillaceae family and members of the *Bacillus* genus.

A representative vector which can be modified with routine skill to comprise and express a nucleic acid encoding a POI is vector p2JM103BBI (see, Vogtentanz, 2007).

A polynucleotide encoding a POI can be operably linked to a suitable promoter, which allows transcription in the host cell. The promoter may be any nucleic acid sequence that shows transcriptional activity in the host cell of choice and may be derived from genes encoding proteins either homologous or heterologous to the host cell.

Examples of suitable promoters for directing the transcription of the polynucleotide sequence encoding a POI, especially in a bacterial host, include the promoter of the lac operon of *E. coli*, the *Streptomyces coelicolor* agarase gene dagA or celA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes, and the like.

In certain embodiments, a promoter for directing the transcription of the polynucleotide sequence encoding a POI is a wild-type aprE promoter, a mutant aprE promoter or a consensus aprE promoter set forth in PCT International Publication WO2001/51643.

In other embodiments, a promoter for directing the transcription of the polynucleotide sequence encoding a POI is a ribosomal promoter such as a ribosomal RNA promoter or a ribosomal protein promoter. More particularly, in certain embodiments, the ribosomal RNA promoter is a rrn promoter derived from *B. subtilis*, more particularly, the rrn promoter is a rrnB, rrnI or rrnE ribosomal promoter from *B. subtilis*. In certain embodiments, the ribosomal RNA promoter is a P2 rrnI promoter from *B. subtilis* set forth in PCT International Publication No. WO2013/086219.

The POI coding sequence can be operably linked to a signal sequence. The nucleic acid sequence encoding the signal sequence may be the DNA sequence naturally associated with the GOI (encoding the POI) to be expressed, or may be from a different genus or species. A signal sequence and a promoter sequence comprising a polynucleotide construct or vector can be introduced into a bacterial host cell, and those sequences may be derived from the same source or different sources. For example, in certain embodiments, the signal sequence is an arpE signal sequence (see, e.g., Vogtentanz et al., 2007; Wang et al., 1988) that is operably linked to an arpE promoter set forth in PCT International Publication WO2001/51643.

An expression vector may also comprise a suitable transcription terminator and, in eukaryotes, certain polyadenylation sequences operably linked to the DNA sequence encoding the protein of interest. Termination and polyadenylation sequences may suitably be derived from the same sources as the promoter, but in other embodiments, the termination and polyadenylation sequences may well be derived from different sources as each other and/or as the promoter.

A suitable vector may further comprise a nucleic acid sequence enabling the vector to replicate in the host cell. Examples of such enabling sequences include the origins of replication of plasmids pUC19, pACYC177, pUB110, pE194, pAMB1, pIJ702, and the like.

A suitable vector may also comprise a selectable marker, e.g., a gene the product of which complements a defect in the isolated host cell, such as the dal genes from *B. subtilis* or *B. licheniformis*; or a gene that confers antibiotic resistance such as, e.g., ampicillin resistance, kanamycin resistance, chloramphenicol resistance, tetracycline resistance and the like.

A suitable expression vector typically includes components of a cloning vector, such as, for example, an element that permits autonomous replication of the vector in the selected host organism and one or more phenotypically detectable markers for selection purposes. Expression vectors typically also comprise control nucleotide sequences such as, for example, promoter, operator, ribosome binding site, translation initiation signal and optionally, a repressor gene, one or more activator genes sequences, or the like.

Additionally, a suitable expression vector may further comprise a sequence coding for an amino acid sequence capable of targeting the protein of interest to a host cell organelle such as a peroxisome, or to a particular host cell compartment. Such a targeting sequence may be, for example, the amino acid sequence "SKL". For expression under the direction of control sequences, the nucleic acid sequence of the protein of interest can be operably linked to the control sequences in a suitable manner such that the expression takes place.

Protocols, such as described herein, used to ligate the DNA construct encoding a protein of interest, promoters, terminators and/or other elements, and to insert them into suitable vectors containing the information necessary for replication, are well known to persons skilled in the art (see, e.g., Sambrook et al., 1989, and 3rd edition 2001).

An isolated cell, either comprising a polynucleotide construct or an expression vector, is advantageously used as a host cell in the recombinant production of a POI. The cell may be transformed with the DNA construct encoding the POI, conveniently by integrating the construct (in one or more copies) into the host chromosome. Integration is generally deemed an advantage, as the DNA sequence thus introduced is more likely to be stably maintained in the cell. Integration of the DNA constructs into the host chromosome may be performed applying conventional methods, for example, by homologous or heterologous recombination. Alternatively, the cell may be transformed with an expression vector as described above in connection with the different types of host cells.

It is, in other embodiments, advantageous to delete genes from expression hosts, where the gene deficiency can be cured by an expression vector. Known methods may be used to obtain a bacterial host cell having one or more inactivated genes. Gene inactivation may be accomplished by complete or partial deletion, by insertional inactivation or by any other means that renders a gene nonfunctional for its intended purpose, such that the gene is prevented from expression of a functional protein.

Techniques for transformation of bacteria and culturing the bacteria are standard and well known in the art. They can be used to transform the improved hosts of the present invention for the production of recombinant proteins of interest. Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; gene gun or biolistic transformation and protoplast fusion, and the like. Transformation and expression methods for bacteria are also disclosed in Brigidi et al. (1990). A preferred general transformation and expression protocol for protease deleted *Bacillus* strains is provided in Ferrari et al. (U.S. Pat. No. 5,264,366).

As stated briefly above, certain embodiments of the disclosure are directed to methods for obtaining a transformed *Bacillus* host cell comprising (a) transforming an exogenous polynucleotide into a *Bacillus* host cell made competent by at least one copy of an introduced first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell that was non-competent prior to the introduction of the first nucleic acid construct, and (b) isolating a transformant of the *Bacillus* host cell comprising the exogenous polynucleotide. In other embodiments, the competent *Bacillus* host cell further comprises at least one copy of an introduced second nucleic acid construct comprising a promoter region 5' and operably linked to a polynucleotide encoding a ComK polypeptide to render the host cell even further competent. In certain embodiments the ComK polypeptide comprises about 75-100% sequence identity to the ComK polypeptide of SEQ ID NO: 35 or SEQ ID NO: 37. In another embodiment, the disclosure is directed to transformed *Bacillus* host cells obtained by such methods.

In certain other embodiments, the disclosure provides a method of obtaining a competent *Bacillus* host cell comprising (a) introducing into a "non-competent" *Bacillus* host cell at least one copy of a first nucleic acid construct comprising a promoter region 5' and operably linked to a polynucleotide encoding a modified rpoC polypeptide, wherein the modified rpoC polypeptide comprises 90% sequence identity to SEQ ID NO: 8 and an aspartic acid to glycine substitution at position 796 of SEQ ID NO: 8, wherein the polynucleotide encoding the rpoC polypeptide is foreign to the *Bacillus* host cell, and (b) isolating a competent *Bacillus* host cell comprising the introduced polynucleotide. In certain embodiments, the competent *Bacillus* host cell further comprises at least one copy of an introduced second nucleic acid construct comprising a promoter region 5' and operably linked to a polynucleotide encoding a ComK polypeptide. In certain embodiments, the ComK polypeptide comprises about 75-100% sequence identity to the ComK polypeptide of SEQ ID NO: 35 or SEQ ID NO: 37. In certain embodiments, the *Bacillus* host cell is *Bacillus licheniformis*. In another embodiment, the disclosure is directed to a competent *Bacillus* host cell obtained from such methods.

For example, as set forth below in Example 9, the modified *Bacillus* host cells of the disclosure comprising at least one copy of an introduced first nucleic acid construct comprising a promoter region operably linked to a polynucleotide encoding a modified rpoC polypeptide comprising 90% sequence identity to SEQ ID NO: 8 and comprising an aspartic acid to glycine substitution at position 796 (i.e., a D796G substitution relative to SEQ ID NO: 8) demonstrate a significant increase in the number of transformants obtained (i.e., relative to parental (control) *Bacillus* host cells which do not comprise the introduced first nucleic acid construct). Thus, in certain embodiments, a modified *Bacillus* host cell comprising the introduced first nucleic acid construct (i.e., encoding a modified rpoC polypeptide comprising 90% sequence identity to SEQ ID NO: 8 and comprising an aspartic acid (D) to glycine (G) substitution at position 796) increases the number of transformants by at least 2-fold relative to an unmodified (control) "non-competent" parental *Bacillus* host cell.

X. Fermentation

In certain embodiments, the instant disclosure is directed to methods of producing a POI comprising fermenting a modified bacterial cell, wherein the modified cell secrets the POI into the culture medium. Fermentation methods well known in the art can be applied to ferment the modified and unmodified bacterial cells.

In some embodiments, the bacterial cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

This, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification the proteinaceous components of the supernatant or filtrate are precipitated by means of a salt, e.g., ammonium sulphate. The precipitated proteins are then solubilized and may be purified by a variety of chromatographic procedures, e.g., ion exchange chromatography, gel filtration.

XI. Proteins of Interest Produced by Modified (Host) Cells

In another embodiment, the present disclosure provides methods for producing increased levels of a POI comprising obtaining a modified Gram positive bacterial cell expressing an increased amount of a POI, wherein the modified bacterial cell comprises at least one mutation in a rpoC gene encoding a variant RNA-polymerase (RNAP) β'-subunit polypeptide, and culturing the modified cell under conditions such that the POI is expressed, wherein the modified bacterial cell expressing an increased amount of a POI is relative to the expression of the POI in an unmodified Gram positive bacterial cell.

The POI can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

The POI or variant POI may also be a peptide, a peptide hormone, a growth factor, a clotting factor, a chemokine, a cytokine, a lymphokine, an antibody, a receptos, an adhesion molecule, a microbial antigen (e.g., HBV surface antigen, HPV E7, etc.), and variants thereof or fragments thereof.

Other types of proteins (or variants) of interest may be those that are capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

XII. Use of the Proteinaceous Compositions

In another embodiment, the present disclosure provides a proteinaceous composition comprising one or more protein(s) of interest. The proteinaceous composition is suitably produced using the methods provided herein. The proteinaceous composition comprises a protein of interest, encoded by a gene of interest, expressed using a method described herein. The composition may be used in various useful industrial applications such as, for example, in biomass hydrolysis, cleaning applications, grain processing, animal nutrition, food composition, textile treatment, personal care products and the like.

For example, a proteinaceous composition thus produced can be used in cleaning application. Enzymatic cleaning components are popular because of their ability to break down soils, stains, and other debris that are otherwise not readily removed by conventional chemical detergents. Well-known enzymes useful for cleaning include proteases and amylases, with other enzymes such as lipases, pectinases, mannanases, even certain cellulases, each providing a set of different functionalities. Proteases combat protein-based stains; amylases work on carbohydrates and starches; and lipases break down lipids or fats, for example. The disclosure provides modified bacterial cells, which have demonstrated improved protein production, suitable and advantageous as a producer of industrial enzymes, variants, and mixtures of interest to such use in cleaning applications.

In another example, the proteinaceous composition thus made can be used in grain procession. Starch is the most common storage carbohydrate in plants, used by the plants themselves as well as by microbes and by higher organisms. A great variety of enzymes are able to catalyze starch hydrolysis. Starch from all plant sources occurs in the form of granules, but depending on the species of the plant source, starch presents in markedly different size and physical characteristics. Acid hydrolysis of starch had widespread use in the past, however this process has now largely been replaced by enzymatic processes, which are known to demand less corrosion-resistant materials and other benefits, need less energy for heating and are relatively easier to control than the acid process. The disclosure provides an engineered, transformed, or derived eubacterial cell, which has demonstrated improved protein production, suitable and advantageous as a producer of industrial enzymes, variants, and mixtures of interest to such use in starch degradation and grain processing.

In another example, the proteinaceous composition thus made can be used in food application. Enzymes produced by bacteria, yeasts and moulds have been used in food application to make foods such as bread, cheese, beer and wine for many thousands of years. Today enzymes are used in bakery, cheese making, starch processing and production of fruit juices and other drinks, providing various benefits such improved texture, appearance and nutritional value, generate desirable flavors and aromas, and the like. Food enzymes typically originate in animals and plants (for example, a starch-digesting enzyme, amylase, can be obtained from germinating barley seeds) as well as from a range of beneficial microorganisms. Enzymes are deemed viable and desirable alternatives to traditional chemical-based technology, replacing synthetic chemicals in many processes. Enzymes can help improve the environmental performance of food production processes, reducing energy consumption and improving biodegradability of waste or side products. Enzymes tend to be more specific in their actions than synthetic chemicals, and as such, enzymatic processes tend to give fewer side reactions and waste or byproducts, and consequently producing higher quality products and reducing the likelihood of pollution. Enzymatic processes are often also the only processes possible. An example of this is in the production of clear apple juice concentrate, which relies on the use of the enzyme, pectinase. Most of the food enzymes are produced from microorganisms such *Bacillus, Aspergillus, Streptomyces* or *Kluyveromyces*. The disclosure provides an engineered, transformed, or derived eubacterial cell, which has demonstrated improved protein production, suitable and advantageous as a producer of industrial enzymes, variants, and mixtures of interest to such use in food applications.

In another example, the proteinaceous composition thus made can be used in animal feed additive. Cellulase, xylanase, β-glucanase, protein of interest, protease, lipase, phytase and other carbohydrase have been widely used in animal feed industry. Since many plant based feeds contain substances with anti-nutritional factors that reduce animal growth, the enzymes added to such feeds improve digestibility of these anti-nutritional factors by degrading fibres, proteins, starches and phytates, rendering them more digestible by the animals, and enabling the use of cheaper and often locally produced feeds, while maximizing meat, egg or milk productivity. At the same time, the enzymes added to such feeds also may provide benefits supporting gut health and enhanced animal performance. The disclosure provides an engineered, transformed, or derived eubacterial cell, which has demonstrated improved protein production, suitable and advantageous as a producer of industrial enzymes, variants, and mixtures of interest to such use in animal feed applications.

In yet a further example, the proteinaceous composition thus made can be used in textile applications. Enzymes have become an integral part of the textile processing. There are two well-established enzyme applications in the textile industry. First, enzymes such as amylases are commonly used in the preparatory finishing area for desizing. Second, enzymes such as cellulases are commonly used in the finishing area for softening, bio-stoning and reducing of pilling propensity of cotton goods.

Other enzymes such as, for example, pectinases, lipases, proteases, catalases, xylanases etc., are also used in textile processing. Moreover, there are various applications which entail enzymes included fading of denim and non-denim, bio-scouring, bio-polishing, wool finishing, peroxide removal, decolourization of dyestuff, etc. Thus, in certain embodiments the disclosure provides modified Gram positive bacterial cells (which are demonstrated herein as having improved protein production) as a producer of industrial enzymes, variants, and mixtures of interest to such use in textiles applications.

EXAMPLES

Aspects of the present bacterial cells, compositions and methods thereof may be further understood in light of the following examples, which should not be construed as limiting. Modifications to materials and methods will be apparent to those skilled in the art.

Example 1

Modified *B. subtilis* Cells Comprising Mutations in the RpoC Gene

In the present Example, the production of protease and amylase enzymes are tested in modified *Bacillus subtilis* cells comprising one (1) of five (5) different rpoC mutated genes, and compared to unmodified (parental) *B. subtilis* cells comprising a wild type *Bacillus subtilis* rpoC gene (SEQ ID NO: 6). A total of five (5) different rpoC gene alterations (e.g., substitutions and deletions) are designed, constructed and tested. The five rpoC gene alterations are listed below in Table 1.

TABLE 1

INTEGRATION PLASMIDS COMPRISING MODIFIED rpoC GENES ENCODING MODIFIED (MUTANT) RNAP β'-SUBUNIT PROTEINS

| Plasmid | β' Mutation | Gene |
|---|---|---|
| pCZ211 | D796G | rpoC |
| pCZ212 | M751I | rpoC |
| pCZ213 | R784H | rpoC |
| pCZ214 | S797F | rpoC |
| pCZ215 | ΔI1018-R1020 | rpoC |

Nucleotide substitutions or deletions are designed to achieve the amino acid alterations in the RpoC (β'-subunit) protein set forth above in Table 1 (e.g., see SEQ ID NO: 5, which encodes wild-type RpoC (β'-subunit) protein of SEQ ID NO: 6).

For example, the methionine (M) to isoleucine (I) substitution at amino acid position 751 (hereinafter, "M751I") of SEQ ID NO: 6 is made by replacing the ATG codon at nucleotides 2251, 2252 and 2253 of SEQ ID NO: 5 with an ATC, ATT or ATA codon therefor; the arginine (R) to histidine (H) substitution at amino acid position 784 (hereinafter, "R784H") of SEQ ID NO: 6 is made by replacing the CGT codon at nucleotides 2350, 2351 and 2352 of SEQ ID NO: 5 with a CAT or CAC codon therefor; the serine (S) to phenylalanine (F) substitution at amino acid position 797 (hereinafter, "S797F") of SEQ ID NO: 6 is made by replacing the TCA codon at nucleotides 2389, 2390 and 2391 of SEQ ID NO: 5 with a TTT or TTC codon therefor; and the aspartic acid (D) to glycine (G) substitution at amino acid position 796 (hereinafter, "D796G") of SEQ ID NO: 6 is made by replacing the GAC codon at nucleotides 2386, 2387 and 2388 of SEQ ID NO: 5 with a GGC, GGT, GGA or GGG codon therefor. The three (3) amino acid deletion construct (hereinafter, "ΔI1018-R1020") set forth above in Table 1 is made by deleting codons of SEQ ID NO: 5, which correspond to isoleucine (I), serine (S) and arginine (R) amino acids of the RpoC (β'-subunit) protein at residues 1018, 1019 and 1020 of SEQ ID NO: 6, respectively.

Construction of the Integration Plasmids.

As stated briefly above, a total of five integration plasmids (Table 1), named pCZ211 (e.g., see FIG. 1), pCZ212 pCZ213, pCZ214 and pCZ215, are constructed as described herein. The five modified rpoC genes are either synthesized by SGI-DNA (La Jolla, Calif.) or generated by site-mutagenesis and cloned into the temperature sensitive plasmid pKSV7-1-Sce using restriction digestion and ligation. The ligation mixture is transformed into *E. coli* Top10 cells and plated on LA plates containing 50 µg/ml of carbenicillin. Colonies were screened by colony PCR and sequencing.

Construction of the Temperature Sensitive Plasmid.

The temperature sensitive integration plasmid pKSV7-1-Sce, referenced in the paragraph above, is constructed as follows: twenty (20) picomoles of two (2) single-strand oligomers, I-SceI-1: cgatTAGGGATAACAGGGTAATat (SEQ ID NO: 9), and I-SceI-2: cgatATTACCCTGT-TATCCCTAat (SEQ ID NO: 10), wherein capital letters are a homologous sequence of I-SceI restriction enzyme site, are incubated at 98° C. for seven (7) minutes and then kept at 55° C. for five (5) minutes to anneal the oligomers. The annealed fragment is phosphorylated with T4 polynucleotide kinase (New England BioLabs; Ipswich, Mass.) and then ligated with the ClaI site of pKSV7 integration vector (Smith & Youngman, 1992). To eliminate the chloramphenicol-resistant gene present in pKSV7, the plasmid is digested with NcoI and MfeI and is blunt ended with T4 DNA polymerase (New England BioLabs; Ipswich, Mass.). The fragment containing repF and cop-6 is separated from the chloramphenicol resistance gene fragment by agarose gel electrophoresis, and purified with a gel extraction kit (Qiagen; Hilden Germany), then self-ligated to generate the pKS vector. The pKS vector is digested with the restriction endonuclease HindIII and ligated to the kanamacyn (Km) resistant gene derived from the plasmid pDG780 (Guerout-Fleury et al., 1995) after digestion with HindIII restriction endonuclease. The resulting plasmid is named "pKSV-I-Sce Km".

Transformation of Mutant rpoC Genes into *B. subtilis* Cells and rpoC Mutant Screening.

Each of the plasmids containing the mutated rpoC genes set forth in Table 1 are transformed into *B. subtilis* cells, wherein transformants are selected on LB plates containing 10 µg/ml of kanamycin at 30° C. Subsequently, colonies are picked and inoculated into 25 mL of LB in shake flask, and incubated at 30° C. for three (3) hours with shaking at 250 RPM.

For the integration of the plasmid into the chromosome of *B. subtilis*, the temperature is shifted to 37° C. and incubated overnight. The next day, serial dilutions are made to $10^{-6}$ and $10^{-7}$, and the culture is plated on LB plate and incubated at 37° C. overnight. The rpoC mutant clones are screened by colony PCR and sequencing.

Expression of Proteins of Interest in Modified *B. subtilis* Cells Comprising Modified (Mutant) rpoC Genes.

After the introduction of the rpoC mutations into *Bacillus subtilis* cells, the modified and unmodified *Bacillus subtilis* cells are transformed with expression cassettes encoding either one of two different protease enzymes or one of two different amylase enzymes.

The two protease enzymes encoded by the expression cassettes are (1) a *B. lentus* variant protease set forth and described in U.S. Pat. No. 5,972,682, which is referred to herein as "Protease-1" and (2) a *B. clausii* variant protease set forth and described in PCT International Publication No. WO2010/056635, which is referred to herein as "Protease-2".

Likewise, the two amylase enzymes encoded by the expression cassettes are (1) a *Paenibacillus curdanolyticus* amylase variant set forth and described in PCT International Application Publication No. WO2014/164777; which is referred to herein as "Amylase-1" and (2) a wild-type or variant of a *Bacillus subtilis* amylase set forth and described in PCT International Application Publication Nos. WO2009/149419 and WO2009/149395; which is referred to herein as "Amylase-2". The production of each enzyme in the modified and unmodified *Bacillus subtilis* cells are tested in shake flasks and compared to the unmodified (parental) *Bacillus subtilis* cells.

Example 2

Modified *B. licheniformis* Cells Comprising Mutations in the RpoC Gene

In this example, the production of an amylase enzyme was tested in modified *Bacillus licheniformis* cells comprising one of five (5) different rpoC mutated (modified) genes, and compared with the unmodified (parental) *B. licheniformis* cells comprising the wild-type *B. licheniformis* rpoC gene (SEQ ID NO: 7). The five rpoC gene alterations are listed below in Table 2.

TABLE 2

INTEGRATION PLASMIDS COMPRISING MODIFIED rpoC GENES
ENCODING MODIFIED (MUTANT) RNAP β'-SUBUNIT PROTEINS

| Plasmid | β' Mutation | Gene |
|---|---|---|
| pCZ201 | D796G | rpoC |
| pCZ202 | ΔI1018-R1020 | rpoC |
| pCZ203 | M751I | rpoC |
| pCZ204 | R784H | rpoC |
| pCZ205 | S797F | rpoC |

Thus, in the present Example, nucleotide substitutions or deletions were designed to achieve the amino acid alterations in the RpoC (β'-subunit) protein set forth above in Table 2 (e.g., see SEQ ID NO: 7, which encodes the *B. licheniformis* wild-type RpoC (β'-subunit) protein of SEQ ID NO: 8).

For example, with reference to the wild-type rpoC nucleotide sequence set forth in SEQ ID NO: 7, the methionine (M) to isoleucine (I) substitution at amino acid position 751 (M751I) was made by replacing Guanine (G) with a Cytosine (C) at nucleotide position 2253 of SEQ ID NO: 7 (i.e., ATG to ATC); the arginine (R) to histidine (H) substitution at amino acid position 784 (R784H) was made by replacing Guanine with an Adenine (A) at nucleotide position 2351 of SEQ ID NO: 7 (i.e., CGT to CAT); the serine (S) to phenylalanine (F) substitution at amino acid position 797 (S797F) was made by replacing Cytosine-Adenine nucleotides (CA) with Thymine-Thymine nucleotides (TT) at nucleotide positions 2390 and 2391 of SEQ ID NO: 7 (i.e., TCA to TTT); the aspartic acid (D) to glycine (G) substitution at amino acid position 796 (D786G) was made by replacing Adenine (A) with a Guanine (G) at nucleotide position 2387 of SEQ ID NO: 7 (i.e., GAC to GGC). The three (3) amino acid deletion construct (ΔI1018-R1020) set forth above in Table 2 was made by deleting codons of SEQ ID NO: 7, which correspond to isoleucine (I), serine (S) and arginine (R) amino acids of the RpoC (β'-subunit) protein at residues 1018, 1019 and 1020 of SEQ ID NO: 8, respectively.

Construction of the rpoC Integration Plasmids.

Figure 2:
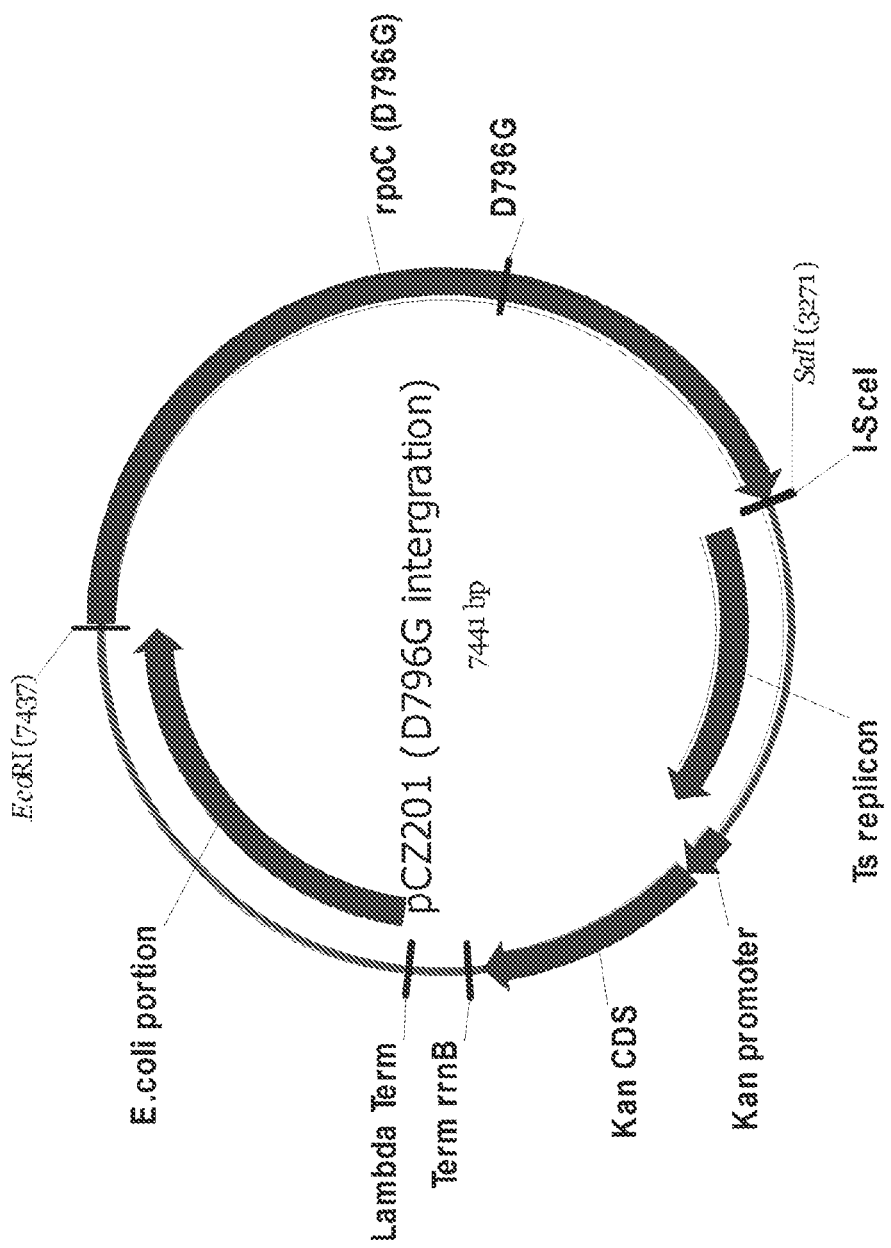
FIG. 2 shows the plasmid map of exemplary rpoC gene modifications (i.e., substitutions and deletion mutants) of the instant disclosure, which are set forth in Table 2. The specific amino acid substitutions or deletions set forth in Table 2, are relative to a parental *Bacillus licheniformis* rpoC gene of SEQ ID NO: 7, which encodes a wild-type RpoC (β'-subunit) protein of SEQ ID NO: 8. For example, the map of the pCZ201 plasmid set forth in FIG. 2 encodes a modified RpoC (β'-subunit) protein comprising an amino acid substitution of the aspartic acid (D) at amino acid residue 796 of SEQ ID NO: 8 with a glycine (G) residue. The plasmid further comprises an "EcoRI" restriction site, an "Sal-I" restriction site, an "l-Sce" site, a kanamycin resistance marker ("Kan CDS") coding sequence operably linked to a kanamycin promoter ("Kan promoter"), a "lamba terminator", a ribosomal rrnB terminator ("Term rrnB") and a pE194 temperature sentitive replicon ("Ts replicon").

As stated briefly above, a total of five integration plasmids (Table 2), named pCZ201 (e.g., see FIG. 2), pCZ202, pCZ203, pCZ204 and pCZ205 were constructed as described herein. Each of these plasmids (i.e., pCZ201-pCZ205) contains an *E. coli* origin of replication, a Kanamycin ("Km") selection marker, a PE194 temperature sensitive replicon ("Ts replicon") from *Staphylococcus aureuns*, and a rpoC gene with codon changes resulting in one of the five aforementioned amino acid alterations (Table 2).

Figure 3:
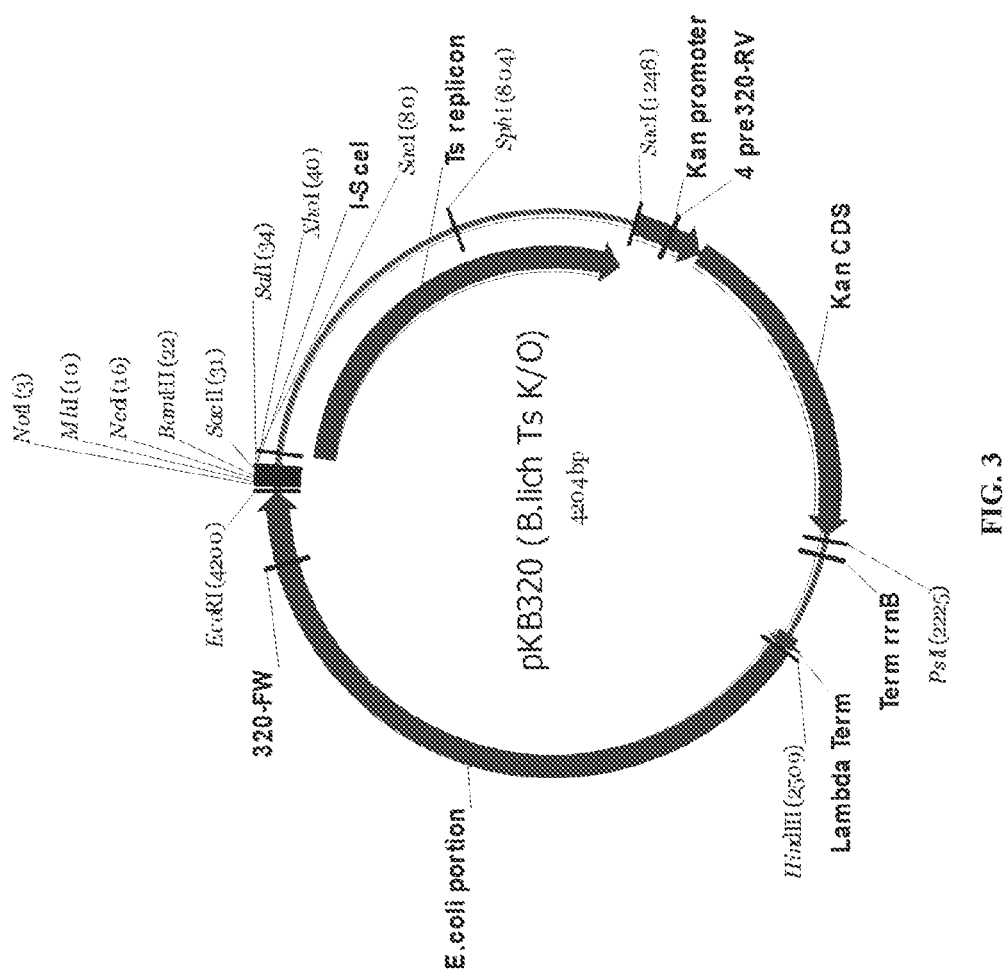
FIG. 3 shows a plasmid map of vector pKB320 described in Example 2. The pK320 plasmid, comprises various restriction enzyme sites, a pE194 temperature sensitive replicon (Ts replicon), a kanamycin coding sequence (Kan CDS), a kanamycin promoter (Kan promoter), a ribosomal terminator sequence (Term rrnB) and a lamba terminator (Lamba Term).

All five plasmids were derived from insertion of an approximately 3.2 kb synthetic (premade) vector pKB320 (see below and FIG. 3, pKB320 plasmid map) by using restriction digest and ligation methods. These five synthetically modified (mutated) rpoC genes presented in Table 2 were each individually inserted into a pUC02 vector by SGI-DNA (La Jolla, Calif.) and delivered as plasmid preparations. PCR was used to amplify each modified (mutated) rpoC fragment out of the plasmid and two restriction sites (i.e., EcoRI and SalI) were added at both ends by using primers:

```
EcoRI-rpoC-forward primer:
                              (SEQ ID NO: 11)
tcggaattccgagccgtatgggtcttgt;
and SalI-rpoC-reverse primer:
                              (SEQ ID NO: 12)
taagtcgacttattcagccggaaccatttc.
```

After successfully obtaining the PCR product, EcoRI and SalI restriction enzymes were used to digest both the PCR product, as well as pKB320 plasmid. Standard ligation with T4 ligase was then performed overnight at 16° C. The overnight ligation mixtures were then transformed into Top10 *E. Coli* competent cells and plated on LB plate with 10 ppm of Kanamycin selection and incubated at 37° C. for overnight.

After single *E. Coli* colonies formed on the plate, colony PCR was carried out using the following primers to confirm the successful assembly of all five plasmids:

```
Forward primer:
                              (SEQ ID NO: 13)
ctcgtgcacccaactgatcttcag
and;

Reverse primer:
                              (SEQ ID NO: 14)
ctgcgtccgttatcgatcaatgcgtc.
```

The successfully assembled (confirmed) clones were inoculated into LB liquid cultures and the plasmid DNA was extracted on the next day, using standard Mini-Prep procedure. The plasmid samples were sequenced and each confirmed to be correct.

Protoplast Transformation of rpoC Integration Plasmids into *B. licheniformis* Cells and rpoC Mutant Selection.

All five plasmids comprising the modified rpoC genes set forth in Table 2 were transformed into *B. licheniformis* cells using standard protoplast transformation (see, PCT International Publication No. WO2005/111203). The DNA and protoplasts mixture were plated on B. *Licheniformis* regeneration plate with 40 ppm of Neomycin as selection. After (3) three days of growth on regeneration plate, a sample from an individual transformant colony was picked and re-streaked on LB plate with 10 ppm of Neomycin.

The next day, a single colony was picked and inoculated into 25 mL of LB media in shake flask, shaken at 37° C., 250 rpm for three (3) hours. The temperature was then raised to 46° C. and the culture shaken overnight. The next day, each of the overnight cultures was diluted $10^6$ and $10^7$, and 100 μL was spread on to a LB plate and incubated at 30° C. overnight, until a single colony formed. The plates were then sent to Quintara Biosciences (Albany, Calif.) for colony PCR, as well as sequencing confirmation.

Two following two (2) primers were used for colony PCR:

```
rpoC forward primer:
                              (SEQ ID NO: 15)
cagctaaggatacgatccaaggcaag,
and rpoC reverse primer:
                              (SEQ ID NO: 16)
tcgctttatcttcgtcgatcagctc.
```

The following primer was used for sequencing:

```
rpoC forward primer:
                              (SEQ ID NO: 17)
ggcaagctgatgaaatccttggatg.
```

Amylase Expression in Modified *B. licheniformis* Cells.

To express an amylase enzyme in the modified *B. licheniformis* cells described above (i.e., the modified *B. licheniformis* cells transformed with one of the five rpoC mutants), an integration cassette expressing an amylase enzyme was prepared. The integration cassette comprises an amylase variant set forth and described in PCT International Publication No. WO2008/112459, which is referred to herein as "Amylase-3". To prepare the Amylase-3 integration cassette, the genomic DNA (gDNA) of *B. licheniformis* was extracted and used as template for PCR by using the following two (2) primers:

```
NotI-Amylase-forward:
                              (SEQ ID NO: 18)
tatgcggccgcatattccgcattcgcaatgcctac,
and NotI-Amylase-reverse:
                              (SEQ ID NO: 19)
tttgcggccgcaaaataaaaaaacggatttccttcagg.
```

One (1) ug of PCR product was then subjected to restriction digest with NotI enzyme and incubated at 37° C. for 4 hours. The fragments were then column purified, and ten (10) uL of such column purified fragments were then ligated by using five (5) units of T4 DNA ligase in a thirty (30) uL reaction and incubated at 16° C. overnight. The next day, five (5) uL of the overnight ligation mixture taken for rolling circle amplification (RCA), which was performed by mixing five (5) uL of overnight ligation mixture with five (5) uL of sample buffer and incubated at 96° C. for three (3) minutes, followed by the addition of five (5) uL of reaction buffer with 0.2 uL of enzyme mix, which was incubated for six (6) hours at 30° C.

For transformation, all of the RCA mixtures were added to one hundred fifty (150) µL of the modified *B. licheniformis* competent cells comprising the rpoC-D796G substitution and the modified *B. licheniformis* competent cells comprising the rpoC-M7511 substitution, and shaken in a glass tube for one hour at 37° C. The transformation mixtures (150 µL) were then plated on LB/1% insoluble starch plate with 10 ppm chloramphenicol and incubated at 37° C. overnight. A single halo positive transformant was selected and amplified in culture in increasing concentrations of chloramphenicol to the desired level of 75 ppm. Glycerol stocks of these two *B. licheniformis* strains (i.e., comprising the rpoC-D796G substitution or comprising the rpoC-M7511 substitution) were collected by mixing one (1) mL of overnight culture with five hundred (500) uL of 40% glycerol.

Example 3

Introduction of rpoB (β-Subunit) Substitution Mutants Q469K, Q469R or H482Y into the Modified *B. subtilis* Cells Three mutations in the rpoB gene encoding the RpoB (β-subunit) protein (i.e., mutations Q469K, Q469R and H482Y) have been identified from isolation and sequencing of *Bacillus subtilis* rifampicin resistant colonies (Ingham & Furneaux, 2000). The native (wild-type) *Bacillus subtilis* RpoB (β-subunit) protein sequence is set forth in SEQ ID NO: 2 and the nucleotide sequence encoding the native RpoB protein is set forth in SEQ ID NO: 1. To introduce the above mutations into the rpoB gene of *B. subtilis*, three constructs comprising the rpoB Q469K, Q469R or H482Y substitutions are made as follows.

The Q469K mutation is made by changing the CAA codon at nucleotide positions 1405, 1406 and 1407 of SEQ ID NO: 1 to an AAA codon. To introduce this mutation, the 5' sequence of rpoB gene is amplified with the oligonucleotides in SEQ ID NO: 20 and SEQ ID NO: 21; and the 3' part of the rpoB gene is amplified with the oligonucleotide in SEQ ID NO: 22 and SEQ ID NO: 23. The fusion PCR is performed using the oligonucleotides in SEQ ID NO: 20 and SEQ ID NO 33.

The Q469R mutation is made by changing the CAA codon at nucleotide positions 1405, 1406 and 1407 of SEQ ID NO: 1 to a CGA codon. To introduce this mutation, the 5' sequence of the rpoB gene is amplified with the oligonucleotide in SEQ ID NO: 20 and SEQ ID NO: 25; and the 3' sequence is amplified with the oligonucleotides in SEQ ID NO: 22 and SEQ ID NO: 24. The fusion PCR is performed using the oligonucleotides in SEQ ID NO: 20 and SEQ ID NO: 23.

The H482Y mutation is made by changing the CAC codon at nucleotide positions 1445, 1446 and 1447 of SEQ ID NO: 1 to a TAC codon. To introduce this mutation, the 5' sequence of the rpoB gene is amplified with the oligo- nucleotide in SEQ ID NO: 20 and SEQ ID NO: 27; and the 3' sequence is amplified with the oligonucleotides in SEQ ID NO: 23 and SEQ ID NO: 26. The fusion PCR is performed using the oligonucleotides in SEQ ID NO: 20 and SEQ ID NO 23.

The synthetic construct set forth in SEQ ID NO: 28, comprising a spectinomycin resistant ($Spc^R$) gene and the recognition sequence for the I-Sce restriction enzyme, is synthetically ordered as a g-Block from Integrated DNA Technologies (Coralville, Iowa).

The C-terminal portion of the rpoB gene is amplified using the oligonucleotides in SEQ ID NO: 29 and SEQ ID NO: 30.

Figure 4:
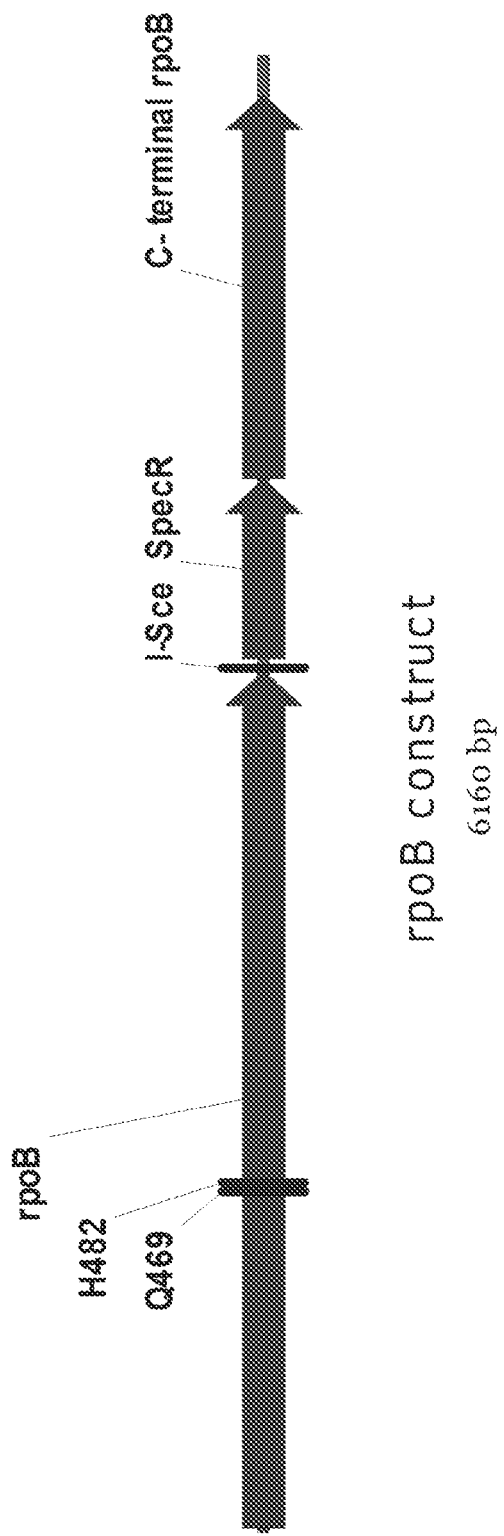
FIG. 4 is a schematic representation of the rpoB construct described in Example 3, wherein the rpoB construct comprises a spectinomycin (SpecR) resistance marker and a glutamine (Q) to arginine (R) substitution at amino acid position 469 of SEQ ID NO: 2 (i.e., a Q469R substitution), a glutamine (Q) to lysine (K) substitution at amino acid position 469 of SEQ ID NO: 2 (i.e., a Q469K substitution) or a histidine (H) to tyrosine (Y) substitution at amino acid position 482 of SEQ ID NO: 2 (i.e., a H482Y substitution).

The DNA fragment containing the rpoB mutation, the spectinomycin resistance marker and the partial rpoB sequence (see, FIG. 4) are assembled by fusion PCR using the oligonucleotides in SEQ ID NO: 20 and SEQ ID NO: 30.

Transformation of *Bacillus subtilis* Cells.

After purification, each of the above described constructs comprising the Q469R, Q469K or H482Y substitutions in rpoB are transformed in *B. subtilis* competent cells and positive transformants are selected on Luria agar plates containing 100 µg/ml of spectinomycin and re-isolated on Luria agar plates containing 200 µg/ml of rifampicin.

The plasmid pKBJ233, expressing the I-Sce restriction endonuclease (described in Janes & Stibitz, 2006), is transformed into the above cells. Positive colonies are selected on Luria agar plates containing 10 µg/ml of tetracycline. After re-isolation, the *B. subtilis* cells are grown in Luria broth containing 5 µg/ml of tetracycline for three (3) consecutive days, by inoculating in fresh media every twelve (12) hours, followed by single colony isolation.

The removal of the spectinomycin marker and the introduction of the selected mutations in the modified *B. subtilis* cells are confirmed by selecting for spectinomycin sensitive and rifampicin resistant colonies. The introduction of the mutation Q469K, Q469R or H482Y is then confirmed by DNA sequencing of the rpoBC operon.

Example 4

Effect of Mutations in the rpoB or RpoC Gene on Protease Expression in *Bacillus subtilis*

To test the effect of Protease-2 expression in the modified *B. subtilis* cells comprising mutations in the rpoB or rpoC genes, a Protease-2 expression construct is introduced in the aprE locus of the rpoB or rpoC modified *B. subtilis* cells.

The Protease-2 expression construct is amplified on Luria agar plates containing 25 µg/ml of chloramphenicol. The modified and wild-type *B. subtilis* cells are grown overnight in 5 mL of Luria broth. One (1) ml of pre-culture is used to inoculate 25 ml of 2×NB (2× Nutrient Broth, 1×SNB salts, described in PCT International Publication No. WO2010/14483) in shake flasks at 250 rpm to test protease expression. Cell densities of whole broth diluted 20× are measured at 600 nm at hourly intervals using a SpectraMax spectrophotometer (Molecular Devices, Downington, Pa.).

Protease-2 expression is monitored using N-suc-AAPF-pNA substrate (AAPF, from Sigma Chemical Co.) as described in PCT International Publication No. WO 2010/144283. Briefly, whole broth is diluted 40× in the assay buffer (100 mM Tris, 0.005% Tween 80, pH 8.6) and 10 µl of the diluted samples were arrayed in microtiter plates. The AAPF stock is diluted and the assay buffer (100× dilution of 100 mg/ml AAPF stock in DMSO) and 190 µl of this solution are added to the microtiter plates and the absorbance of the solution is measured at 405 nm using a SpectraMax spectrophotometer (Molecular Devices, Downington, Pa.).

Example 5

Effect of Mutations in the rpoB or rpoC Gene on Amylase Expression in *Bacillus subtilis*

To test the effect on expression of Amylase-2 in the modified *B. subtilis* cells comprising mutations in the rpoB or rpoC genes f, an expression construct is prepared which drives the expression of the Amylase-2 protein from the aprE promoter. The amylase expression construct, which includes a chloramphenicol acetyltransferase resistance (catR) marker gene is introduced into: (1) the aprE locus of the modified (daughter) *B. subtilis* cells comprising the modified rpoC gene, (2) the aprE locus of modified (daughter) *B. subtilis* cells comprising the modified rpoB gene, and (3) the aprE locus of the unmodified *B. subtilis* (parental) cells. The cells are amplified on Luria agar plates containing 25 µg/ml of chloramphenicol. The modified and unmodified cells are grown overnight in five (5) mL of Luria broth medium. One (1) ml of pre-culture is used to inoculate 25 ml of Luria broth medium in shake flasks at 37° C., 250 rpm to test the expression of the Amylase-2 protein. Cell densities are measured at 600 nm at hourly intervals using a SpectraMax spectrophotometer (Molecular Devices, Downington, Pa.).

The Amylase-2 protein activity of whole broth is measured using the Ceralpha reagent (Megazyme, Wicklow, Ireland.). The Ceralpha reagent mix from the Ceralpha HR kit is initially dissolved in 10 ml of MilliQ water, followed by the addition of 30 ml of 50 mM malate buffer, pH 5.6. The culture supernatants are diluted 40× in MilliQ water and 5 µl of diluted sample is added to 55 µL of diluted working substrate solution. The MTP plate is incubated for 4 minutes at room temperature after shaking. The reaction is quenched by adding 70 µl of 200 mM borate buffer pH 10.2 (stop solution). The absorbance of the solution is measured at 400 nm using a SpectraMax spectrophotometer (Molecular Devices, Downington, Pa.).

Example 6

Modified *B. licheniformis* Comprising a Modification in Both the rpoB and rpoC Gene To test the effects of mutations in both the rpoB gene and rpoC gene, a *Bacillus licheniformis* strain comprising a specific rpoB gene mutation (i.e., encoding a RpoB-A478V substitution) and a specific rpoC gene mutation (i.e., encoding a RpoC-D796G substitution) is prepared as described below.

The wild-type *B. licheniformis* RpoB (β-subunit) protein is set forth in SEQ ID NO: 4 and is encoded by the nucleotide sequence set forth as SEQ ID NO: 3. The wild-type *Bacillus licheniformis* RpoC (β'-subunit) protein is set forth in SEQ ID NO: 8 and is encoded by the nucleotide sequence set forth as SEQ ID NO: 7.

There are two alternative ways to introduce the desired rpoB and rpoC mutations into a *B. licheniformis* host cell, each of which are set forth below. For example, one methodology is to introduce the RpoC-D796G mutation into a modified *B. licheniformis* cell already comprising the RpoB-A478V substitution, or vice versa. These two approaches are described as Method 1 and Method 2 below.

Method 1: Integration Plasmid pCZ205 Construction.

Plasmid pCZ201 (e.g., see Example 2) comprises an *E. coli* origin of replication, a Kanamycin selection marker, a PE194 temperature sensitive replicon from *Staphylococcus aureus* and a rpoC gene with DNA sequence change (GAC to GGC at nucleotide sequence position 2062 of SEQ ID NO: 7), resulting in amino acid alteration (D796G).

The pCZ205 plasmid is made by insertion of an approximately 3.2 kb synthetically modified rpoC gene into vector pKB320 by using restriction digest and ligation method. This synthetically modified rpoC gene is inserted into a pUC02 vector by methods known in the art to generate a plasmid preparation. PCR is used to amplify the rpoC fragment out of the plasmid and to add two restriction sites EcoRI and SalI at both ends by using the primers:

```
EcoRI-rpoC FW:
                                (SEQ ID NO: 11)
tcggaattccgagccgtatgggtcttgt,
and SalI-rpoC RV:
                                (SEQ ID NO: 12)
taagtcgacttattcagccggaaccatttc.
```

After successfully obtaining the PCR product, both the PCR product as well as pKB320 plasmid are digested with EcoRI and SalI restriction enzymes, followed by the standard ligation with T4 ligase at 16° C. for overnight. The overnight ligation mixture is transformed into Top10 *E. coli* competent cells, plated on LB plate with 10 ppm of Kanamycin selection, and incubated at 37 C overnight. After single *E. coli* colonies forms on the plate, colony PCR is carried out with the following primers to confirm the successful assembly of the plasmid:

Forward primer:
(SEQ ID NO: 13)
ctcgtgcacccaactgatcttcag,
and

Reverse primer:
(SEQ ID NO: 14)
ctgcgtccgttatcgatcaatgcgtc.

The confirmed clone is inoculated into LB liquid culture and the plasmid DNA extracted on the next day by using standard Mini-Prep procedure. The plasmid samples are sent out for sequencing to confirm that correct plasmid is obtained.

Protoplast Transformation of Integration Plasmid pCZ205 into *B. licheniformis* Cells and rpoC Mutant Selection.

The pCZ205 plasmid is transformed into *B. licheniformis* cells using standard protoplast transformation (see, PCT International Publication No. WO2005/111203), and the DNA and protoplasts mixture are plated on *B. licheniformis* regeneration plate with 40 ppm of neomycin as selection. After three (3) days of growth on regeneration plate, individual transformants are picked and re-streaked on LB plate with 10 ppm of neomycin. On the next day, single colonies are picked and inoculated into 25 mL of LB media in shake flask, shaken at 37° C. and 250 rpm for three (3) hours, then the temperature shifted to 46° C. and shaking continued overnight. On the next day, a $10^6$ and $10^7$ fold dilution of the overnight culture is made and 100 μl spread on to a LB plate and incubated at 30° C. overnight, or until single colonies form. The presence of the correct mutation is confirmed by colony PCR and sequencing. The two primers used for colony PCR are:

rpoC Forward primer:
(SEQ ID NO: 15)
cagctaaggatacgatccaaggcaag
and rpoC Reverse primer:
(SEQ ID NO: 16)
tcgctttatcttcgtcgatcagctc.

The primer used for sequencing is:

rpoC Sequencing forward primer:
(SEQ ID NO: 17)
ggcaagctgatgaaatccttggatg.

Method 2: Integration Plasmid pCZ211 Construction.

Plasmid pCZ211 contains an *E. coli* origin of replication, a Kanamycin selection marker, a PE194 temperature sensitive replicon from *Staphylococcus aureus*, and rpoB gene with a mutation resulting in an alanine (A) to valine (V) substitution at amino acid position 478 ("A478V") of SEQ ID NO: 2.

Plasmid pCZ211 is made by the insertion of an approximately 3.5 kb modified rpoB gene (encoding the "A478V" substitution) into vector pKB320 by using restriction digest and ligation methods. To obtain the approximately 3.5 kb DNA fragment containing the rpoB gene (GCT to GTT at DNA sequence position 1433), PCR will be carried out by using the following two primers and *B. licheniformis* gDNA as template:

EcoRI-RpoB Forward primer:
(SEQ ID NO: 32)
CAAGAATTCTTGACAGGTCAACTAGTTCAGTATG
and NotI-RpoB Reverse primer:
(SEQ ID NO: 33)
GTAGCGGCCGCTACCCTGTCACTTGCGTATAAAATTC.

To insert this rpoB PCR product into pKB320 vector, both insert and vector are digested with EcoRI and NotI restriction enzymes, followed by standard ligation with T4 ligase at 16° C. for overnight. The overnight ligation mixture is then transformed into Top10 *E. coli* competent cells, plated on LB plate with 10 ppm of kanamycin selection, and incubated at 37° C. overnight. Single *E. coli* colonies are picked and inoculated into liquid culture, grown overnight and then the plasmid DNA is extracted using standard Mini-Prep procedure. The plasmid sample is then sent out for sequencing to confirm that pCZ211 plasmid is obtained.

Protoplast Transformation of Integration Plasmid pCZ211 into *B. licheniformis* Cells and rpoB Mutant Selection.

The pCZ211 plasmid is transformed into *B. licheniformis* cells by using standard protoplast transformation (see, PCT International Publication No. WO2005/111203), the DNA and protoplasts mixture are then plated on *B. licheniformis* regeneration plate with 40 ppm of neomycin as selection. After three days of growth on regeneration plates, individual transformants are picked and re-streaked on LB plate with 10 ppm of neomycin. On the next day, single colonies are picked and inoculated into 25 mL of LB media in shake flask, shaken at 37° C. and 250 rpm for three (3) hours, then the temperature is shifted to 46° C. and shaking continued overnight. The next day, $10^6$ and $10^7$ fold dilutions of the overnight cultures are made and 100 μl spread on to a LA plate and incubated at 30° C. overnight until a single colony formed. Single colonies are picked and patched onto LA plates without selection, LA plates+1 ppm Rifampicin, and LA plates+10 ppm Kanamycin. The positive clones or the ones with the rpoB-A478V substitution would be resistant to Rifampicin and sensitive to Kanamycin (due to loss of the pCZ111 plasmid).

Example 7

Shake Flask Production of Amylase Enzyme in Modified *B. licheniformis* Cells

In the present example, modified *Bacillus licheniformis* cells comprising the "rpoC-D796G" substitution described in Example 2 and wild-type (parental) *B. licheniformis* cells were transformed with a DNA cassette constructed from a number of synthetic DNA fragments. More particularly, DNA fragment 1 comprises a *B. licheniformis* adaA region, a cat promoter region, an alr1 gene, and a cat terminator region; ordered from Genescript (Piscataway, N.J.). DNA fragment 2 comprises a *B. subtilis* native rrnI P2 promoter region, a 5'-aprE UTR and a *B. licheniformis* lat Signal Sequence; prepared as double stranded gene fragments (e.g., G-blocks from IDT, Integrated DNA Technologies; Coralville, Iowa). DNA fragment 3 comprises an amylase gene sequence and a *B. licheniformis* lat terminator region. The DNA fragment 3 amylase gene is an amylase variant from *Cytophaga* sp. set forth and described in PCT International Publication No. WO2014/164777, which is referred to herein as "Amylase-4".

The 3 DNA fragments were fused by PCR, ligated by making use of 3' and 5' NotI restriction digestion sequences, then amplified by using the Illustra Templiphi kit (GE Healthcare) and finally transformed and integrated into the genome of the modified (rpoC-D796G) *B. licheniformis* cells and the wild-type (parental) *B. licheniformis* cells. Transformants were selected by making use of Heart Infusion (Bacto) agar plates, supplemented with 1% Starch Azure (Potato starch covalently linked with Remazol Brilliant Blue R; Sigma-Aldrich, S7629), and 300 mg/l of 13-Chloro-D-alanine (CDA) (Chem-Impex International Inc., Wood Dale, Ill.).

A clearing zone, indicative of amylolytic activity, was clearly visible around the colonies that have the Amylase-4 expression cassette integrated.

CDA (300 mg/l) resistant transformants secrete Amylase-4 as judged by halo formation on RBB-starch plates. Production of the Amylase-4 enzyme by the *B. licheniformis* cells was experimented by growing the cells in shake flasks, using a MOPS base medium MBD medium was made essentially as known in the art (see, Neidhardt et al., 1974), except that $NH_4Cl_2$, $FeSO_4$, and $CaCl_2$ were omitted from the base medium, 3 mM $K_2HPO_4$ was used, and the base medium was supplemented with 60 mM urea, 75 g/L glucose, and 1% soytone.

The micronutrients were made up as a 100× stock solution in one liter, 400 mg $FeSO_4$ $7H_2O$, 100 mg $MnSO_4$ $H_2O$, 100 mg $ZnSO_4$ $7H_2O$, 50 mg $CuCl_2$ $2H_2O$, 100 mg $CoCl_2$ $6H_2O$, 100 mg $NaMoO_4$ $2H_2O$, 100 mg $Na_2B_4O_7$ $10H_2O$, 10 ml of 1M $CaCl_2$, and 10 ml of 0.5 M sodium citrate. $CaCl_2$ was added to 5 mM and pH was adjusted to 6.8. After 64 hours of growth in an Infors incubator (35° C., 280 rpm), Amylase-4 enzyme concentration in whole cell broth was determined using the α-Amylase Ceralpha Assay Kit (Megazyme, Wicklow, Ireland).

The Ceralpha α-amylase assay involves incubating of whole culture broth with a substrate mixture under defined conditions, and the reaction is terminated (and color developed) by the addition of a base solution. The substrate is a mixture of the defined oligosaccharide "nonreducing-end blocked p-nitrophenyl maltoheptaoside" (BPNPG7 substrate) and excess levels of glucoamylase and β-glucosidase (which have no action on the native substrate due to the presence of the "blocking group"). Upon hydrolysis of the oligosaccharide by endo-acting α-amylase (or C6 amylase), the excess quantities of α-glucosidase and glucoamylase present in the mixture give instantaneous and quantitative hydrolysis of the p-nitrophenyl maltosaccharide fragment to glucose and free p-nitrophenol. The absorbance at 405 nm is measured, and this relates directly to the level of amylase in the sample analysed.

The equipment used for this set of assays includes a Biomek FX Robot (Beckman Coulter); a SpectraMAX MTP Reader (type 340-Molecular Devices) and iEMS incubator/shaker (Thermo Scientific). In this assay system, the reagent and solutions used are: (1) p-nitrophenyl maltoheptaoside (BPNPG7) substrate (Megazyme Ceralpha kit); (2) Dilution buffer: 50 mM MOPS, 0.1 mM $CaCl_2$), 0.005% TWEEN® 80 buffer, pH 7.15; and (3) 200 mM Boric acid/NaOH buffer, pH 10.2 (STOP buffer).

Figures 5, 5A:
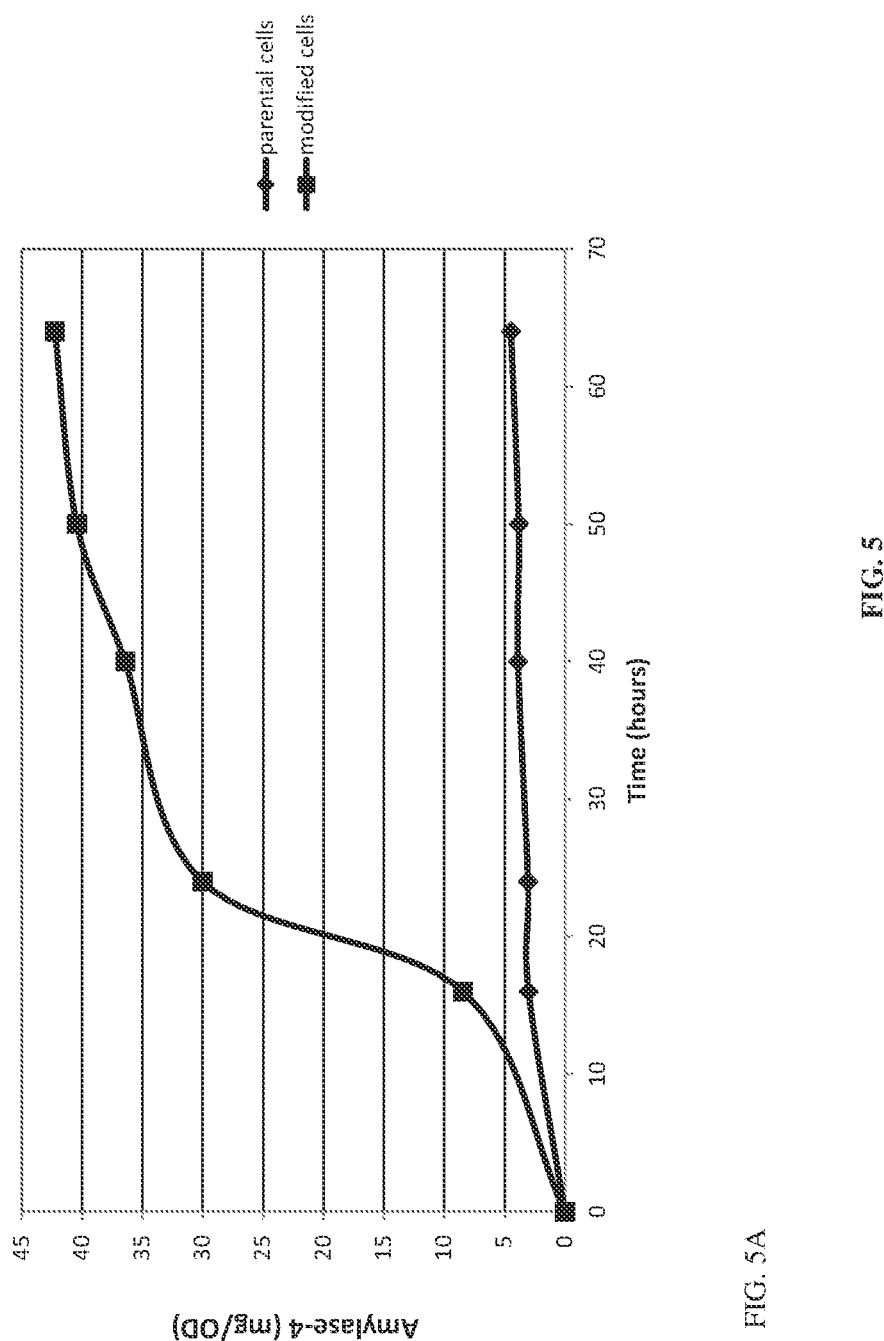
FIG. 5 presents data showing Amylase-4 enzyme production (as a function of time) described in Example 7. The data shown in FIG. 5 compare Amylase-4 enzyme production per OD (FIG. 5A) or per unit volume (FIG. 5B) in parental (wild-type) *B. licheniformis* cells relative to Amylase-4 production in modified (daughter) *B. licheniformis* cells comprising the rpoC gene variant (i.e., encoding the RpoC (β'-subunit) "D796G" polypeptide variant).
Figures 5, 5B:
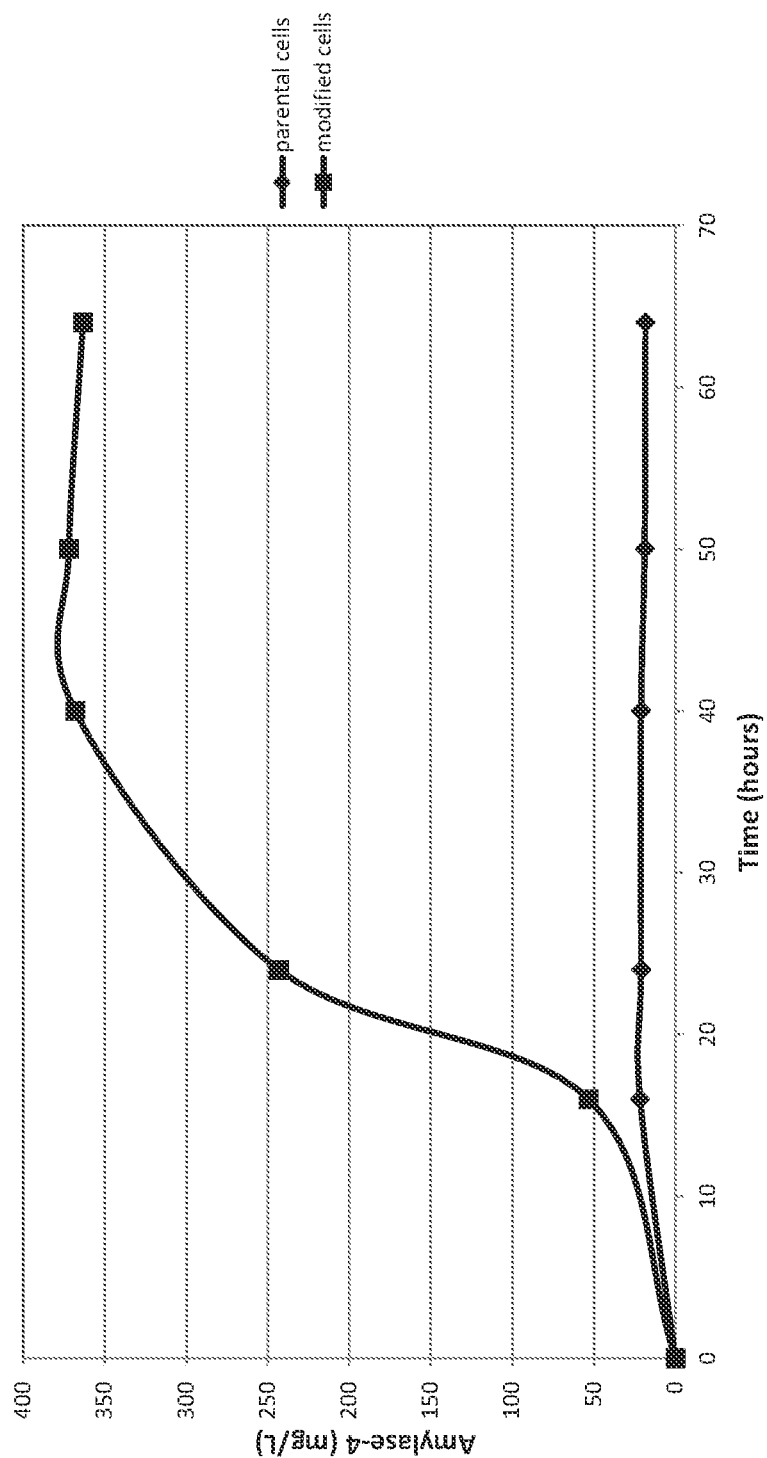

A vial containing 54.5 mg BPNPG7 substrate was dissolved in 10 ml of milliQ water. The amylase samples (whole cell broth) were diluted 1600× with dilution buffer. The assay was performed by adding 25 µl of diluted amylase solution into the wells of a MTP followed by the addition of 35 µl of 5.45 mg/ml BPNPG7 substrate solution. The solutions were mixed and the MTP is sealed with a plate seal and placed in an incubator/shaker (iEMS-Thermo Scientific) for 8 minutes at 25° C. The reaction was terminated by adding 100 µl STOP buffer and the absorbance was read at 405 nm in an MTP-Reader. A non-enzyme control was used to correct for background absorbance values. To calculate the Amylase-4 enzyme concentration (mg/l), a dilution series of purified Amylase-4 enzyme standard control sample was incorporated in the experiment. The activity (i.e. productivity) of the Amylase-4 enzyme are shown in FIG. 5A and FIG. 5B.

Example 8

One Liter Bioreactor Production of Amylase Enzyme in Modified and Parental *B. licheniformis* Cells One Liter bioreactors set up in quadruplicate to run a standard *B. licheniformis* fermentation process were used to compare Amylase-3 enzyme expression in modified *Bacillus licheniformis* cells comprising the "rpoC-D796G" substitution described in Example 2 and wild-type (parental) *B. licheniformis* cells. The modified and unmodified (wild-type; parental) *B. licheniformis* cells further comprise the Amylase-3 expression cassette set forth in Example 2.

The 1 L fermentations were run for 90 hours, wherein samples were taken at the indicated time points (see, FIG. 6) and the $OD_{600}$ and Amylase-3 activity were measured.

Figure 6:
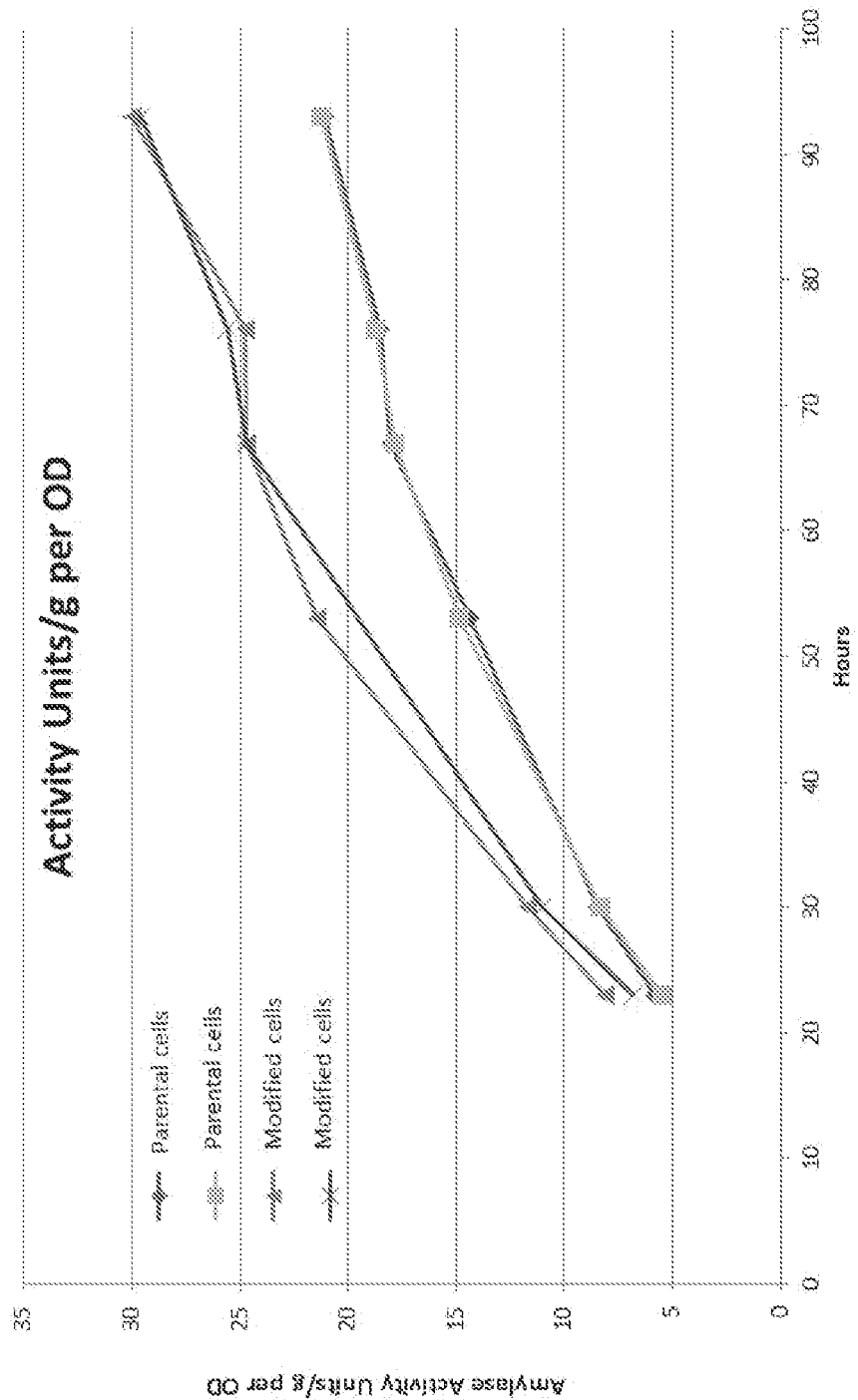
FIG. 6 presents data showing Amylase-3 enzyme production described in Example 8. As set forth in FIG. 6, Amylase-3 enzymatic activity (Units/gram/OD) from parental (wild-type) *B. licheniformis* cells and modified (daughter) *B. licheniformis* cells comprising the rpoC gene variant (i.e., encoding the RpoC (β'-subunit) "D796G" polypeptide variant) are plotted as a function of time (hours).

As set forth in FIG. 6, the modified *B. licheniformis* cells (comprising the rpoC-D796G substitution) showed a significant increase in enzyme activity over the parental (wild-type) *B. licheniformis* cells. Likewise, the modified *B. licheniformis* had higher $OD_{600}$ readings, indicating a larger cell population (which could by itself produce higher enzyme activity). To account for the OD difference, the data presented in FIG. 6 are expressed as U/g per $OD_{600}$ unit, which shows a clear increase in enzyme activity from the modified *B. licheniformis* cells relative to the parental *B. licheniformis*.

Example 9

Transformation Efficiency of Modified *B. licheniformis* Host Cells

In the present example, the transformation efficiency of modified *B. licheniformis* host cells were analyzed for their ability to take up a replicating plasmid comprising a gene of interest encoding GC358 amylase as described in U.S. Pat. No. 8,361,755.

Figure 7:
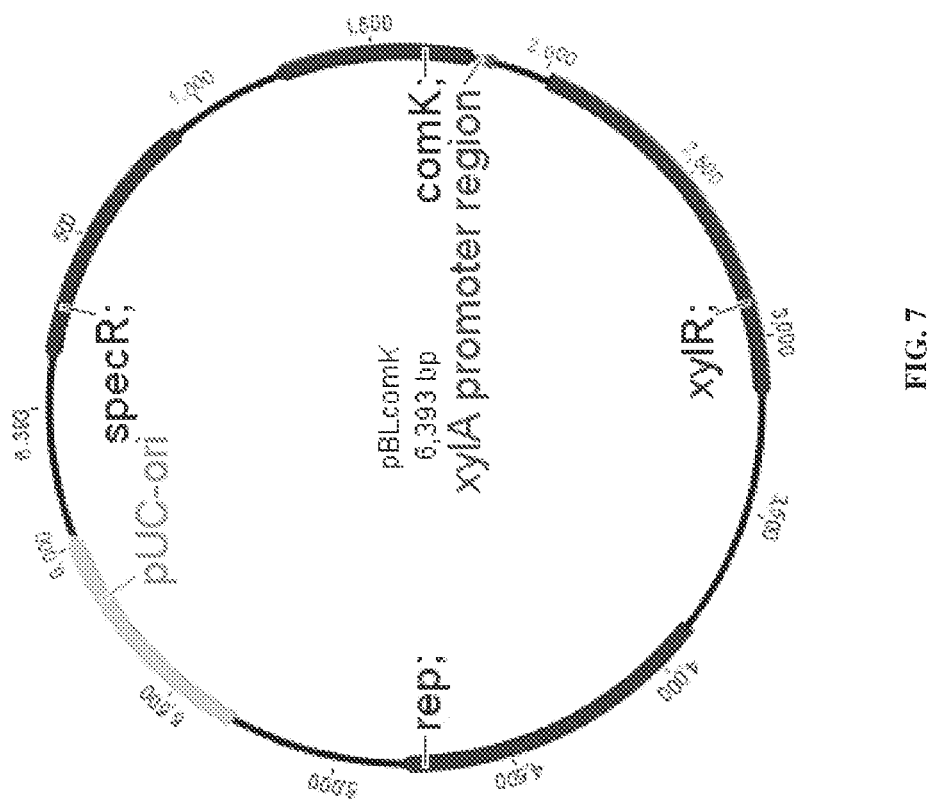
FIG. 7 shows a map of plasmid pBLComK, which includes DNA sequences encoding the pBR322 origin of replication, the *Enterococcus faecalis* Spectinomycin resistance (Spec$^r$) gene spc (also called aad9), the *B. subtilis* (natto) plasmid pTA1060 rep gene for replication in Bacilli, the *B. licheniformis* comK gene controlled by the *B. subtilis* xyIA promoter, and the *B. subtilis* xyIR gene.

More particularly, the transformation efficiency of the following three *B. licheniformis* host cells were analyzed: Host Cell 1 is a parental (control) *B. licheniformis* host cell encoding a rpoB (478V) polypeptide (SEQ ID NO: 4) and a wild-type (native) rpoC polypeptide (SEQ ID NO: 8); Host Cell 2 is a modified (daughter) *B. licheniformis* host cell encoding a modified rpoB polypeptide (i.e., a valine to alanine substitution at position 478 of SEQ ID NO: 4) and a wild-type (native) rpoC polypeptide (SEQ ID NO: 8) and Host Cell 3 is a modified daughter *B. licheniformis* host cell encoding a rpoB (V478A) polypeptide (SEQ ID NO: 4) and a modified rpoC polypeptide (i.e., an aspartic acid to glycine substitution at position 796 of SEQ ID NO: 8). In addition, in order to perform the competency assays in the above-described host cells, each host cell comprises a pBL-ComK plasmid expressing ComK from a xylose inducible promoter (e.g., see, FIG. 7 plasmid map).

Transformation Efficiency Assay

The parental (control) B. Licheniformis host cell (i.e., Host Cell 1) and the modified (daughter) B. Licheniformis host cells (i.e., Host Cell 2 and Host Cell 3) described above were plated onto LB plates containing 100 mg/l spectinomycin and cultured overnight at 37° C. Duplicate pre-culture shake flasks with 25 ml of LB containing 100 mg/l spectinomycin were inoculated from a single colony and cultured overnight at 37° C. at 250 RPM using a 50 ml throw.

From this pre-culture, the main culture was inoculated at $OD_{600}$ of 0.7 (in duplicate) in 50 ml LB containing 100 mg/l spectinomycin. The main culture was performed in 250 ml baffled Erlenmeyer flasks and cultured at 37° C. at 250 RPM using a 50 ml throw. Once every hour for a total of eight (8) hours, the $OD_{600}$ was measured. After the first hour of cultivation, 0.3% xylose was added to the culture broth. At the three (3), four (4), five (5), six (6), seven (7) and eight (8) hour time points, 112.5 µl of culture broth was added to 12.5 µl of 100% DMSO and stored at −80° C.

Figure 8:
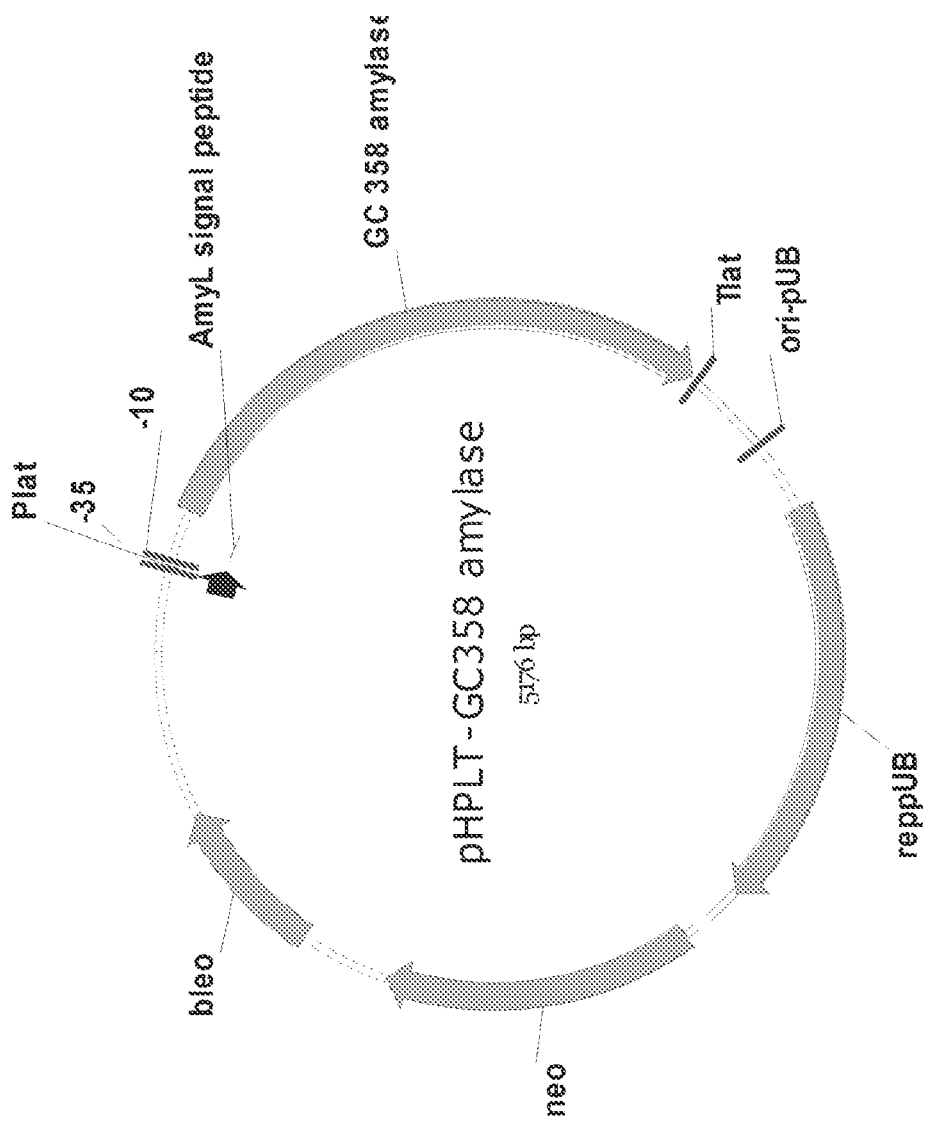
FIG. 8 presents a plasmid map of pHPLT encoding an amylase.

The transformation efficiencies were tested by making use of plasmid pHPLT-GC358 amylase (FIG. 8). This plasmid contains a gene for expression of GC358 amylase (e.g., see, U.S. Pat. No. 8,361,755), cloned into the pHPLT vector (Solingen et al., 2001). After addition of the plasmid DNA, cells were incubated at 37° C. in a tabletop thermoshaker set to 1000 RPM for one (1) hour. Cells were plated on starch plates containing 20 mg/l neomycin. After two (2) days incubation at 37° C. degrees, all halo forming colonies were counted.

Results

Figure 9:
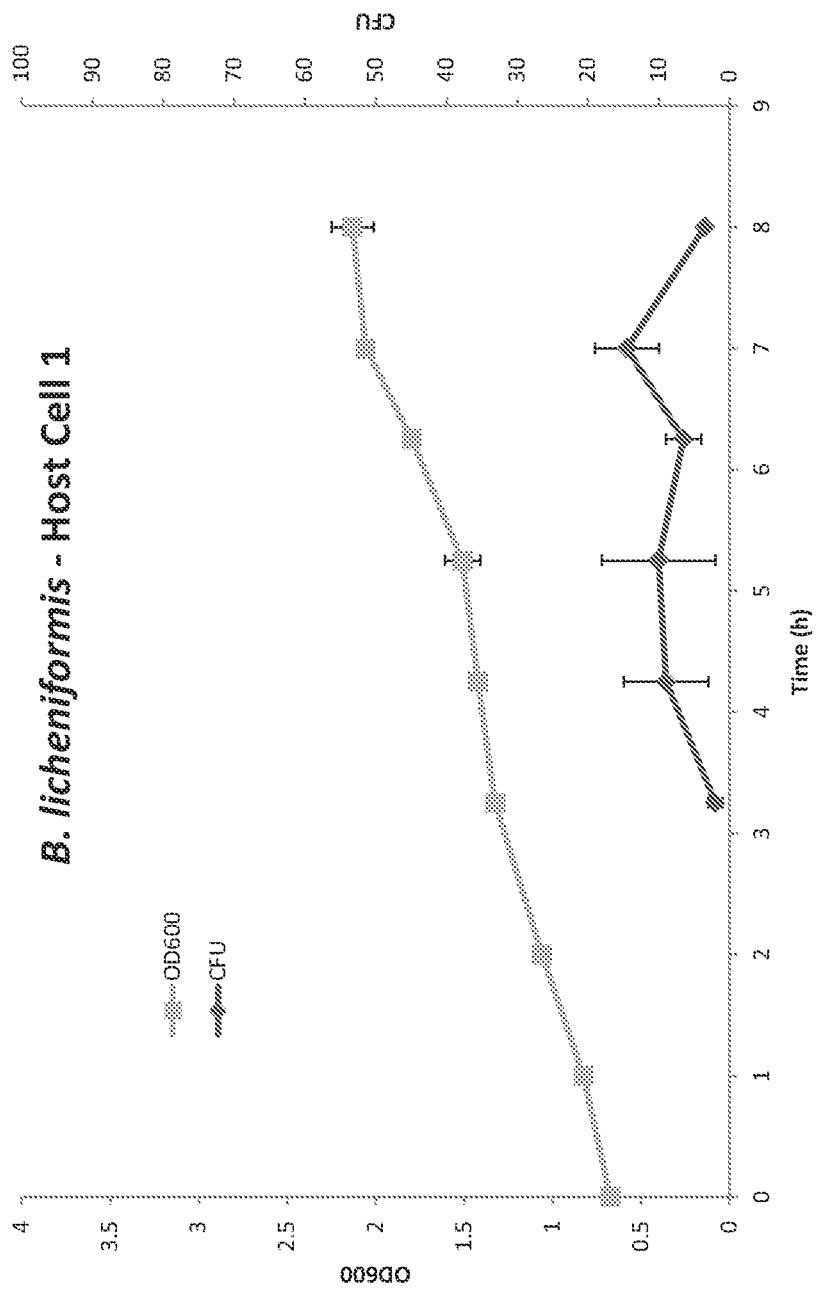
FIG. 9 shows *B. licheniformis* host cell transformation efficiency data (OD$_{600}$ and CFU's) of a parental (control) *B. licheniformis* host cell comprising/encoding rpoB (478V) and wild-type (native) rpoC polypeptides.
Figure 10:
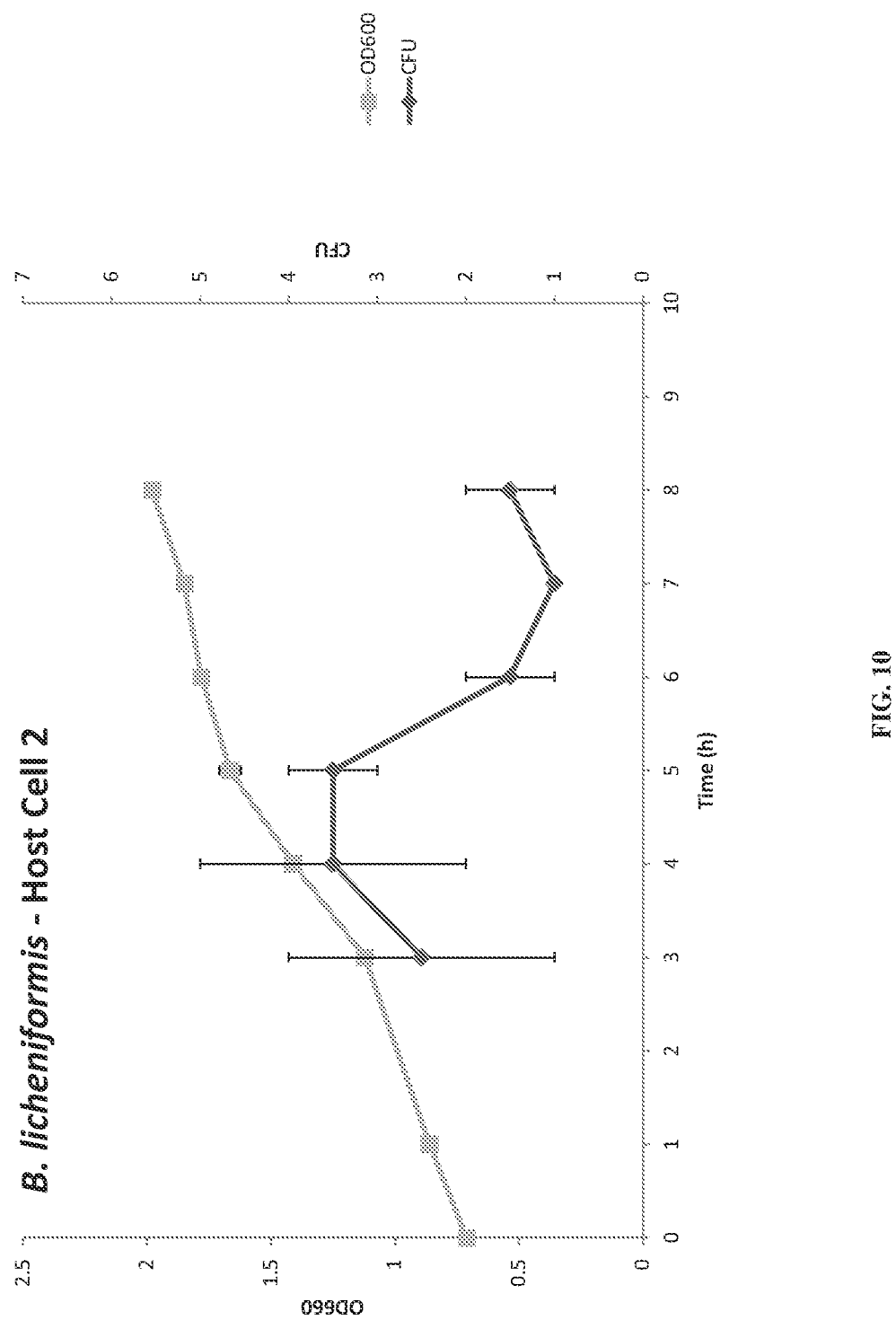
FIG. 10 shows *B. licheniformis* host cell transformation efficiency data (OD$_{600}$ and CFU's) of a daughter (modified) *B. licheniformis* host cell comprising/encoding a mutant rpoB polypeptide (V478A) and wild-type (native) rpoC polypeptide.

As depicted in FIG. 9, the control (parental) B. licheniformis host cell (i.e., Host Cell 1; comprising/encoding rpoB (478V), wild type (native) rpoC polypeptide and plasmid pBLComK), showed transformation efficiencies of around 10 colony forming units (CFU's) with a peak at 7 hours of 15 CFU's. The modified B. licheniformis host cell (i.e., Host Cell 2) comprising/encoding the modified rpoB polypeptide (V478A; see, FIG. 10), showed a decrease in transformation efficiency relative to the parental (control) host cell (FIG. 9), with CFU average counts of 3 CFU's. These results suggest the rpoB (478V) causes an over 3-fold increase in transformation efficiency.

Figure 11:
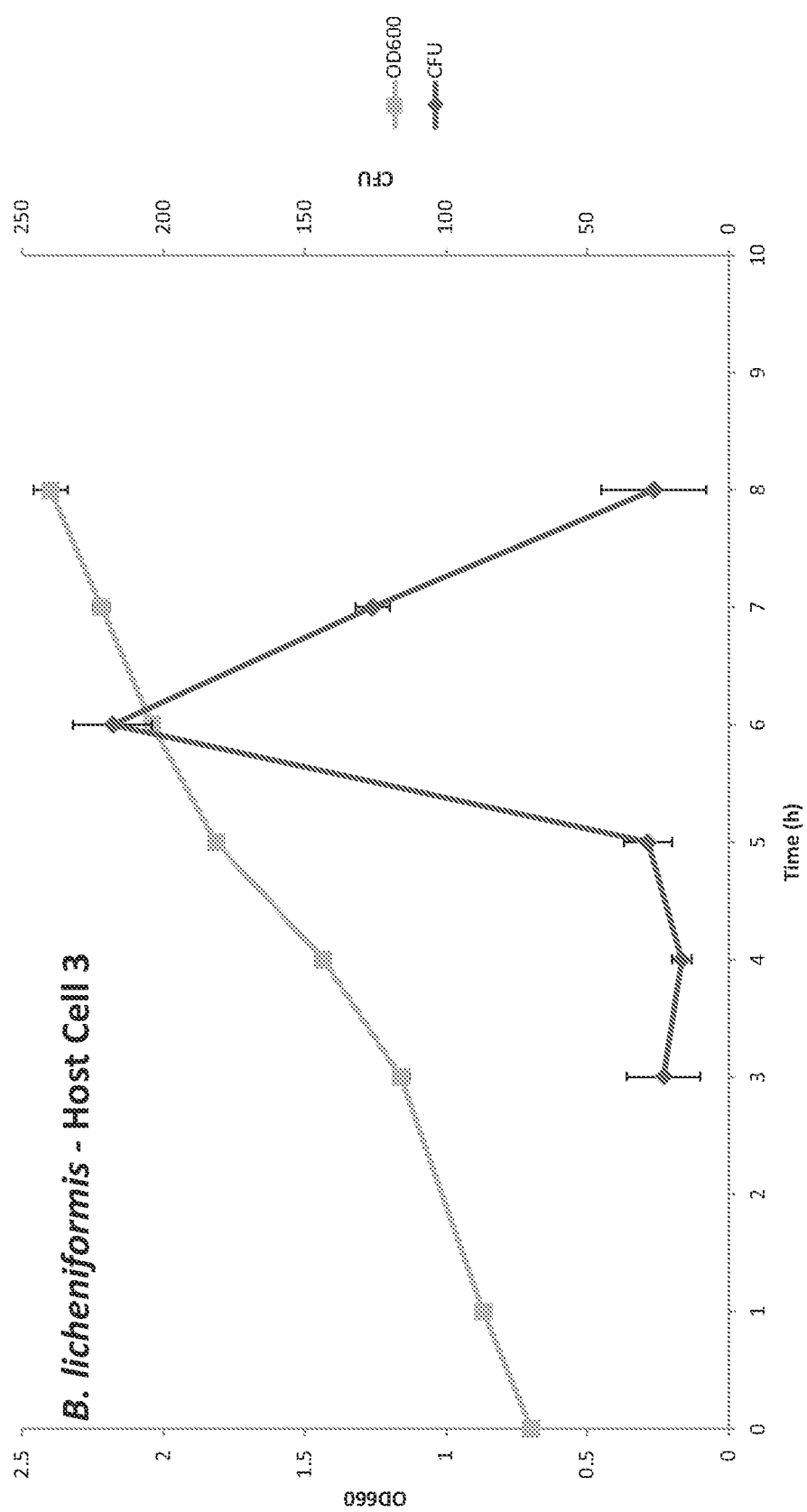
FIG. 11 shows *B. licheniformis* host cell transformation efficiency data (OD$_{600}$ and CFU's) of a daughter (modified) *B. licheniformis* host cell comprising/encoding a rpoB (478V) polypeptide and modified rpoC polypeptide (D796G).

In contrast, the modified B. licheniformis host cell (i.e., Host Cell 3; see FIG. 11) comprising/encoding rpoB (V478A) polypeptide and a modified rpoC polypeptide (D796G), showed an over 14-fold increase in transformation efficiency compared to the parental (control) host cell (FIG. 9) and an over 73-fold increase in transformation efficiency compared to Host Cell 2 (FIG. 10), indicating that the rpoC "D796G" mutation has a significant and positive effect on transformation efficiency of B. licheniformis.

REFERENCES

PCT International Publication No. WO2001/51643
PCT International Publication No. WO2003/055996
PCT International Publication No. WO2005/111203
PCT International Publication No. WO2008/112459
PCT International Publication No. WO2009/149395
PCT International Publication No. WO2009/149419
PCT International Publication No. WO2010/056635
PCT International Publication No. WO2010/14483
PCT International Publication No. WO2013/086219
PCT International Publication No. WO2014/164777
U.S. Patent Application Publication No. 2004/0171154
U.S. Pat. No. 8,361,755
U.S. Pat. No. 6,361,966
U.S. Pat. No. 5,264,366
Barton et al., Nucleic Acids Res., 18:7349-4966, 1990.
Solingen et al., Extremophiles 5:333-41, 2001.
Borukhov & Severinov, Res. Microbiol. 153:557-562, 2002.
Brigidi et al., FEMS Microbiol. Lett 55: 135-138, 1990.
Calissano and Macino, Fungal Genet. Newslett., 43: 15-16, 1996.
Cavaco-Paulo & Gübitz, Textile Processing with Enzymes, 2003, 1st Edition.
Chakraborty et al., Science 337:591-595, 2012.
Chelikani et al., Cell Mol. Life Sci., 61:192-208, 2004.
Conrad et al., Proc. Natl. Acad. Sci. U.S.A 107:20500-20505, 2010.
Cramer, Curr. Opin. Struct. Biol. 12:89-97, 2002.
Cui et al., Antimicrob. Agents Chemother. 54:5222-5233, 2010.
de Haseth & Helmann, Mol. Microbiol. 16:817-824, 1995.
Ferrari et al., "Genetics," in Hardwood et al, (eds.), Bacillus, Plenum Publishing
Corp., pages 57-72, 1989.
Fukuda et al., Mol. Gen. Genet. 154:135, 1977.
Guérout-Fleury et al. Gene, 167(1-2):335-336, 1995.
Harwood et al., Molecular Biological Methods For Bacillus, John Wiley, 1990.
Hu Xuezhi et al., Acta Microbiologica Sinica 31: 268-273, 1991.
Ingham & Furneaux, Microbiology, 146: 3041-3049, 2000.
Janes & Stibitz, Infect. Immun., 74(3):1949-1953, 2006.
Juang & Helmann, J. Mol. Biol. 239:1-14, 1994.
Kane et al., J. Bacteriol. 137: 1028-1030, 1994.
Kleckner et al., Methods Enzymology, 204: 139-180, 1991.
Klein-Marcuschamer et al., Appl. Environ. Microbiol. 75:2705-2711, 2009.
Kren et al., Nat. Med., 4: 285-290, 1998.
Lane & Darst, J. Mol. Biol. 395:686-704, 2010.
Lee et al., Antimicrobial Agents and Chemotherapy, 57:56-65, 2013.
Lopez de Saro et al., J. Mol. Biol. 252:189-202, 1995.
Maughan et al., J. Bacteriol. 186:2481-2486, 2004.
Miller, "A SHORT COURSE IN BACTERIAL GENETICS: A LABORATORY MANUAL AND HANDBOOK FOR ESCHERICHIA COLI AND RELATED BACTERIA", Cold Spring Harbor Laboratory Press, Plainview, N.Y. 1992.
Nalankilli. G., Colourage, 1998, XLV (10), 17-19; Shenai, V. A. and Saraf, N.M. Technology of Finishing, (1990),Vol. X.II Edition)
Needleman and Wunsch, Journal of Molecular Biology, 48,443-453, 1970.
Neidhardt et al., J. Bacteriol., 119: 736-747, 1974.
Patnaik, Biotechnol Prog., 24: 38-47, 2008.

Sambrook et al., MOLECULAR CLONING: A LABORATORY MANUAL, 2nd ed., Cold Spring Harbor, 1989, and 3rd ed., 2001.
Scherer and Davis, Proc. Natl. Acad. Sci. USA, 76:4949-4955, 1979.
Selifonova et al., Appl Environ Microbiol., I67: 3645-3649, 2001.
Sharipova et al., Microbiology 63:29-32, 1994.
Smith & Youngman, Biochimie, 74(7-8):705-711, 1992.
Storici et al., Nature Biotechnol., 19: 773-776, 2001.
Vogtentanz et al., "A *Bacillus subtilis* fusion protein system to produce soybean Bowman-Birk protease inhibitor", Protein Expr Purif, 55(1):40-52, 2007.
Vogtentanz, Protein Expr. Purif., 55:40-52, 2007.
Wang et al., "Expression and secretion of human atrial natriuretic alpha-factor in *Bacillus subtilis* using the subtilisin signal peptide", Gene, 69(1):39-47, 1988.

What is claimed is:

1. A method for increasing expression of a protein of interest (POI) in a *Bacillus* cell comprising:
   (a) obtaining a modified *Bacillus* cell expressing an increased amount of a POI, wherein the modified *Bacillus* cell comprises at least one mutation in a rpoC gene encoding a variant RNA-polymerase (RNAP) β'-subunit polypeptide, wherein the variant β'-subunit polypeptide has at least 90% sequence identity to SEQ ID NO: 6 or 8 and comprises an aspartic acid to glycine substitution at amino acid residue 796 (D796G), or at the equivalent position in any *Bacillus* RNAP β'-subunit family member and
   (b) culturing the modified cell under conditions such that the POI is expressed, wherein the modified *Bacillus* cell expresses an increased amount of a POI relative to the expression of the POI in an unmodified *Bacillus* control cell.

2. The method of claim 1, wherein the rpoC gene encoding the variant β'-subunit polypeptide comprises at least 80% sequence identity to SEQ ID NO: 5 or 7.

3. The method of claim 1, further comprising at least one mutation in a rpoB gene encoding a variant RNAP β-subunit polypeptide.

4. The method of claim 1, wherein the increased amount of an expressed POI relative to the unmodified *Bacillus* control cell is at least 5%.

5. The method of claim 1, wherein the rpoC gene encoding the variant β"-subunit polypeptide is integrated into the chromosome of the modified cell.

6. The method of claim 1, wherein the rpoC gene encoding the variant β"-subunit polypeptide is comprised on an extrachromosomal plasmid of the modified cell.

7. The method of claim 1, wherein the variant β"-subunit polypeptide further comprises at least one mutation at an amino acid residue position selected from the group consisting of 751, 784, 797 and 1018-1020.

8. The method of claim 7, wherein the at least one mutation is selected from the group consisting of: a methionine to isoleucine (M751 I) substitution at amino acid residue position 751, an arginine to histidine (R784H) substitution at amino acid residue position 784, a serine to phenylalanine (S797F) substitution at amino acid residue position 797, a deletion of amino acid residues 1018, 1019 and 1020 (ΔI1018-R1020) at amino acid residue position 1018-1020, of SEQ ID NO: 6 or 8, or a combination thereof.

9. The method of claim 1, wherein the *Bacillus* cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii* and *B. thuringiensis*.

10. The method of claim 1, wherein the POI is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

* * * * *

SEQUENCE LISTING

<160> NUMBER OF SEQ ID NOS: 37

<210> SEQ ID NO 1
<211> LENGTH: 3582
<212> TYPE: DNA
<213> ORGANISM: Bacillus subtilis

<400> SEQUENCE: 1

```
ttgacaggtc aactagttca gtatggacga caccgccagc gcagaagcta tgctcgcatt      60
agcgaagtgt tagaattacc aaatctcatt gaaattcaaa cctcttctta tcagtggttt     120
cttgatgagg gtcttagaga gatgtttcaa gacatatcac caattgagga tttcactggt     180
aacctctctc ttgagttcat tgattatagt ttaggtgagc taaatatcc gtagaggaa      240 tcaaaagaac gtgatgtgac ttactcagct ccgctaagag tgaaggttcg tttaattaac     300
aaagaaactg gagaggtaaa agaccaagat gtcttcatgg gtgatttccc tattatgaca     360
gatacaggta cttttatcat taacggtgcg gaacgtgtta tcgtttccca gcttgttcgg     420
tctccaagtg tatatttcag tggtaaagta gacaaaaacg gtaaaaaagg ttttaccgca     480
actgtcattc caaaccgtgg cgcatggtta aatacgaaa ctgatgcgaa agatgttgtt      540
tatgtccgca ttgatcgcac acgtaagttg ccggttacgg ttcttttgcg tgctctcggc     600
ttcggctccg atcaagagat tcttgatctc ataggagaaa acgaatacct gcgaaatacg     660
cttgataaag ataacacaga aaacagcgac aaagcgttgc tggaaattta cgagcgtctc     720
cgtcctggag agccgcctac agtagaaaat gcgaaaagct tgcttgattc tcgtttcttt     780
gatccgaaac gatacgatct tgccaatgta ggacgctata aaattaataa aaaacttcat     840
attaagaatc gcctcttcaa tcagagactt gctgaaacgc ttgttgatcc tgaaacagga     900
gaaatccttg ctgaaaaagg ccagattctt gatagaagaa cgcttgataa agtactgcca     960
tacttagaaa acggaatcgg ttttagaaag ctgtatccga atggcggcgt tgttgaagat    1020
gaagtgactc ttcaatcaat taaaatcttt gctccgactg atcaagaagg agaacaggtt    1080
atcaatgtaa tcggcaatgc ttacatcgaa gaagagatta aaaacatcac gcctgctgat    1140
attatttctt caatcagcta cttcttcaac ctgctgcacg gagtaggcga cacagatgat    1200
atcgatcatc ttggaaaccg ccgtttacgt tctgtaggcg agcttctcca gaaccaattc    1260
cgtatcggtt taagccgtat ggagcgtgtg gttcgtgaga aatgtcaat tcaagatacg     1320 aatacaatta cgcctcagca gctgatcaat attcgtcctg ttattgcgtc cattaaagag    1380
ttctttggaa gctcacagct ttctcaattc atggatcaga cgaacccgct tgctgaatta    1440
acgcacaagc gtcgtctgtc agcattagga ccgggcggat tgcacgtga gcgtgccgga     1500 atggaagtgc gtgacgttca ctactccac tatggccgta tgtgtccgat tgaaacgcct     1560
gagggcccga acatcggttt gatcaactca ctatcatctt atgcaaaagt aaaccgtttt    1620
ggctttattg aaacgccata tgccgcgtt gaccctgaaa cagggaaggt aacgggcaga     1680
atcgattact taactgctga tgaagaggat aactatgttg tcgctcaagc gaatgctcgt    1740
```

```
cttgatgacg aaggcgcctt tattgatgac agcatcgtag ctcgtttccg cggggagaac    1800
accgttgttt ccagaaatcg tgtagactac atggatgtat cgcctaagca ggttgtatct    1860
gctgcgacag catgtatccc gttcttagaa aacgatgact ccaaccgtgc cctcatggga    1920
gcgaacatgc agcgtcaggc tgtgcctttg atgcagccgg aagcgccatt tgttggaact    1980
ggtatggaat acgtatcagg aaaagactct ggtgccgctg ttatttgtaa acaccctggt    2040
atcgttgaac gcgtagaagc caaaaacgtt tgggttcgcc gttatgaaga agtagacggt    2100
caaaaagtaa aaggaaacct ggataaatac agcctgctga aatttgtccg ctctaaccaa    2160
ggtacgtgct acaaccagcg tccgatcgta agtgtcggcg atgaagtggt aaaaggagaa    2220
atccttgctg acggtccttc tatggagctt ggtgaacttg cacttggccg taacgtaatg    2280
gtcggcttca tgacgtggga tggctacaac tatgaggatg ccatcatcat gagtgaacgc    2340
ctagtgaagg atgatgttta tacatctatc cacattgaag aatacgaatc agaagcacgt    2400
gatacgaaac ttggacctga agaaatcact cgcgatattc aaacgtcgg tgaagatgcg    2460 cttcgcaatc ttgatgaccg cggaatcatc cgtattgggg cagaagtaaa agacggagat    2520
cttcttgttg gtaaagtaac gcctaaaggc gtaactgaac tgactgccga gaacgccttt    2580
cttcacgcca tctttggcga gaaagcccgc gaggttcgtg atacttctct tcgtgtgcct    2640
catggcggcg gcggaattat ccatgacgtt aaagtcttca accgtgaaga cggagacgaa    2700
cttcctccag gtgttaacca gttagtacgc gtatatatcg ttcagaaacg taagatttct    2760
gaaggggata aaatggccgg tcgtcacggt aacaaaggtg ttatctctaa gattcttcct    2820
gaagaggata tgccttacct tcctgacggc acaccaattg atatcatgct taacccgctg    2880
ggcgtaccat cacgtatgaa catcgggcag gtattggaac ttcacatggg tatggccgct    2940
cgttaccttg gcattcacat tgcatctcct gtatttgacg gagcgcgaga agaggatgtc    3000
tgggaaacac ttgaagaagc cggcatgtct cgtgacgcca aaacagtgct ttacgacgga    3060
cgtactggag agccgtttga taaccgtgta tctgtcggta tcatgtacat gatcaaactg    3120
gctcacatgg ttgacgataa acttcatgca cgctctacag gcccttactc acttgttacg    3180
cagcagcctc ttggcggtaa agcgcaattt ggcggacagc gttttggtga gatggaggtt    3240
tgggcacttg aagcttacgg tgcggcttac actcttcaag aaattctgac tgttaagtct    3300
gatgacgtgg ttggacgtgt gaaaacatac gaagccatcg ttaaaggcga caatgttcct    3360
gaaccaggtg ttccggaatc attcaaagta ttaatcaaag aacttcaaag cttaggtatg    3420
gatgtcaaaa tcctttctgg tgatgaagaa gaaatagaaa tgagagattt agaagacgaa    3480
gaagatgcga aacaagctga cggcctggca ttatcaggtg atgaagagcc ggaagaaaca    3540
gcatctgcag acgttgaacg cgatgtagta acaaaagaat aa                      3582
```

<210> SEQ ID NO 2
<211> LENGTH: 1193
<212> TYPE: PRT
<213> ORGANISM: Bacillus subtilis

<400> SEQUENCE: 2

Leu Thr Gly Gln Leu Val Gln Tyr Gly Arg His Arg Gln Arg Ser
1               5                   10                  15

Tyr Ala Arg Ile Ser Glu Val Leu Glu Leu Pro Asn Leu Ile Glu Ile
            20                  25                  30

Gln Thr Ser Ser Tyr Gln Trp Phe Leu Asp Glu Gly Leu Arg Glu Met
        35                  40                  45

```
Phe Gln Asp Ile Ser Pro Ile Glu Asp Phe Thr Gly Asn Leu Ser Leu
     50                  55                  60

Glu Phe Ile Asp Tyr Ser Leu Gly Glu Pro Lys Tyr Pro Val Glu Glu
 65                  70                  75                  80

Ser Lys Glu Arg Asp Val Thr Tyr Ser Ala Pro Leu Arg Val Lys Val
                 85                  90                  95

Arg Leu Ile Asn Lys Glu Thr Gly Glu Val Lys Asp Gln Asp Val Phe
            100                 105                 110

Met Gly Asp Phe Pro Ile Met Thr Asp Thr Gly Thr Phe Ile Ile Asn
            115                 120                 125

Gly Ala Glu Arg Val Ile Val Ser Gln Leu Val Arg Ser Pro Ser Val
        130                 135                 140

Tyr Phe Ser Gly Lys Val Asp Lys Asn Gly Lys Lys Gly Phe Thr Ala
145                 150                 155                 160

Thr Val Ile Pro Asn Arg Gly Ala Trp Leu Glu Tyr Glu Thr Asp Ala
                165                 170                 175

Lys Asp Val Val Tyr Val Arg Ile Asp Arg Thr Arg Lys Leu Pro Val
            180                 185                 190

Thr Val Leu Leu Arg Ala Leu Gly Phe Gly Ser Asp Gln Glu Ile Leu
        195                 200                 205

Asp Leu Ile Gly Glu Asn Glu Tyr Leu Arg Asn Thr Leu Asp Lys Asp
    210                 215                 220

Asn Thr Glu Asn Ser Asp Lys Ala Leu Leu Glu Ile Tyr Glu Arg Leu
225                 230                 235                 240

Arg Pro Gly Glu Pro Pro Thr Val Glu Asn Ala Lys Ser Leu Leu Asp
                245                 250                 255

Ser Arg Phe Phe Asp Pro Lys Arg Tyr Asp Leu Ala Asn Val Gly Arg
            260                 265                 270

Tyr Lys Ile Asn Lys Lys Leu His Ile Lys Asn Arg Leu Phe Asn Gln
        275                 280                 285

Arg Leu Ala Glu Thr Leu Val Asp Pro Glu Thr Gly Glu Ile Leu Ala
    290                 295                 300

Glu Lys Gly Gln Ile Leu Asp Arg Arg Thr Leu Asp Lys Val Leu Pro
305                 310                 315                 320

Tyr Leu Glu Asn Gly Ile Gly Phe Arg Lys Leu Tyr Pro Asn Gly Gly
                325                 330                 335

Val Val Glu Asp Glu Val Thr Leu Gln Ser Ile Lys Ile Phe Ala Pro
            340                 345                 350

Thr Asp Gln Glu Gly Glu Gln Val Ile Asn Val Ile Gly Asn Ala Tyr
        355                 360                 365

Ile Glu Glu Glu Ile Lys Asn Ile Thr Pro Ala Asp Ile Ile Ser Ser
    370                 375                 380

Ile Ser Tyr Phe Phe Asn Leu Leu His Gly Val Gly Asp Thr Asp Asp
385                 390                 395                 400

Ile Asp His Leu Gly Asn Arg Arg Leu Arg Ser Val Gly Glu Leu Leu
                405                 410                 415

Gln Asn Gln Phe Arg Ile Gly Leu Ser Arg Met Glu Arg Val Val Arg
            420                 425                 430

Glu Arg Met Ser Ile Gln Asp Thr Asn Thr Ile Thr Pro Gln Gln Leu
        435                 440                 445

Ile Asn Ile Arg Pro Val Ile Ala Ser Ile Lys Glu Phe Phe Gly Ser
    450                 455                 460
```

-continued

```
Ser Gln Leu Ser Gln Phe Met Asp Gln Thr Asn Pro Leu Ala Glu Leu
465                 470                 475                 480

Thr His Lys Arg Arg Leu Ser Ala Leu Gly Pro Gly Leu Thr Arg
                485                 490                 495

Glu Arg Ala Gly Met Glu Val Arg Asp Val His Tyr Ser His Tyr Gly
                500                 505                 510

Arg Met Cys Pro Ile Glu Thr Pro Glu Gly Pro Asn Ile Gly Leu Ile
            515                 520                 525

Asn Ser Leu Ser Ser Tyr Ala Lys Val Asn Arg Phe Gly Phe Ile Glu
            530                 535                 540

Thr Pro Tyr Arg Arg Val Asp Pro Glu Thr Gly Lys Val Thr Gly Arg
545                 550                 555                 560

Ile Asp Tyr Leu Thr Ala Asp Glu Glu Asp Asn Tyr Val Val Ala Gln
                565                 570                 575

Ala Asn Ala Arg Leu Asp Asp Glu Gly Ala Phe Ile Asp Asp Ser Ile
                580                 585                 590

Val Ala Arg Phe Arg Gly Glu Asn Thr Val Val Ser Arg Asn Arg Val
            595                 600                 605

Asp Tyr Met Asp Val Ser Pro Lys Gln Val Val Ser Ala Ala Thr Ala
610                 615                 620

Cys Ile Pro Phe Leu Glu Asn Asp Asp Ser Asn Arg Ala Leu Met Gly
625                 630                 635                 640

Ala Asn Met Gln Arg Gln Ala Val Pro Leu Met Gln Pro Glu Ala Pro
                645                 650                 655

Phe Val Gly Thr Gly Met Glu Tyr Val Ser Gly Lys Asp Ser Gly Ala
                660                 665                 670

Ala Val Ile Cys Lys His Pro Gly Ile Val Glu Arg Val Glu Ala Lys
            675                 680                 685

Asn Val Trp Val Arg Arg Tyr Glu Glu Val Asp Gly Gln Lys Val Lys
            690                 695                 700

Gly Asn Leu Asp Lys Tyr Ser Leu Leu Lys Phe Val Arg Ser Asn Gln
705                 710                 715                 720

Gly Thr Cys Tyr Asn Gln Arg Pro Ile Val Ser Val Gly Asp Glu Val
                725                 730                 735

Val Lys Gly Glu Ile Leu Ala Asp Gly Pro Ser Met Glu Leu Gly Glu
            740                 745                 750

Leu Ala Leu Gly Arg Asn Val Met Val Gly Phe Met Thr Trp Asp Gly
            755                 760                 765

Tyr Asn Tyr Glu Asp Ala Ile Ile Met Ser Glu Arg Leu Val Lys Asp
770                 775                 780

Asp Val Tyr Thr Ser Ile His Ile Glu Glu Tyr Glu Ser Glu Ala Arg
785                 790                 795                 800

Asp Thr Lys Leu Gly Pro Glu Glu Ile Thr Arg Asp Ile Pro Asn Val
                805                 810                 815

Gly Glu Asp Ala Leu Arg Asn Leu Asp Asp Arg Gly Ile Ile Arg Ile
                820                 825                 830

Gly Ala Glu Val Lys Asp Gly Asp Leu Leu Val Gly Lys Val Thr Pro
            835                 840                 845

Lys Gly Val Thr Glu Leu Thr Ala Glu Glu Arg Leu His Ala Ile
            850                 855                 860

Phe Gly Glu Lys Ala Arg Glu Val Arg Asp Thr Ser Leu Arg Val Pro
865                 870                 875                 880

His Gly Gly Gly Gly Ile Ile His Asp Val Lys Val Phe Asn Arg Glu
```

885                 890                 895
Asp Gly Asp Glu Leu Pro Pro Gly Val Asn Gln Leu Val Arg Val Tyr
                900                 905                 910
Ile Val Gln Lys Arg Lys Ile Ser Glu Gly Asp Lys Met Ala Gly Arg
                915                 920                 925
His Gly Asn Lys Gly Val Ile Ser Lys Ile Leu Pro Glu Glu Asp Met
        930                 935                 940
Pro Tyr Leu Pro Asp Gly Thr Pro Ile Asp Ile Met Leu Asn Pro Leu
945                 950                 955                 960
Gly Val Pro Ser Arg Met Asn Ile Gly Gln Val Leu Glu Leu His Met
                965                 970                 975
Gly Met Ala Ala Arg Tyr Leu Gly Ile His Ile Ala Ser Pro Val Phe
                980                 985                 990
Asp Gly Ala Arg Glu Glu Asp Val Trp Glu Thr Leu Glu Glu Ala Gly
                995                 1000                1005
Met Ser Arg Asp Ala Lys Thr Val Leu Tyr Asp Gly Arg Thr Gly
        1010                1015                1020
Glu Pro Phe Asp Asn Arg Val Ser Val Gly Ile Met Tyr Met Ile
        1025                1030                1035
Lys Leu Ala His Met Val Asp Asp Lys Leu His Ala Arg Ser Thr
        1040                1045                1050
Gly Pro Tyr Ser Leu Val Thr Gln Gln Pro Leu Gly Gly Lys Ala
        1055                1060                1065
Gln Phe Gly Gly Gln Arg Phe Gly Glu Met Glu Val Trp Ala Leu
        1070                1075                1080
Glu Ala Tyr Gly Ala Ala Tyr Thr Leu Gln Glu Ile Leu Thr Val
        1085                1090                1095
Lys Ser Asp Asp Val Val Gly Arg Val Lys Thr Tyr Glu Ala Ile
        1100                1105                1110
Val Lys Gly Asp Asn Val Pro Glu Pro Gly Val Pro Glu Ser Phe
        1115                1120                1125
Lys Val Leu Ile Lys Glu Leu Gln Ser Leu Gly Met Asp Val Lys
        1130                1135                1140
Ile Leu Ser Gly Asp Glu Glu Ile Glu Met Arg Asp Leu Glu
        1145                1150                1155
Asp Glu Glu Asp Ala Lys Gln Ala Asp Gly Leu Ala Leu Ser Gly
        1160                1165                1170
Asp Glu Glu Pro Glu Glu Thr Ala Ser Ala Asp Val Glu Arg Asp
        1175                1180                1185
Val Val Thr Lys Glu
        1190

<210> SEQ ID NO 3
<211> LENGTH: 3582
<212> TYPE: DNA
<213> ORGANISM: Bacillus licheniformis

<400> SEQUENCE: 3
ttgacaggtc aactagttca gtatggacga caccgccagc gcagaagcta tgcacgcatt        60
agcgaagtgt tagaattacc aaatctcatt gaaattcaaa cctcttctta tcagtggttt       120
cttgatgagg tcttagaga  gatgtttcaa gacatatcgc caattgagga tttcactggt       180
aacctctctc tggaatttat cgactacagc ttgggcgagc taagtatcc  ggtagaagaa       240 tcaaaagagc gggatgtgac ctattcagct ccgctgcggg ttaaagtccg cttaatcaac       300

```
aaagaaaccg gcgaagtaaa agatcaggat gtcttcatgg gcgatttccc tattatgaca      360
gacactggaa ccttcattat caacggtgca gaacgggtca tcgtatctca gctcgttcgt      420
tctccaagtg tatattttag tggtaaagta gacaaaaacg gtaagaaagg ttttaccgcg      480
actgtcattc caaaccgtgg cgcatggtta gaatacgaga ctgatgcgaa agatgttgtt      540
tacgtacgca tcgatcgcac acgtaagttg ccggttacgg ttcttttgcg tgctcttggc      600
ttcggatctg accaagagat cattgatctc atcggtgaaa acgagtatct gcgcaatacg      660
cttgataaag ataatacgga aaacaccgat aaagcgcttc ttgaaatcta cgagcgtctt      720
cgtccagggg agccgcctac cgtagaaaac gcaaaaagcc tgcttgattc aaggttcttt      780
gatccgaaaa gatatgacct tgcgagtgta ggacgttata aaattaataa aaagcttcac      840
atcaaaaacc gacttttaa tcagcggctt gctgaaacgc tagtcgaccc tgaaacaggc      900
gaaatccttg ccgaaaaagg agcgatttta gacagaagaa cgcttgataa agttctgccg      960
taccttgaaa acggaatcgg ttttaaaaag ctttatccga acggcggagt tgtcgaagac     1020
gaagtaacgc ttcagtctat caaaatctat gctccgacag accaagaagg ggagcagaca     1080
atcaatgtga ttggaaatgc ttatatcgaa gaaggcgtta agaatattac accttctgat     1140
attatcgctt ccatcagcta tttctttaac ctgcttcacg gagtgggcga taccgacgat     1200
atcgaccatc taggaaaccg ccgtctccgt tcagtgggag agcttctgca aaaccaattc     1260
cgtattggtt taagcagaat ggagcgcgtt gttcgtgaaa gaatgtctat tcaagataca     1320
aacacgatca cgccgcagca gctgatcaat attcgccctg tcatcgcatc aatcaaagag     1380
tttttcggaa gctcgcagct ttctcagttt atggatcaga cgaatccgct tgttgagctg     1440
acgcataagc gccgtctgtc agcgctcgga ccgggcggtt tgactcgtga gcgcgccgga     1500
atggaagtcc gtgacgttca ctattcacac tacgccgga tgtgtccgat tgaaacccct      1560
gagggtccaa acatcggctt gatcaactcg ctttcttcat tcgcgaaagt gaaccgtttc     1620
ggcttcatcg aaacgccgta tcgccgcgtc gatcctgaaa ctggaaaagt aacgccgaga     1680
atcgattact tgacagctga tgaagaagac aactatgtcg ttgcccaggc aaacgcacgc     1740
ctgaatgatg acggttcttt tgtggatgac agcatcgtcg cccgtttcag aggggagaac     1800
accgttgttc cgaaagaccg cgtcgactat atggacgttt cgcctaaaca ggttgtctct     1860
gccgcgactc catgtattcc tttcttggaa acgatgact caaaccgcgc ccttatggga     1920
gcgaacatgc aacgtcaggc cgtacctctt atgcagcctg aatcgccgat cgtcggaacc     1980
gggatggaat atgtatctgc gaaagactcc ggtgccgctg ttatttgccg ccaccctgga     2040
atcgttgaac gggtggaagc gaagaacatc tgggtgcgcc gctatgaaga agtcgacggc     2100
cagaaagtca aagggaacct tgataaatac agcctgctga gtttgtccg ttccaaccag      2160 ggaacttgct acaaccagcg tccgatcgta agcgtcggtg atgaggttga aaaggtgaa      2220 attttagctg acgtccgtc catggaaaaa ggtgagcttg cccttggacg caacgtcatg     2280
gtcggcttta tgacatggga tggctacaac tatgaggatg ccatcatcat gagcgaacgc     2340
cttgtaaaag acgacgtata cacgtctatt catattgaag aatacgaatc agaggcccgg     2400
gatacaaaac tcggacctga agaaatcact cgcgatattc cgaacgtcgg tgaggacgct     2460
cttcgcaatc tcgatgaacg cggaattatc cgtgtcggtg ctgaagtaaa agacggagat     2520
cttcttgttg gtaaagtaac ccctaaaggt gttacagagc ttacggcgga agaacgcctg     2580
cttcatgcca tcttcgggga aaaagcgcgt gaagtgcgtg atacgtcgct gcgtgtacct     2640
```

```
cacggaggcg gcggtatcat ccttgatgta aaagtgttca accgcgaaga cggagacgaa    2700
ctgcctccgg gcgttaacca gctcgtccgc gtctacatcg ttcagaagcg taaaatttct    2760 gaagggaca aaatggccgg acgccacggt aacaaaggtg ttatttcgaa aattcttccg    2820
gaggaagata tgccgtatct gcctgacgga acgccgattg acatcatgtt aaacccgctg    2880
ggcgtaccat cgcgtatgaa catcgggcag gtgttggagc tgcaccttgg tatggctgca    2940
cgccgcctcg gtctgcatgt cgcgtcacct gtatttgacg gtgcccgcga agaagatgtg    3000
tgggaaaccc ttgaagaagc cggcatgtca agagacgcaa aaaccgtcct ttacgacggc    3060
cgaactgggg agccgtttga caaccgggtt tctgtcggca tcatgtacat gatcaaactg    3120
gcacacatgg ttgacgacaa attgcacgca cgttcaaccg gtccttactc actcgttacc    3180
cagcagcctc tcggaggtaa agcgcagttc ggcggacagc gttttggaga gatggaagtt    3240
tgggcgcttg aagcttatgg tgcagcatat acgctacaag agatcctgac tgttaaatcg    3300
gatgatgtcg taggccgtgt gaaaacatat gaagccatcg taaaaggcga caatgttcca    3360
gaacctggtg ttccggaatc gttcaaagta ttgatcaaag agcttcaaag cttaggtatg    3420
gacgtcaaaa ttctatcaag cgacgaagaa gaaatcgaaa tgagagactt ggaagacgac    3480
gaagacgcga aacaaaacga agggctttct ctgccgaatg atgaagagtc gaagagtta    3540 gtttctgctg acgcagaacg cgatgtcgtt acaaaagaat aa                      3582
```

<210> SEQ ID NO 4
<211> LENGTH: 1193
<212> TYPE: PRT
<213> ORGANISM: Bacillus licheniformis

<400> SEQUENCE: 4

```
Leu Thr Gly Gln Leu Val Gln Tyr Gly Arg His Arg Gln Arg Arg Ser
1               5                   10                  15

Tyr Ala Arg Ile Ser Glu Val Leu Glu Leu Pro Asn Leu Ile Glu Ile
            20                  25                  30

Gln Thr Ser Ser Tyr Gln Trp Phe Leu Asp Glu Gly Leu Arg Glu Met
        35                  40                  45

Phe Gln Asp Ile Ser Pro Ile Glu Asp Phe Thr Gly Asn Leu Ser Leu
    50                  55                  60

Glu Phe Ile Asp Tyr Ser Leu Gly Glu Pro Lys Tyr Pro Val Glu Glu
65                  70                  75                  80

Ser Lys Glu Arg Asp Val Thr Tyr Ser Ala Pro Leu Arg Val Lys Val
                85                  90                  95

Arg Leu Ile Asn Lys Glu Thr Gly Glu Val Lys Asp Gln Asp Val Phe
            100                 105                 110

Met Gly Asp Phe Pro Ile Met Thr Asp Thr Gly Thr Phe Ile Ile Asn
        115                 120                 125

Gly Ala Glu Arg Val Ile Val Ser Gln Leu Val Arg Ser Pro Ser Val
    130                 135                 140

Tyr Phe Ser Gly Lys Val Asp Lys Asn Gly Lys Lys Gly Phe Thr Ala
145                 150                 155                 160

Thr Val Ile Pro Asn Arg Gly Ala Trp Leu Glu Tyr Glu Thr Asp Ala
                165                 170                 175

Lys Asp Val Val Tyr Val Arg Ile Asp Arg Thr Arg Lys Leu Pro Val
            180                 185                 190

Thr Val Leu Leu Arg Ala Leu Gly Phe Gly Ser Asp Gln Glu Ile Ile
        195                 200                 205
```

```
Asp Leu Ile Gly Glu Asn Glu Tyr Leu Arg Asn Thr Leu Asp Lys Asp
    210                 215                 220

Asn Thr Glu Asn Thr Asp Lys Ala Leu Leu Glu Ile Tyr Glu Arg Leu
225                 230                 235                 240

Arg Pro Gly Glu Pro Pro Thr Val Glu Asn Ala Lys Ser Leu Leu Asp
                245                 250                 255

Ser Arg Phe Phe Asp Pro Lys Arg Tyr Asp Leu Ala Ser Val Gly Arg
            260                 265                 270

Tyr Lys Ile Asn Lys Lys Leu His Ile Lys Asn Arg Leu Phe Asn Gln
        275                 280                 285

Arg Leu Ala Glu Thr Leu Val Asp Pro Glu Thr Gly Glu Ile Leu Ala
290                 295                 300

Glu Lys Gly Ala Ile Leu Asp Arg Arg Thr Leu Asp Lys Val Leu Pro
305                 310                 315                 320

Tyr Leu Glu Asn Gly Ile Gly Phe Lys Lys Leu Tyr Pro Asn Gly Gly
                325                 330                 335

Val Val Glu Asp Glu Val Thr Leu Gln Ser Ile Lys Ile Tyr Ala Pro
            340                 345                 350

Thr Asp Gln Glu Gly Glu Gln Thr Ile Asn Val Ile Gly Asn Ala Tyr
        355                 360                 365

Ile Glu Glu Gly Val Lys Asn Ile Thr Pro Ser Asp Ile Ala Ser
370                 375                 380

Ile Ser Tyr Phe Phe Asn Leu Leu His Gly Val Gly Asp Thr Asp Asp
385                 390                 395                 400

Ile Asp His Leu Gly Asn Arg Arg Leu Arg Ser Val Gly Glu Leu Leu
                405                 410                 415

Gln Asn Gln Phe Arg Ile Gly Leu Ser Arg Met Glu Arg Val Val Arg
            420                 425                 430

Glu Arg Met Ser Ile Gln Asp Thr Asn Thr Ile Thr Pro Gln Gln Leu
        435                 440                 445

Ile Asn Ile Arg Pro Val Ile Ala Ser Ile Lys Glu Phe Phe Gly Ser
450                 455                 460

Ser Gln Leu Ser Gln Phe Met Asp Gln Thr Asn Pro Leu Val Glu Leu
465                 470                 475                 480

Thr His Lys Arg Arg Leu Ser Ala Leu Gly Pro Gly Gly Leu Thr Arg
                485                 490                 495

Glu Arg Ala Gly Met Glu Val Arg Asp Val His Tyr Ser His Tyr Gly
            500                 505                 510

Arg Met Cys Pro Ile Glu Thr Pro Glu Gly Pro Asn Ile Gly Leu Ile
        515                 520                 525

Asn Ser Leu Ser Ser Phe Ala Lys Val Asn Arg Phe Gly Phe Ile Glu
530                 535                 540

Thr Pro Tyr Arg Arg Val Asp Pro Glu Thr Gly Lys Val Thr Pro Arg
545                 550                 555                 560

Ile Asp Tyr Leu Thr Ala Asp Glu Glu Asp Asn Tyr Val Val Ala Gln
                565                 570                 575

Ala Asn Ala Arg Leu Asn Asp Asp Gly Ser Phe Val Asp Asp Ser Ile
            580                 585                 590

Val Ala Arg Phe Arg Gly Glu Asn Thr Val Val Pro Lys Asp Arg Val
        595                 600                 605

Asp Tyr Met Asp Val Ser Pro Lys Gln Val Val Ser Ala Ala Thr Ala
610                 615                 620

Cys Ile Pro Phe Leu Glu Asn Asp Asp Ser Asn Arg Ala Leu Met Gly
```

```
            625                 630                 635                 640
Ala Asn Met Gln Arg Gln Ala Val Pro Leu Met Gln Pro Glu Ser Pro
                        645                 650                 655
Ile Val Gly Thr Gly Met Glu Tyr Val Ser Ala Lys Asp Ser Gly Ala
                        660                 665                 670
Ala Val Ile Cys Arg His Pro Gly Ile Val Glu Arg Val Glu Ala Lys
                        675                 680                 685
Asn Ile Trp Val Arg Arg Tyr Glu Glu Val Asp Gly Gln Lys Val Lys
                        690                 695                 700
Gly Asn Leu Asp Lys Tyr Ser Leu Leu Lys Phe Val Arg Ser Asn Gln
705                 710                 715                 720
Gly Thr Cys Tyr Asn Gln Arg Pro Ile Val Ser Val Gly Asp Glu Val
                        725                 730                 735
Glu Lys Gly Glu Ile Leu Ala Asp Gly Pro Ser Met Glu Lys Gly Glu
                        740                 745                 750
Leu Ala Leu Gly Arg Asn Val Met Val Gly Phe Met Thr Trp Asp Gly
                        755                 760                 765
Tyr Asn Tyr Glu Asp Ala Ile Ile Met Ser Glu Arg Leu Val Lys Asp
                        770                 775                 780
Asp Val Tyr Thr Ser Ile His Ile Glu Glu Tyr Glu Ser Glu Ala Arg
785                 790                 795                 800
Asp Thr Lys Leu Gly Pro Glu Glu Ile Thr Arg Asp Ile Pro Asn Val
                        805                 810                 815
Gly Glu Asp Ala Leu Arg Asn Leu Asp Glu Arg Gly Ile Ile Arg Val
                        820                 825                 830
Gly Ala Glu Val Lys Asp Gly Asp Leu Leu Val Gly Lys Val Thr Pro
                        835                 840                 845
Lys Gly Val Thr Glu Leu Thr Ala Glu Glu Arg Leu Leu His Ala Ile
                        850                 855                 860
Phe Gly Glu Lys Ala Arg Glu Val Arg Asp Thr Ser Leu Arg Val Pro
865                 870                 875                 880
His Gly Gly Gly Gly Ile Ile Leu Asp Val Lys Val Phe Asn Arg Glu
                        885                 890                 895
Asp Gly Asp Glu Leu Pro Pro Gly Val Asn Gln Leu Val Arg Val Tyr
                        900                 905                 910
Ile Val Gln Lys Arg Lys Ile Ser Glu Gly Asp Lys Met Ala Gly Arg
                        915                 920                 925
His Gly Asn Lys Gly Val Ile Ser Lys Ile Leu Pro Glu Glu Asp Met
                        930                 935                 940
Pro Tyr Leu Pro Asp Gly Thr Pro Ile Asp Ile Met Leu Asn Pro Leu
945                 950                 955                 960
Gly Val Pro Ser Arg Met Asn Ile Gly Gln Val Leu Glu Leu His Leu
                        965                 970                 975
Gly Met Ala Ala Arg Arg Leu Gly Leu His Val Ala Ser Pro Val Phe
                        980                 985                 990
Asp Gly Ala Arg Glu Glu Asp Val Trp Glu Thr Leu Glu Glu Ala Gly
                        995                 1000                1005
Met Ser Arg Asp Ala Lys Thr Val Leu Tyr Asp Gly Arg Thr Gly
        1010                1015                1020
Glu Pro Phe Asp Asn Arg Val Ser Val Gly Ile Met Tyr Met Ile
        1025                1030                1035
Lys Leu Ala His Met Val Asp Asp Lys Leu His Ala Arg Ser Thr
        1040                1045                1050
```

Gly Pro Tyr Ser Leu Val Thr Gln Gln Pro Leu Gly Gly Lys Ala
   1055                1060                1065

Gln Phe Gly Gly Gln Arg Phe Gly Glu Met Glu Val Trp Ala Leu
   1070                1075                1080

Glu Ala Tyr Gly Ala Ala Tyr Thr Leu Gln Glu Ile Leu Thr Val
   1085                1090                1095

Lys Ser Asp Asp Val Val Gly Arg Val Lys Thr Tyr Glu Ala Ile
   1100                1105                1110

Val Lys Gly Asp Asn Val Pro Glu Pro Gly Val Pro Glu Ser Phe
   1115                1120                1125

Lys Val Leu Ile Lys Glu Leu Gln Ser Leu Gly Met Asp Val Lys
   1130                1135                1140

Ile Leu Ser Ser Asp Glu Glu Ile Glu Met Arg Asp Leu Glu
   1145                1150                1155

Asp Asp Glu Asp Ala Lys Gln Asn Glu Gly Leu Ser Leu Pro Asn
   1160                1165                1170

Asp Glu Glu Ser Glu Glu Leu Val Ser Ala Asp Ala Glu Arg Asp
   1175                1180                1185

Val Val Thr Lys Glu
   1190

<210> SEQ ID NO 5
<211> LENGTH: 3600
<212> TYPE: DNA
<213> ORGANISM: Bacillus subtilis

<400> SEQUENCE: 5
ttgctagatg tgaacaattt tgagtatatg aacatcggtc ttgcttcacc agataaaatc      60
cgttcatggt cttttggtga agtgaaaaag cctgaaacga taaactatcg tacgttaaaa     120
cctgaaaagg acggtctatt ctgcgaacgc attttcggac cgactaagga ctgggaatgt     180
cattgcggga agtacaagcg agttcgttat aaaggcgtag tttgtgaccg ctgcggagtc     240
gaagtaacac gggctaaagt ccgtcgtgag agaatggggc acattgaact ggctgcccca     300
gtttcccaca tttggtattt caaaggtatt ccaagccgta tgggtcttgt gctggatatg     360
tcacctcgtg cttagaaga agtcatttac tttgcttctt acgttgtaac tgatccggcg     420
aatacaccgc ttgaaaagaa acagcttctg tctgagaaga ataccgtgc ttatcttgat     480 aaatacggta taaattcca agcatctatg ggtgctgaag caattcataa acttcttcaa     540
gatatcgatc ttgtaaaaga agttgatatg ttaaagaag agctgaaaac ttcacaagga     600
caacgccgta tccgtgcgat caaacgtctt gaagttttag aagccttccg taactcagga     660
aacaagcctt cttggatgat ccttgatgtg cttcctgtta ttcctccgga gcttagaccg     720
atggttcagc tagatggcgg acgttttgcg acttctgatt tgaatgacct ttatcgtcgt     780
gtcatcaacc gtaacaatcg tttgaaacgc cttttggacc ttggtgcgcc tagcatcatc     840
gttcaaaacg aaaagcgtat gcttcaagag gctgtcgatg ccctaattga caacggccgc     900
cgcggacgcc ctgtaacagg tcctggaaac agaccgttaa atctctttc tcacatgctg     960 aaagggaagc aaggccgttt ccgtcaaaac cttcttggta acgtgtcga ttactccgga    1020 cgttctgtaa tcgttgttgg tcctcatttg aaaatgtacc aatgcggatt accgaaggaa    1080
atggcacttg aacttttcaa acctttcgtt atgaaagaac ttgttgaaaa aggtcttgct    1140
cacaacatta gagtgcgaa acgcaaaatt gagcgcgtac agcctgaagt ttgggatgta    1200

```
ctagaatcag ttattaagga gcatccggta ctgctgaacc gtgccctac  acttcacaga   1260 ttaggtatcc aggcgtttga accaacgctt gttgaaggac gcgcaatccg tcttcacccg   1320
ctcgtatgta cagcttacaa cgctgacttt gacggtgacc aaatggcggt tcacgtacca   1380
ttatctgctg aagcacaagc tgaagcacgc atcttgatgc ttgctgctca aaacatcttg   1440
aaccctaaag atggtaaacc ggttgtaaca ccgtctcagg atatggtact aggtaactat   1500
tacctgacac ttgagcgtgc cggtgctgtc ggtgaaggta tggtcttcaa gaatacagac   1560
gaagcgcttc ttgcttatca aaacggatat gttcaccttc atacgagagt agctgttgca   1620
gctaactcac ttaagaatgt gacatttacc gaagaacagc gctcaaaatt gttaattaca   1680
actgtcggta agcttgtctt caatgaaatt cttccggaat cattcccctta catgaatgaa   1740 ccaacgaaga gcaacattga agagaaaaca cctgaccgtt tcttcttaga aaaaggtgct   1800
gatgttaaag ctgttatcgc acagcagcca atcaatgcgc cgtttaaaaa aggcattctg   1860
ggtaaaatca tcgcggaaat ctttaaacga ttccatatta cggaaacgtc taaaatgctt   1920
gaccgcatga aaaacctagg tttcaaatat tcaactaaag ctggtattac agttggggtt   1980
tctgacatcg tcgtactcga tgataaacaa gaaattcttg aggaagcgca aagcaaagtt   2040
gacaacgtta tgaagcaatt ccgccgcggt cttatcactg aagaagaacg ctatgagaga   2100
gtcatctcta tctggagtgc tgcaaaagac gttatccaag gcaaactgat gaaatcactt   2160
gatgaactca acccgatcta catgatgagt gactctggtg cccgtggtaa cgcatctaac   2220
tttacgcagc ttgccggaat gcgcggcctg atggccaacc cggctggacg tatcattgag   2280
ttgccgatca aatcaagttt ccgtgaaggt ctgacagtat ggagtactt  tatctccaca   2340 cacggtgcgc gtaaaggtct tgccgatacc gctcttaaaa ctgctgactc aggttaccat   2400
acacgccgtc tcgttgacgt tgctcaggat gttatcatcc gtgaaactga ttgcggaact   2460
gaccgaggca ttcttgctaa gcctcttaaa gaaggaactg aaacaattga gcgcttagaa   2520
gaacgcttaa tcggacgttt tgcaagaaaa caagtgaagc accctgaaac aggtgaagtg   2580
cttgtgaatg aaaacgaact gatcgatgaa gataaagcac tggagattgt cgaagccggc   2640
attgaagaag tgtggatccg ttctgccttc acatgtaata cgcctcatgg tgtatgtaaa   2700
cgatgctatg gccgaaatct tgcaactggc tccgatgttg aagtcggtga agctgtcgga   2760
atcattgctg cccaatcaat cggtgagcct ggtacacagt taacaatgcg tacattccat   2820
acaggcgggg ttgccggaga cgatatcaca cagggtcttc cgcgtatcca agagcttttc   2880
gaagcgcgta atccgaaagg tcaggcaaca attacagaaa tcgacggtac agtcgttgag   2940
atcaatgaag ttcgtgataa gcaacaggaa attgtggttc aaggcgcagt ggaaacacgt   3000
tcttatacgg caccttacaa ctcccgcctg aaagtagcgg aaggagataa aattactcga   3060
ggccaagtac tgacagaagg ttcaatcgat ccgaaagaac ttcttaaagt gactgaccctg  3120 acgactgttc aagagtatct tctccatgag gttcaaaagg tttaccgtat gcagggtgtt   3180
gaaatcggtg ataaacacgt agaagtaatg gttcgccaga tgcttcgcaa agtacgcgtg   3240
attgatgccg gtgacactga tgtgcttcca ggtacattgc ttgatattca ccaatttact   3300
gaagcgaaca aaaggtatt  gcttgaaggc aaccgaccag ctacaggccg tcctgtctta   3360
ctcggtatta caaaagcatc tcttgaaact gattcattct tatctgctgc ttccttccag   3420
gaaacaacac gtgtccttac agatgcagcg atcaaaggta agcgtgacga gcttctcggc   3480
ttgaaagaga atgttatcat cggtaagctt gttccagcag gtacaggaat gatgaaatac   3540
cgtaaagtaa aaccagtatc aaatgttcag ccgactgacg atatggtccc ggttgaataa   3600
```

<210> SEQ ID NO 6
<211> LENGTH: 1199
<212> TYPE: PRT
<213> ORGANISM: Bacillus subtilis

<400> SEQUENCE: 6

```
Met Leu Asp Val Asn Asn Phe Glu Tyr Met Asn Ile Gly Leu Ala Ser
1               5                   10                  15

Pro Asp Lys Ile Arg Ser Trp Ser Phe Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Thr Lys Asp Trp Glu Cys His Cys Gly Lys
    50                  55                  60

Tyr Lys Arg Val Arg Tyr Lys Gly Val Val Cys Asp Arg Cys Gly Val
65                  70                  75                  80

Glu Val Thr Arg Ala Lys Val Arg Arg Glu Arg Met Gly His Ile Glu
                85                  90                  95

Leu Ala Ala Pro Val Ser His Ile Trp Tyr Phe Lys Gly Ile Pro Ser
            100                 105                 110

Arg Met Gly Leu Val Leu Asp Met Ser Pro Arg Ala Leu Glu Glu Val
        115                 120                 125

Ile Tyr Phe Ala Ser Tyr Val Val Thr Asp Pro Ala Asn Thr Pro Leu
    130                 135                 140

Glu Lys Lys Gln Leu Leu Ser Glu Lys Glu Tyr Arg Ala Tyr Leu Asp
145                 150                 155                 160

Lys Tyr Gly Asn Lys Phe Gln Ala Ser Met Gly Ala Glu Ala Ile His
                165                 170                 175

Lys Leu Leu Gln Asp Ile Asp Leu Val Lys Glu Val Asp Met Leu Lys
            180                 185                 190

Glu Glu Leu Lys Thr Ser Gln Gly Gln Arg Arg Thr Arg Ala Ile Lys
        195                 200                 205

Arg Leu Glu Val Leu Glu Ala Phe Arg Asn Ser Gly Asn Lys Pro Ser
    210                 215                 220

Trp Met Ile Leu Asp Val Leu Pro Val Ile Pro Pro Glu Leu Arg Pro
225                 230                 235                 240

Met Val Gln Leu Asp Gly Gly Arg Phe Ala Thr Ser Asp Leu Asn Asp
                245                 250                 255

Leu Tyr Arg Arg Val Ile Asn Arg Asn Asn Arg Leu Lys Arg Leu Leu
            260                 265                 270

Asp Leu Gly Ala Pro Ser Ile Ile Val Gln Asn Glu Lys Arg Met Leu
        275                 280                 285

Gln Glu Ala Val Asp Ala Leu Ile Asp Asn Gly Arg Arg Gly Arg Pro
    290                 295                 300

Val Thr Gly Pro Gly Asn Arg Pro Leu Lys Ser Leu Ser His Met Leu
305                 310                 315                 320

Lys Gly Lys Gln Gly Arg Phe Arg Gln Asn Leu Leu Gly Lys Arg Val
                325                 330                 335

Asp Tyr Ser Gly Arg Ser Val Ile Val Val Gly Pro His Leu Lys Met
            340                 345                 350

Tyr Gln Cys Gly Leu Pro Lys Glu Met Ala Leu Glu Leu Phe Lys Pro
        355                 360                 365

Phe Val Met Lys Glu Leu Val Glu Lys Gly Leu Ala His Asn Ile Lys
```

```
              370                 375                 380
Ser Ala Lys Arg Lys Ile Glu Arg Val Gln Pro Glu Val Trp Asp Val
385                 390                 395                 400

Leu Glu Ser Val Ile Lys Glu His Pro Val Leu Leu Asn Arg Ala Pro
                405                 410                 415

Thr Leu His Arg Leu Gly Ile Gln Ala Phe Glu Pro Thr Leu Val Glu
            420                 425                 430

Gly Arg Ala Ile Arg Leu His Pro Leu Val Cys Thr Ala Tyr Asn Ala
            435                 440                 445

Asp Phe Asp Gly Asp Gln Met Ala Val His Val Pro Leu Ser Ala Glu
        450                 455                 460

Ala Gln Ala Glu Ala Arg Ile Leu Met Leu Ala Ala Gln Asn Ile Leu
465                 470                 475                 480

Asn Pro Lys Asp Gly Lys Pro Val Val Thr Pro Ser Gln Asp Met Val
                485                 490                 495

Leu Gly Asn Tyr Tyr Leu Thr Leu Glu Arg Ala Gly Ala Val Gly Glu
                500                 505                 510

Gly Met Val Phe Lys Asn Thr Asp Glu Ala Leu Leu Ala Tyr Gln Asn
            515                 520                 525

Gly Tyr Val His Leu His Thr Arg Val Ala Val Ala Ala Asn Ser Leu
        530                 535                 540

Lys Asn Val Thr Phe Thr Glu Glu Gln Arg Ser Lys Leu Leu Ile Thr
545                 550                 555                 560

Thr Val Gly Lys Leu Val Phe Asn Glu Ile Leu Pro Glu Ser Phe Pro
                565                 570                 575

Tyr Met Asn Glu Pro Thr Lys Ser Asn Ile Glu Glu Lys Thr Pro Asp
                580                 585                 590

Arg Phe Phe Leu Glu Lys Gly Ala Asp Val Lys Ala Val Ile Ala Gln
            595                 600                 605

Gln Pro Ile Asn Ala Pro Phe Lys Lys Gly Ile Leu Gly Lys Ile Ile
        610                 615                 620

Ala Glu Ile Phe Lys Arg Phe His Ile Thr Glu Thr Ser Lys Met Leu
625                 630                 635                 640

Asp Arg Met Lys Asn Leu Gly Phe Lys Tyr Ser Thr Lys Ala Gly Ile
                645                 650                 655

Thr Val Gly Val Ser Asp Ile Val Val Leu Asp Asp Lys Gln Glu Ile
                660                 665                 670

Leu Glu Glu Ala Gln Ser Lys Val Asp Asn Val Met Lys Gln Phe Arg
            675                 680                 685

Arg Gly Leu Ile Thr Glu Glu Arg Tyr Glu Arg Val Ile Ser Ile
        690                 695                 700

Trp Ser Ala Ala Lys Asp Val Ile Gln Gly Leu Met Lys Ser Leu
705                 710                 715                 720

Asp Glu Leu Asn Pro Ile Tyr Met Met Ser Asp Ser Gly Ala Arg Gly
                725                 730                 735

Asn Ala Ser Asn Phe Thr Gln Leu Ala Gly Met Arg Gly Leu Met Ala
            740                 745                 750

Asn Pro Ala Gly Arg Ile Ile Glu Leu Pro Ile Lys Ser Ser Phe Arg
        755                 760                 765

Glu Gly Leu Thr Val Leu Glu Tyr Phe Ile Ser Thr His Gly Ala Arg
    770                 775                 780

Lys Gly Leu Ala Asp Thr Ala Leu Lys Thr Ala Asp Ser Gly Tyr Leu
785                 790                 795                 800
```

```
Thr Arg Arg Leu Val Asp Val Ala Gln Asp Val Ile Ile Arg Glu Thr
            805                 810                 815
Asp Cys Gly Thr Asp Arg Gly Ile Leu Ala Lys Pro Leu Lys Glu Gly
            820                 825                 830
Thr Glu Thr Ile Glu Arg Leu Glu Glu Arg Leu Ile Gly Arg Phe Ala
            835                 840                 845
Arg Lys Gln Val Lys His Pro Glu Thr Gly Glu Val Leu Val Asn Glu
850                 855                 860
Asn Glu Leu Ile Asp Glu Asp Lys Ala Leu Glu Ile Val Glu Ala Gly
865                 870                 875                 880
Ile Glu Glu Val Trp Ile Arg Ser Ala Phe Thr Cys Asn Thr Pro His
            885                 890                 895
Gly Val Cys Lys Arg Cys Tyr Gly Arg Asn Leu Ala Thr Gly Ser Asp
            900                 905                 910
Val Glu Val Gly Glu Ala Val Gly Ile Ile Ala Ala Gln Ser Ile Gly
            915                 920                 925
Glu Pro Gly Thr Gln Leu Thr Met Arg Thr Phe His Thr Gly Gly Val
            930                 935                 940
Ala Gly Asp Asp Ile Thr Gln Gly Leu Pro Arg Ile Gln Glu Leu Phe
945                 950                 955                 960
Glu Ala Arg Asn Pro Lys Gly Gln Ala Thr Ile Thr Glu Ile Asp Gly
            965                 970                 975
Thr Val Val Glu Ile Asn Glu Val Arg Asp Lys Gln Gln Glu Ile Val
            980                 985                 990
Val Gln Gly Ala Val Glu Thr Arg Ser Tyr Thr Ala Pro Tyr Asn Ser
            995                 1000                1005
Arg Leu Lys Val Ala Glu Gly Asp Lys Ile Thr Arg Gly Gln Val
    1010                1015                1020
Leu Thr Glu Gly Ser Ile Asp Pro Lys Glu Leu Leu Lys Val Thr
    1025                1030                1035
Asp Leu Thr Thr Val Gln Glu Tyr Leu Leu His Glu Val Gln Lys
    1040                1045                1050
Val Tyr Arg Met Gln Gly Val Glu Ile Gly Asp Lys His Val Glu
    1055                1060                1065
Val Met Val Arg Gln Met Leu Arg Lys Val Arg Val Ile Asp Ala
    1070                1075                1080
Gly Asp Thr Asp Val Leu Pro Gly Thr Leu Leu Asp Ile His Gln
    1085                1090                1095
Phe Thr Glu Ala Asn Lys Lys Val Leu Leu Glu Gly Asn Arg Pro
    1100                1105                1110
Ala Thr Gly Arg Pro Val Leu Leu Gly Ile Thr Lys Ala Ser Leu
    1115                1120                1125
Glu Thr Asp Ser Phe Leu Ser Ala Ala Ser Phe Gln Glu Thr Thr
    1130                1135                1140
Arg Val Leu Thr Asp Ala Ala Ile Lys Gly Lys Arg Asp Glu Leu
    1145                1150                1155
Leu Gly Leu Lys Glu Asn Val Ile Ile Gly Lys Leu Val Pro Ala
    1160                1165                1170
Gly Thr Gly Met Met Lys Tyr Arg Lys Val Lys Pro Val Ser Asn
    1175                1180                1185
Val Gln Pro Thr Asp Asp Met Val Pro Val Glu
    1190                1195
```

<210> SEQ ID NO 7
<211> LENGTH: 3600
<212> TYPE: DNA
<213> ORGANISM: Bacillus licheniformis

<400> SEQUENCE: 7

| | | | | | |
|---|---|---|---|---|---|
| ttgctggatg | tgaacaattt | tgagtatatg | aacatcggtc | tcgcttcacc | tgacaaaatc | 60 |
| cgttcatggt | cttacggaga | agtgaaaaag | cctgaaacaa | tcaactatcg | tactttgaaa | 120 |
| cctgaaaaag | atggtctatt | ctgcgagcgc | attttcggtc | ctcaaaagga | ctgggaatgc | 180 |
| cactgcggaa | agtacaagcg | ggttcgttat | aaaggcgtag | tctgcgaccg | ttgtggagtt | 240 |
| gaagtaaccc | gggctaaagt | ccgtcgtgag | agaatggggc | atatcgagct | ggcagccccg | 300 |
| gtttctcaca | tctggtattt | taaaggaatt | ccgagccgta | tgggtcttgt | gctggatatg | 360 |
| tctccgcgcg | cattggaaga | agtcatttac | tttgcttctt | acgtcgtaac | agatccggcc | 420 |
| aatacaccgc | tcgagaaaaa | acagcttctt | tctgaaaaag | agtatcgggc | gtacctcgat | 480 |
| aaatacggaa | ataaattcca | agcgtcaatg | ggtgctgaag | cgattcataa | gctccttcaa | 540 |
| gatatcgacc | tcgataaaga | agtggatatg | ctgaaagaag | agcttaaaac | gtcacaagga | 600 |
| cagcgccgca | cacgtgcgat | caaacgtctg | gaagtattgg | aagccttccg | caattccgga | 660 |
| aataagccgt | catggatgat | cctcgacgtt | cttccggtca | ttccgcctga | gctgcgacca | 720 |
| atggtacagc | ttgacggtgg | acgttttgca | acttccgatc | tgaacgattt | gtatcgccgc | 780 |
| gtaatcaacc | gtaacaatcg | tttaaaacgt | cttctggacc | ttggagcgcc | aagcattatc | 840 |
| gttcaaaacg | aaaagcgcat | gcttcaggaa | gccgtggacg | cattgatcga | taacggacgc | 900 |
| agaggacgtc | ctgttacagg | tccaggaaac | agaccgttaa | aatccctttc | tcacatgctg | 960 |
| aaaggtaaac | aaggccattt | ccgtcaaaac | cttctcggta | acgtgttgga | ctactcagga | 1020 |
| cgttcggtta | tcgtcgtagg | tccgaacctg | aaaatgtatc | aatgcggtct | tccgaaagaa | 1080 |
| atggcgctgg | aactgttcaa | gccattcgtc | atgaaagagc | ttgttgaaaa | gggccttgcc | 1140 |
| cacaatatta | agagcgcgaa | gcgtaaaatt | gagcgcgttc | agccggaagt | ctgggatgtc | 1200 |
| cttgaatcag | ttatcaaaga | acaccctgtg | cttctcaacc | gtgcacctac | gcttcacaga | 1260 |
| ttaggtattc | aagcgtttga | accaacgctt | gttgaaggcc | gtgccatccg | tcttcatccg | 1320 |
| cttgtatgta | cggcatacaa | cgctgacttt | gacggtgacc | aaatggcggt | tcacgttcct | 1380 |
| ttatcagcag | aagcgcaagc | tgaggcgcgc | atccttatgc | ttgctgcgca | aacatcctg | 1440 |
| aaccctaaag | acgaaaaacc | ggttgttaca | ccgtctcagg | atatggtact | tggaaactac | 1500 |
| tatctgacgc | tagaacgccc | tggtgcagtc | ggcgaaggta | tgattttcaa | agatacggat | 1560 |
| gaagcgctgc | ttgcttacca | aaacggatat | gttcatttgc | atacgagagt | agccgtcgcg | 1620 |
| gttaactcat | tgaaaaatga | aacgtttacc | gaagaacagc | gttccaagct | gctcattaca | 1680 |
| actgtcggaa | aactgatctt | caacgaaatt | cttccgccgt | cgttcccata | catgaacgaa | 1740 |
| ccgacgaaga | gcaacattga | agaaaaaacg | cctgaccgtt | tcttcttgga | ttacggtgca | 1800 |
| gatgttaaag | aagccattaa | gaaccaagaa | atcaacccgc | cgttcaaaaa | aggcattttg | 1860 |
| ggtaaaatca | ttgcggagat | cttcaaaagg | ttccatatta | cagaaacatc | aaaaatgctt | 1920 |
| gaccgcatga | aaaacctcgg | ctttaaatac | tctacaaaag | ccggaattac | ggtcggtgtt | 1980 |
| tccgatatcg | tcgtattgga | cgacaaacag | gaaatccttg | aagaagcgca | aggaaaagtc | 2040 |
| gataacgtga | tgaagcagtt | cagacgcggt | ctgattactg | aagaagagcg | ttatgaacgg | 2100 |
| gtcatttcca | tctggagtgc | agctaaggat | acgatccaag | gcaagctgat | gaaatccttg | 2160 |

```
gatgaaatca acccgatcta catgatgagt gattccggag cccggggtaa cgcatcaaac    2220
tttacgcagc ttgcgggtat gcgcggtctg atggccaacc cggccggacg gatcatcgaa    2280
cttccgatca agtcaagttt ccgtgaaggt ttaacggtac tcgagtactt tatctctact    2340
cacggtgcgc gtaaaggtct tgcggatacg gcccttaaga cagccgactc aggttacctg    2400
acacgccgtc tcgtagacgt agcccaagac gtcatcattc gtgagactga ctgcggcaca    2460
gaccgaggca ttcttgccaa agccatcacg gaaggcacag aagtgatcga gcgtcttgaa    2520
gagcgtcttg tcggccgatt cgcgagaaag cctgttaaac atccggaaac aggtgaagtg    2580
ctcgtgaatg aaaacgagct gatcgacgaa gataaagcga ttgaaattgt cgaagcaggc    2640
attgaagaag tgtggatccg ctccgcattt acatgtaata cgtcacatgg tgtatgtaaa    2700
cgatgctacg gccgcaacct ggcaacagga accgatgtcg aagtcggaga agcagtcgga    2760
atcatcgctg cccagtccat ggtgagccg gtacacagt taacgatgcg taccttccat    2820
acgggcgggg ttgccggaga cgatattaca caaggtttgc cgcgtatcca ggaattgttt    2880
gaagcgcgaa accctaaagg tcaagcgacg atctctgaaa ttgacggtgt cgtggccgaa    2940
atcaatgagg ttcgcgataa acagcaggaa atcgtcgttc agggcgaagt cgaaagccgt    3000
tcatatacgg cgccttacaa cgcgcgcttg aaagtcactg aaggagagaa gatttctcgt    3060
ggtcaagtgc tgacagaagg ttcggttgat ccgaaagagc ttctgaaagt cactgacatc    3120
accacggtcc aagaatacct gcttcatgaa gtgcagaagg tttatcgtat gcaggggtt    3180 gaaatcggag ataagcacgt cgaggttatg gttcgccaga tgcttcgcaa agtgcgcgtc    3240
atcgatgccg gcgacacgga agtgctgcca ggcacgctgc tcgatattca ccagtttaca    3300
gaagcaaaca aaaagttct gcttgaaggc aaacgccctg caactggccg tccggtgctt    3360
ctcggtatca ccaaagcatc gcttgaaacg gattccttcc tgtctgccgc gtcattccag    3420
gaaacaacac gtgtcctgac agatgcagcg atcaaaggaa aacgtgacga gcttctcggc    3480
ctgaaagaga atgttatcat cggtaagctt gttcctgctg aacgggtat gctgaactat    3540 cgtaaagtga agccggtatt gcaagtccaa tcatctgatg aaatggttcc ggctgaataa    3600
```

<210> SEQ ID NO 8
<211> LENGTH: 1199
<212> TYPE: PRT
<213> ORGANISM: Bacillus licheniformis

<400> SEQUENCE: 8

```
Met Leu Asp Val Asn Asn Phe Glu Tyr Met Asn Ile Gly Leu Ala Ser
1               5                   10                  15

Pro Asp Lys Ile Arg Ser Trp Ser Tyr Gly Glu Val Lys Lys Pro Glu
            20                  25                  30

Thr Ile Asn Tyr Arg Thr Leu Lys Pro Glu Lys Asp Gly Leu Phe Cys
        35                  40                  45

Glu Arg Ile Phe Gly Pro Gln Lys Asp Trp Glu Cys His Cys Gly Lys
    50                  55                  60

Tyr Lys Arg Val Arg Tyr Lys Gly Val Val Cys Asp Arg Cys Gly Val
65                  70                  75                  80

Glu Val Thr Arg Ala Lys Val Arg Arg Glu Arg Met Gly His Ile Glu
                85                  90                  95

Leu Ala Ala Pro Val Ser His Ile Trp Tyr Phe Lys Gly Ile Pro Ser
            100                 105                 110

Arg Met Gly Leu Val Leu Asp Met Ser Pro Arg Ala Leu Glu Glu Val
```

```
            115                 120                 125
Ile Tyr Phe Ala Ser Tyr Val Val Thr Asp Pro Ala Asn Thr Pro Leu
130                 135                 140

Glu Lys Lys Gln Leu Leu Ser Glu Lys Glu Tyr Arg Ala Tyr Leu Asp
145                 150                 155                 160

Lys Tyr Gly Asn Lys Phe Gln Ala Ser Met Gly Ala Glu Ala Ile His
                165                 170                 175

Lys Leu Leu Gln Asp Ile Asp Leu Asp Lys Glu Val Asp Met Leu Lys
                180                 185                 190

Glu Glu Leu Lys Thr Ser Gln Gly Gln Arg Arg Thr Arg Ala Ile Lys
                195                 200                 205

Arg Leu Glu Val Leu Glu Ala Phe Arg Asn Ser Gly Asn Lys Pro Ser
210                 215                 220

Trp Met Ile Leu Asp Val Leu Pro Val Ile Pro Pro Glu Leu Arg Pro
225                 230                 235                 240

Met Val Gln Leu Asp Gly Gly Arg Phe Ala Thr Ser Asp Leu Asn Asp
                245                 250                 255

Leu Tyr Arg Arg Val Ile Asn Arg Asn Asn Arg Leu Lys Arg Leu Leu
                260                 265                 270

Asp Leu Gly Ala Pro Ser Ile Ile Val Gln Asn Glu Lys Arg Met Leu
                275                 280                 285

Gln Glu Ala Val Asp Ala Leu Ile Asp Asn Gly Arg Arg Gly Arg Pro
290                 295                 300

Val Thr Gly Pro Gly Asn Arg Pro Leu Lys Ser Leu Ser His Met Leu
305                 310                 315                 320

Lys Gly Lys Gln Gly His Phe Arg Gln Asn Leu Leu Gly Lys Arg Val
                325                 330                 335

Asp Tyr Ser Gly Arg Ser Val Ile Val Val Gly Pro Asn Leu Lys Met
                340                 345                 350

Tyr Gln Cys Gly Leu Pro Lys Glu Met Ala Leu Glu Leu Phe Lys Pro
                355                 360                 365

Phe Val Met Lys Glu Leu Val Glu Lys Gly Leu Ala His Asn Ile Lys
370                 375                 380

Ser Ala Lys Arg Lys Ile Glu Arg Val Gln Pro Glu Val Trp Asp Val
385                 390                 395                 400

Leu Glu Ser Val Ile Lys Glu His Pro Val Leu Leu Asn Arg Ala Pro
                405                 410                 415

Thr Leu His Arg Leu Gly Ile Gln Ala Phe Glu Pro Thr Leu Val Glu
                420                 425                 430

Gly Arg Ala Ile Arg Leu His Pro Leu Val Cys Thr Ala Tyr Asn Ala
                435                 440                 445

Asp Phe Asp Gly Asp Gln Met Ala Val His Val Pro Leu Ser Ala Glu
                450                 455                 460

Ala Gln Ala Glu Ala Arg Ile Leu Met Leu Ala Ala Gln Asn Ile Leu
465                 470                 475                 480

Asn Pro Lys Asp Gly Lys Pro Val Val Thr Pro Ser Gln Asp Met Val
                485                 490                 495

Leu Gly Asn Tyr Tyr Leu Thr Leu Glu Arg Pro Gly Ala Val Gly Glu
                500                 505                 510

Gly Met Ile Phe Lys Asp Thr Asp Glu Ala Leu Leu Ala Tyr Gln Asn
                515                 520                 525

Gly Tyr Val His Leu His Thr Arg Val Ala Val Ala Val Asn Ser Leu
530                 535                 540
```

```
Lys Asn Glu Thr Phe Thr Glu Glu Gln Arg Ser Lys Leu Leu Ile Thr
545                 550                 555                 560

Thr Val Gly Lys Leu Ile Phe Asn Glu Ile Leu Pro Pro Ser Phe Pro
            565                 570                 575

Tyr Met Asn Glu Pro Thr Lys Ser Asn Ile Glu Glu Lys Thr Pro Asp
        580                 585                 590

Arg Phe Phe Leu Asp Tyr Gly Ala Asp Val Lys Glu Ala Ile Lys Asn
            595                 600                 605

Gln Glu Ile Asn Pro Pro Phe Lys Lys Gly Ile Leu Gly Lys Ile Ile
        610                 615                 620

Ala Glu Ile Phe Lys Arg Phe His Ile Thr Glu Thr Ser Lys Met Leu
625                 630                 635                 640

Asp Arg Met Lys Asn Leu Gly Phe Lys Tyr Ser Thr Lys Ala Gly Ile
                645                 650                 655

Thr Val Gly Val Ser Asp Ile Val Val Leu Asp Asp Lys Gln Glu Ile
            660                 665                 670

Leu Glu Glu Ala Gln Gly Lys Val Asp Asn Val Met Lys Gln Phe Arg
        675                 680                 685

Arg Gly Leu Ile Thr Glu Glu Arg Tyr Glu Arg Val Ile Ser Ile
            690                 695                 700

Trp Ser Ala Ala Lys Asp Thr Ile Gln Gly Lys Leu Met Lys Ser Leu
705                 710                 715                 720

Asp Glu Ile Asn Pro Ile Tyr Met Met Ser Asp Ser Gly Ala Arg Gly
                725                 730                 735

Asn Ala Ser Asn Phe Thr Gln Leu Ala Gly Met Arg Gly Leu Met Ala
            740                 745                 750

Asn Pro Ala Gly Arg Ile Ile Glu Leu Pro Ile Lys Ser Ser Phe Arg
        755                 760                 765

Glu Gly Leu Thr Val Leu Glu Tyr Phe Ile Ser Thr His Gly Ala Arg
        770                 775                 780

Lys Gly Leu Ala Asp Thr Ala Leu Lys Thr Ala Asp Ser Gly Tyr Leu
785                 790                 795                 800

Thr Arg Arg Leu Val Asp Val Ala Gln Asp Val Ile Ile Arg Glu Thr
                805                 810                 815

Asp Cys Gly Thr Asp Arg Gly Ile Leu Ala Lys Ala Ile Thr Glu Gly
            820                 825                 830

Thr Glu Val Ile Glu Arg Leu Glu Glu Arg Leu Val Gly Arg Phe Ala
        835                 840                 845

Arg Lys Pro Val Lys His Pro Glu Thr Gly Glu Val Leu Val Asn Glu
        850                 855                 860

Asn Glu Leu Ile Asp Glu Asp Lys Ala Ile Glu Ile Val Glu Ala Gly
865                 870                 875                 880

Ile Glu Glu Val Trp Ile Arg Ser Ala Phe Thr Cys Asn Thr Ser His
                885                 890                 895

Gly Val Cys Lys Arg Cys Tyr Gly Arg Asn Leu Ala Thr Gly Thr Asp
            900                 905                 910

Val Glu Val Gly Glu Ala Val Gly Ile Ile Ala Ala Gln Ser Ile Gly
        915                 920                 925

Glu Pro Gly Thr Gln Leu Thr Met Arg Thr Phe His Thr Gly Gly Val
        930                 935                 940

Ala Gly Asp Asp Ile Thr Gln Gly Leu Pro Arg Ile Gln Glu Leu Phe
945                 950                 955                 960
```

-continued

Glu Ala Arg Asn Pro Lys Gly Gln Ala Thr Ile Ser Glu Ile Asp Gly
                965                 970                 975

Val Val Ala Glu Ile Asn Glu Val Arg Asp Lys Gln Gln Glu Ile Val
            980                 985                 990

Val Gln Gly Glu Val Glu Ser Arg Ser Tyr Thr Ala Pro Tyr Asn Ala
        995                 1000                1005

Arg Leu Lys Val Thr Glu Gly Glu Lys Ile Ser Arg Gly Gln Val
    1010                1015                1020

Leu Thr Glu Gly Ser Val Asp Pro Lys Glu Leu Leu Lys Val Thr
    1025                1030                1035

Asp Ile Thr Thr Val Gln Glu Tyr Leu Leu His Glu Val Gln Lys
    1040                1045                1050

Val Tyr Arg Met Gln Gly Val Glu Ile Gly Asp Lys His Val Glu
    1055                1060                1065

Val Met Val Arg Gln Met Leu Arg Lys Val Arg Val Ile Asp Ala
    1070                1075                1080

Gly Asp Thr Glu Val Leu Pro Gly Thr Leu Leu Asp Ile His Gln
    1085                1090                1095

Phe Thr Glu Ala Asn Lys Lys Val Leu Leu Glu Gly Lys Arg Pro
    1100                1105                1110

Ala Thr Gly Arg Pro Val Leu Leu Gly Ile Thr Lys Ala Ser Leu
    1115                1120                1125

Glu Thr Asp Ser Phe Leu Ser Ala Ala Ser Phe Gln Glu Thr Thr
    1130                1135                1140

Arg Val Leu Thr Asp Ala Ala Ile Lys Gly Lys Arg Asp Glu Leu
    1145                1150                1155

Leu Gly Leu Lys Glu Asn Val Ile Ile Gly Lys Leu Val Pro Ala
    1160                1165                1170

Gly Thr Gly Met Leu Asn Tyr Arg Lys Val Lys Pro Val Leu Gln
    1175                1180                1185

Val Gln Ser Ser Asp Glu Met Val Pro Ala Glu
    1190                1195

<210> SEQ ID NO 9
<211> LENGTH: 24
<212> TYPE: DNA
<213> ORGANISM: Artificial Sequence
<220> FEATURE:
<223> OTHER INFORMATION: oligonucleotide

<400> SEQUENCE: 9
cgattaggga taacagggta atat                                          24

<210> SEQ ID NO 10
<211> LENGTH: 24
<212> TYPE: DNA
<213> ORGANISM: Artificial Sequence
<220> FEATURE:
<223> OTHER INFORMATION: oligonucleotide

<400> SEQUENCE: 10
cgatattacc ctgttatccc taat                                          24

<210> SEQ ID NO 11
<211> LENGTH: 28
<212> TYPE: DNA
<213> ORGANISM: Artificial Sequence
<220> FEATURE:
<223> OTHER INFORMATION: oligonucleotide

<400> SEQUENCE: 11
tcggaattcc gagccgtatg ggtcttgt                28

<210> SEQ ID NO 12
<211> LENGTH: 30
<212> TYPE: DNA
<213> ORGANISM: Artificial Sequence
<220> FEATURE:
<223> OTHER INFORMATION: oligonucleotide

<400> SEQUENCE: 12
taagtcgact tattcagccg gaaccatttc              30

<210> SEQ ID NO 13
<211> LENGTH: 24
<212> TYPE: DNA
<213> ORGANISM: Artificial Sequence
<220> FEATURE:
<223> OTHER INFORMATION: oligonucleotide

<400> SEQUENCE: 13
ctcgtgcacc caactgatct tcag                    24

<210> SEQ ID NO 14
<211> LENGTH: 26
<212> TYPE: DNA
<213> ORGANISM: Artificial Sequence
<220> FEATURE:
<223> OTHER INFORMATION: oligonucleotide

<400> SEQUENCE: 14
ctgcgtccgt tatcgatcaa tgcgtc                  26

<210> SEQ ID NO 15
<211> LENGTH: 26
<212> TYPE: DNA
<213> ORGANISM: Artificial Sequence
<220> FEATURE:
<223> OTHER INFORMATION: oligonucleotide

<400> SEQUENCE: 15
cagctaagga tacgatccaa ggcaag                  26

<210> SEQ ID NO 16
<211> LENGTH: 25
<212> TYPE: DNA
<213> ORGANISM: Artificial Sequence
<220> FEATURE:
<223> OTHER INFORMATION: oligonucleotide

<400> SEQUENCE: 16
tcgctttatc ttcgtcgatc agctc                   25

<210> SEQ ID NO 17
<211> LENGTH: 25
<212> TYPE: DNA
<213> ORGANISM: Artificial Sequence
<220> FEATURE:
<223> OTHER INFORMATION: oligonucleotide

<400> SEQUENCE: 17
ggcaagctga tgaaatcctt ggatg                   25

<210> SEQ ID NO 18

```
<211> LENGTH: 35
<212> TYPE: DNA
<213> ORGANISM: Artificial Sequence
<220> FEATURE:
<223> OTHER INFORMATION: oligonucleotide

<400> SEQUENCE: 18
tatgcggccg catattccgc attcgcaatg cctac                              35

<210> SEQ ID NO 19
<211> LENGTH: 38
<212> TYPE: DNA
<213> ORGANISM: Artificial Sequence
<220> FEATURE:
<223> OTHER INFORMATION: oligonucleotide

<400> SEQUENCE: 19
tttgcggccg caaaataaaa aaacggattt ccttcagg                           38

<210> SEQ ID NO 20
<211> LENGTH: 40
<212> TYPE: DNA
<213> ORGANISM: Artificial Sequence
<220> FEATURE:
<223> OTHER INFORMATION: oligonucleotide

<400> SEQUENCE: 20
taaggcggat cctcttcagg aagaatctta gagataacac                         40

<210> SEQ ID NO 21
<211> LENGTH: 44
<212> TYPE: DNA
<213> ORGANISM: Artificial Sequence
<220> FEATURE:
<223> OTHER INFORMATION: oligonucleotide

<400> SEQUENCE: 21
ggttcgtctg atccatgaat ttagaaagct gtgagcttcc aaag                    44

<210> SEQ ID NO 22
<211> LENGTH: 44
<212> TYPE: DNA
<213> ORGANISM: Artificial Sequence
<220> FEATURE:
<223> OTHER INFORMATION: oligonucleotide

<400> SEQUENCE: 22
ctttggaagc tcacagcttt ctaaattcat ggatcagacg aacc                    44

<210> SEQ ID NO 23
<211> LENGTH: 60
<212> TYPE: DNA
<213> ORGANISM: Artificial Sequence
<220> FEATURE:
<223> OTHER INFORMATION: oligonucleotide

<400> SEQUENCE: 23
ctcactaatt accctgttat ccctattata actagagatt attcttttgt tactacatcg   60

<210> SEQ ID NO 24
<211> LENGTH: 44
<212> TYPE: DNA
<213> ORGANISM: Artificial Sequence
<220> FEATURE:
<223> OTHER INFORMATION: oligonucleotide

<400> SEQUENCE: 24
```
ctttggaagc tcacagctttt ctcgattcat ggatcagacg aacc    44

<210> SEQ ID NO 25
<211> LENGTH: 44
<212> TYPE: DNA
<213> ORGANISM: Artificial Sequence
<220> FEATURE:
<223> OTHER INFORMATION: oligonucleotide

<400> SEQUENCE: 25
ggttcgtctg atccatgaat cgagaaagct gtgagcttcc aaag    44

<210> SEQ ID NO 26
<211> LENGTH: 53
<212> TYPE: DNA
<213> ORGANISM: Artificial Sequence
<220> FEATURE:
<223> OTHER INFORMATION: oligonucleotide

<400> SEQUENCE: 26
gacgaacccg cttgctgaat taacgtacaa gcgtcgtctg tcagcattag gac    53

<210> SEQ ID NO 27
<211> LENGTH: 53
<212> TYPE: DNA
<213> ORGANISM: Artificial Sequence
<220> FEATURE:
<223> OTHER INFORMATION: oligonucleotide

<400> SEQUENCE: 27
gtcctaatgc tgacagacga cgcttgtacg ttaattcagc aagcgggttc gtc    53

<210> SEQ ID NO 28
<211> LENGTH: 800
<212> TYPE: DNA
<213> ORGANISM: Artificial Sequence
<220> FEATURE:
<223> OTHER INFORMATION: polynucleotide synthetic construct

<400> SEQUENCE: 28
ctctagttat aatagggata acagggtaat tagtgaggag gatatatttg aatacatacg    60
aacaaattaa taaagtgaaa aaaatacttc ggaaacatttt aaaaaataac cttattggta    120
cttacatgtt tggatcagga gttgagagtg gactaaaacc aaatagtgat cttgactttt    180
tagtcgtcgt atctgaacca ttgacagatc aaagtaaaga aatacttata caaaaaatta    240
gacctatttc aaaaaaaata ggagataaaa gcaacttacg atatattgaa ttaacaatta    300
ttattcagca agaaatggta ccgtggaatc atcctcccaa acaagaattt atttatggag    360
aatggttaca agagctttat gaacaaggat acattcctca gaaggaatta aattcagatt    420
taaccataat gctttaccaa gcaaaacgaa aaaataaaag aatatacgga aattatgact    480
tagaggaatt actacctgat attccatttt ctgatgtgag aagagccatt atggattcgt    540
cagaggaatt aatagataat tatcaggatg atgaaaccaa ctctatatta actttatgcc    600
gtatgatttt aactatggac acgggtaaaa tcataccaaa agatattgcg ggaaatgcag    660
tggctgaatc ttctccatta gaacataggg agagaatttt gttagcagtt cgtagttatc    720
ttggagagaa tattgaatgg actaatgaaa atgtaaattt aactataaac tatttaaata    780
acagattaaa aaaattataa    800

<210> SEQ ID NO 29

```
<211> LENGTH: 55
<212> TYPE: DNA
<213> ORGANISM: Artificial Sequence
<220> FEATURE:
<223> OTHER INFORMATION: oligonucleotide

<400> SEQUENCE: 29
ctatttaaat aacagattaa aaaaattata aaactggtat ggaatacgta tcagg          55

<210> SEQ ID NO 30
<211> LENGTH: 26
<212> TYPE: DNA
<213> ORGANISM: Artificial Sequence
<220> FEATURE:
<223> OTHER INFORMATION: oligonucleotide

<400> SEQUENCE: 30
gaagcaagac cgatgttcat atactc                                         26

<210> SEQ ID NO 31
<211> LENGTH: 40
<212> TYPE: PRT
<213> ORGANISM: Artificial Sequence
<220> FEATURE:
<223> OTHER INFORMATION: rpoC amino acid residue 461 through amino acid
      residue 500 of SEQ ID NO: 4 or SEQ ID NO: 6

<400> SEQUENCE: 31

Leu Ser Ala Glu Ala Gln Ala Glu Ala Arg Ile Leu Met Leu Ala Ala
1               5                  10                  15

Gln Asn Ile Leu Asn Pro Lys Asp Gly Lys Pro Val Val Thr Pro Ser
            20                  25                  30

Gln Asp Met Val Leu Gly Asn Tyr
        35                  40

<210> SEQ ID NO 32
<211> LENGTH: 34
<212> TYPE: DNA
<213> ORGANISM: Artificial Sequence
<220> FEATURE:
<223> OTHER INFORMATION: oligonucleotide

<400> SEQUENCE: 32
caagaattct tgacaggtca actagttcag tatg                                34

<210> SEQ ID NO 33
<211> LENGTH: 37
<212> TYPE: DNA
<213> ORGANISM: Artificial Sequence
<220> FEATURE:
<223> OTHER INFORMATION: oligonucleotide

<400> SEQUENCE: 33
gtagcggccg ctaccctgtc acttgcgtat aaaattc                             37

<210> SEQ ID NO 34
<211> LENGTH: 579
<212> TYPE: DNA
<213> ORGANISM: Bacillus licheniformis

<400> SEQUENCE: 34
atgagcacag aggatatgac aaaggatacg tatgaagtaa acagttcgac aatggctgtc    60
ctgcctctgg gagaggggga gaaacccgcc tcaaaaatac ttgagaccga caggactttc   120
cgcgtcaata tgaagccgtt tcaaattatc gaaagaagct gccgctattt cggatcgagc   180
```

```
tatgcgggaa gaaaagcggg cacatatgaa gtcattaaag tttcccataa accgccgatc     240
atggtggatc actcaaacaa cattttcctt ttccccacat tttcctcaac tcgtcctcag     300
tgcgggtggc tttcccatgc gcatgttcac gagttttgcg cggcaaagta tgacaacacg     360
tttgtcacgt ttgtcaacgg ggaaacgctg gagctgcccg tatccatctc atctttcgaa     420
aaccaggttt accgaacggc atggctgaga acaaaattta tcgacaggat tgaaggaaac     480
cccatgcaga gaaacagga atttatgctc tatccgaaag aagaccggaa tcagctgata      540
tacgaattca tcctcaggga gctgaaaaag cgctattga                            579
```

```
<210> SEQ ID NO 35
<211> LENGTH: 192
<212> TYPE: PRT
<213> ORGANISM: Bacillus licheniformis

<400> SEQUENCE: 35

Met Ser Thr Glu Asp Met Thr Lys Asp Thr Tyr Glu Val Asn Ser Ser
  1               5                  10                  15

Thr Met Ala Val Leu Pro Leu Gly Glu Gly Lys Pro Ala Ser Lys
             20                  25                  30

Ile Leu Glu Thr Asp Arg Thr Phe Arg Val Asn Met Lys Pro Phe Gln
         35                  40                  45

Ile Ile Glu Arg Ser Cys Arg Tyr Phe Gly Ser Tyr Ala Gly Arg
     50                  55                  60

Lys Ala Gly Thr Tyr Glu Val Ile Lys Val Ser His Lys Pro Pro Ile
 65                  70                  75                  80

Met Val Asp His Ser Asn Asn Ile Phe Leu Phe Pro Thr Phe Ser Ser
                 85                  90                  95

Thr Arg Pro Gln Cys Gly Trp Leu Ser His Ala His Val His Glu Phe
            100                 105                 110

Cys Ala Ala Lys Tyr Asp Asn Thr Phe Val Thr Phe Val Asn Gly Glu
        115                 120                 125

Thr Leu Glu Leu Pro Val Ser Ile Ser Ser Phe Glu Asn Gln Val Tyr
    130                 135                 140

Arg Thr Ala Trp Leu Arg Thr Lys Phe Ile Asp Arg Ile Glu Gly Asn
145                 150                 155                 160

Pro Met Gln Lys Lys Gln Glu Phe Met Leu Tyr Pro Lys Glu Asp Arg
                165                 170                 175

Asn Gln Leu Ile Tyr Glu Phe Ile Leu Arg Glu Leu Lys Lys Arg Tyr
            180                 185                 190
```

```
<210> SEQ ID NO 36
<211> LENGTH: 579
<212> TYPE: DNA
<213> ORGANISM: Bacillus licheniformis

<400> SEQUENCE: 36
atgagcacag aggatatgac aaaggatacg tatgaagtaa acagttcgac aatggctgtc      60
ctgcctctgg gtgaggggga gaaatccgcc tcaaaaatac ttgagaccga caggactttc     120
cgcgtcaata tgaagccgtt tcaaattatc gaaagaagct gccgctattt cggatcgagc     180
tatgcgggaa gaaaagcggg cacatatgaa gtcattaaag tttcccataa accgccgatc     240
atggtggatc actcaaacaa cattttcctt ttccccacat tttcctcaac tcgtcctcag     300
tgcgggtggc tttcccatgc gcatgttcac gagttttgcg cggcaaagta tgacaacacg     360
```

```
tttgtcacgt ttgtcaacgg ggaaacgctg gagctgcccg tatccatctc atctttcgaa      420
aaccaggttt accgaacggc atggctgaga acaaaattta tcgacaggat tgaaggaaac      480
cccatgcaga agaaacagga atttatgctc tatccgaaag aagaccggaa tcagctgata      540
tacgaattca tcctcaggga gctgaaaaag cgctattga                             579

<210> SEQ ID NO 37
<211> LENGTH: 192
<212> TYPE: PRT
<213> ORGANISM: Bacillus licheniformis

<400> SEQUENCE: 37

Met Ser Thr Glu Asp Met Thr Lys Asp Thr Tyr Glu Val Asn Ser Ser
1               5                   10                  15

Thr Met Ala Val Leu Pro Leu Gly Glu Gly Glu Lys Ser Ala Ser Lys
            20                  25                  30

Ile Leu Glu Thr Asp Arg Thr Phe Arg Val Asn Met Lys Pro Phe Gln
        35                  40                  45

Ile Ile Glu Arg Ser Cys Arg Tyr Phe Gly Ser Ser Tyr Ala Gly Arg
    50                  55                  60

Lys Ala Gly Thr Tyr Glu Val Ile Lys Val Ser His Lys Pro Pro Ile
65                  70                  75                  80

Met Val Asp His Ser Asn Asn Ile Phe Leu Phe Pro Thr Phe Ser Ser
                85                  90                  95

Thr Arg Pro Gln Cys Gly Trp Leu Ser His Ala His Val His Glu Phe
            100                 105                 110

Cys Ala Ala Lys Tyr Asp Asn Thr Phe Val Thr Phe Val Asn Gly Glu
            115                 120                 125

Thr Leu Glu Leu Pro Val Ser Ile Ser Ser Phe Glu Asn Gln Val Tyr
        130                 135                 140

Arg Thr Ala Trp Leu Arg Thr Lys Phe Ile Asp Arg Ile Glu Gly Asn
145                 150                 155                 160

Pro Met Gln Lys Lys Gln Glu Phe Met Leu Tyr Pro Lys Glu Asp Arg
                165                 170                 175

Asn Gln Leu Ile Tyr Glu Phe Ile Leu Arg Glu Leu Lys Lys Arg Tyr
            180                 185                 190
```